US009105458B2

(12) United States Patent
Trimpin et al.

(10) Patent No.: US 9,105,458 B2
(45) Date of Patent: Aug. 11, 2015

(54) SYSTEM AND METHODS FOR IONIZING COMPOUNDS USING MATRIX-ASSISTANCE FOR MASS SPECTROMETRY AND ION MOBILITY SPECTROMETRY

(71) Applicants: Sarah Trimpin, Detroit, MI (US); Ellen dela Victoria Inutan, lligan (PH)

(72) Inventors: Sarah Trimpin, Detroit, MI (US); Ellen dela Victoria Inutan, lligan (PH)

(*) Notice: Subject to any disclaimer, the term of this patent is extended or adjusted under 35 U.S.C. 154(b) by 0 days.

(21) Appl. No.: 13/899,552

(22) Filed: May 21, 2013

(65) Prior Publication Data

US 2013/0306856 A1   Nov. 21, 2013

Related U.S. Application Data

(60) Provisional application No. 61/649,393, filed on May 21, 2012, provisional application No. 61/684,606, filed on Aug. 17, 2012, provisional application No. 61/757,040, filed on Jan. 25, 2013.

(51) Int. Cl.
*H01J 49/16* (2006.01)
*H01J 49/10* (2006.01)
*G01N 27/62* (2006.01)

(52) U.S. Cl.
CPC .............. *H01J 49/16* (2013.01); *G01N 27/622* (2013.01); *H01J 49/10* (2013.01)

(58) Field of Classification Search
CPC ................................. H01J 49/10; H01J 49/16
USPC .................................................. 250/281–300
See application file for complete search history.

(56) References Cited

U.S. PATENT DOCUMENTS 6,104,028 A * 8/2000 Hunter et al. ................. 250/288
6,265,716 B1 * 7/2001 Hunter et al. ................. 250/288
(Continued)

FOREIGN PATENT DOCUMENTS

JP            3153036 B2 *  4/2001   .............. D06B 23/24
WO    WO 2010141763 A1 * 12/2010   .............. H01J 49/26

OTHER PUBLICATIONS

Trimpin et al., "Solvent-free MALDI-MS for the analysis of biological samples via a mini-ball mill approach", Journal of the American Society for Mass Spectrometry, vol. 16, Issue 4, Apr. 2005, pp. 542-547.*

(Continued)

*Primary Examiner* — Michael Logie
(74) *Attorney, Agent, or Firm* — Occhiuti & Rohlicek LLP

(57) ABSTRACT

An ionization method for use with mass spectrometry or ion mobility spectrometry is a small molecule compound(s) as a matrix into which is incorporated analyte. The matrix has attributes of sublimation or evaporation when placed in vacuum at or near room temperature and produces both positive and negative charges. Placing the sample into a region of sub-atmospheric pressure, the region being in fluid communication with the vacuum of the mass spectrometer or ion mobility spectrometer, produces gas-phase ions of the analyte for mass-to-charge or drift-time analysis without use of a laser, high voltage, particle bombardment, or a heated ion transfer region. This matrix and vacuum assisted ionization process can operate from atmosphere or vacuum and produces ions from large (e.g. proteins) and small molecules (e.g. drugs) with charge states similar to those observed in electrospray ionization.

27 Claims, 45 Drawing Sheets

(56) References Cited

U.S. PATENT DOCUMENTS

| | | | | |
|---|---|---|---|---|
| 2004/0238754 | A1* | 12/2004 | Baranov et al. | 250/423 R |
| 2005/0077464 | A1* | 4/2005 | Truche et al. | 250/288 |
| 2006/0110833 | A1* | 5/2006 | Agnes et al. | 436/86 |
| 2006/0232369 | A1* | 10/2006 | Gorshkov | 335/306 |
| 2006/0261267 | A1* | 11/2006 | Sze et al. | 250/288 |
| 2007/0114387 | A1* | 5/2007 | Chang et al. | 250/288 |
| 2008/0067409 | A1* | 3/2008 | Corr et al. | 250/423 P |
| 2009/0272893 | A1* | 11/2009 | Hieftje et al. | 250/282 |
| 2012/0085903 | A1* | 4/2012 | Trimpin | 250/282 |
| 2012/0097845 | A1* | 4/2012 | Prosser et al. | 250/288 |
| 2012/0145890 | A1* | 6/2012 | Goodlett et al. | 250/282 |
| 2013/0086703 | A1* | 4/2013 | Maruyama et al. | 800/9 |
| 2013/0214154 | A1* | 8/2013 | McEwen et al. | 250/288 |

OTHER PUBLICATIONS product information sigma-aldrich.com.*

Zhang et al., "3-Hydroxycoumarin as a New Matrix for Matrix-Assisted Laser Desorption/Ionization Tim-of-flight Mass Spectrometry of DNA", American Society for Mass Spectrometry, 2006.*

Solouki et al. "Mass measurement accuracy of Matrix-assisted Laser Desorbed Biomolecules: A fourier-transform Ion Resonance Mass spectrometry Study", Rapid communications in mass spectrometry, vol. 8, 26-31 (1994).*

Larmore et al., "Improved matrix-assisted laser desorption/ionization mass spectrometric detection of glycosaminoglycan disaccharides as cesium salts", Rapid Communications in Mass Spectrometry, 2007;21:1315-1320.*

Chemical Book, ChemicalBook.com, 2008.*

Chen et al., "Thin-Layer Chromatography/Laser-Induced Acoustic Desorption/Electrospray Ionization Mass Spectrometry", Analytical Chemistry, col. 81, No. 22, Nov. 15, 2009.*

Perera et al., Coumarin laser dyes as matrices for matrix assisted UV laser desorption/ionization mass spectrometry, International Journal of Mass Spectrometry and Ion Processes vol. 137, 1994.*

McEwen et al., "New Paradiagm in Ionization: Multiply Chared Ion Formation from a Solid Matrix without a Laser or Voltage", Anal. Chem., 2010,82, pp. 9164-9168 Published Oct. 25, 2010.*

Cole et al., "The Asilomar Conference on Fundamentals of Atmoshereic Pressure Ionization Techniques, Oct. 8-12, 2010" J. Am.Soc. Mass Spectrom. (2011).*

Trimpin, S., et al. New Ionization Processes and Applications for Use in Mass Spectrometry. Critical Reviews in in Biochemistry and Molecular Biology, May 2013. (in press).

Musapelo, T., Murray, K.K. Particle production in reflection and transmission mode laser ablation: implications for laserspray ionization. J. Am. Soc. Mass Spectrom. 2013.

Musapelo T., Murray, K.K. Size distributions of ambient shock-generated particles: implications for inlet ionization. Rapid Commun. Mass Spectrom. 2013, 27:1283-1286.

Chakrabarty, S., et al. C.N. Matrix Assisted Atmospheric Probe Method for the Analysis of Volatile and Nonvolatile Compounds by Mass Spectrometry. J. Am. Soc. Mass SpTRIMPectrom. 2013, 10.1007/s13361-013-0634-9.

Cramer, R., et al. Liquid AP-UV-MALDI Enables Stable Ion Yields of Multiply Charged Peptide and Protein Ions for Sensitive Analysis by Mass Spectrometry. Angewandte Chemie 52(8): 2364-2367, 2013.

Inutan, E.D., et al. The Potential for Clinical Applications using a New Ionization Method Combined with Ion Mobility Spectrometry-Mass Spectrometry. Int. J. Ion Mobility Spectrom. 16(2): 145-159, 2013.

Trimpin, S., Inutan, E.D. New Ionization Method for Rapid Analysis on API Mass Spectrometers Requiring Only Vacuum and Matrix Assistance. Anal. Chem. 85(4): 2005-2009, 2013.

Trimpin, S., Inutan, E.D. Matrix Assisted Ionization in Vacuum, A Sensitive and Widely Applicable Ionization Method for Mass Spectrometry. J. Am. Soc. Mass Spectrom. 24(5): 722-732, 2013.

Inutan E.D., Trimpin, S. Matrix Assisted Ionization Vacuum, a New Ionization Method for Biological Materials Analysis using Mass Spectrometry. Mol. Cell. Proteomics 12(3): 792-796, 2013.

Nyadong, L., et al. Laserspray and Matrix Assisted Inlet Ionization Coupled to High-Field Fourier Transform Ion Cyclotron Resonance Mass Spectrometry for Peptide and Protein Analysis. J. Am. Soc. Mass Spectrom. 24(3): 320-328, 2013.

Frankevich, V., et al. Probing the mechanisms of ambient ionization by laser-induced fluorescence spectroscopy. Rapid Commun. Mass Spectrom. 26:1567-1572, 2012.

Douglass, K.A., et al. Deconstructing Desorption Electrospray Ionization: Independent Optimization of Desorption and Ionization by Spray Desorption Collection J. Am. Soc. Mass Spectrom. 23(11): 1896-1902, 2012.

Inutan, E.D., et al. Laserspray Ionization Imaging of Multiply Charged Ions using a Commercial Vacuum MALDI Ion Source. Anal. Chem. 84(21): 9079-9084, 2012.

Trimpin, S., et al. A Mechanism for Ionization of Nonvolatile Compounds in Mass Spectrometry: Considerations from MALDI and Inlet Ionization. J. Am. Soc. Mass Spectrom. 23(10): 1644-1660, 2012.

Li, J., et al. Matrix Assisted Ionization: New Aromatic and Non Aromatic Matrix Compounds Producing Multiply Charged Lipid, Peptide, and Protein Ions in the Positive and Negative Mode Observed Directly from Surfaces. 2012, J. Am. Soc. Mass Spectrom. 23(10): 1625-1643, 2012.

Richards, A.L., et al. Localization and Imaging of Gangliosides in Mouse Brain Tissue Sections by Laserspray Ionization Inlet. J. Lipid Res. 53(7): 1390-1398, 2012.

Wang, B., Inutan, E.D., Trimpin, S. A New Approach to High Sensitivity Liquid Chromatography-Mass Spectrometry of Peptides using Nanoflow Solvent Assisted Inlet Ionization. J. Am. Soc. Mass Spectrom. 23(3): 442-445, 2012.

Soltwisch, J , et al. Ion Yields in UV-MALDI Mass Spectrometry As a Function of Excitation Laser Wavelength and Optical and Physico-Chemical Properties of Classical and Halogen-Substituted MALDI Matrixes. Anal. Chem. 84(15): 6567-6576, 2012.

Lietz, C.B., et al. Inlet ionization: protein analyses from the solid state without the use of a voltage or a laser producing up to 67 charges on the 66 kDa BSA protein. Rapid Commun. Mass Spectrom. 25(22): 3453-3456, 2011.

Pagnotti, V.S., et al. Solvent Assisted Inlet Ionization: An Ultrasensitive New Liquid Introduction Ionization Method for Mass Spectrometry. Anal. Chem. 83(11): 3981-3985, 2011.

Trimpin, S., et al. Extending the Laserspray Ionization Concept to Produce Highly Charged Ions at High Vacuum on a Time-of-Flight Mass Analyzer. Anal. Chem. 83(14): 5469-75, 2011.

Wang, B., et al. Producing Highly Charged Ions without Solvent using Laserspray Ionization: A Total Solvent-free Analysis Approach at Atmospheric Pressure. Anal. Chem. 83(11): 4076-4084, 2011.

Richards, A.L., et al. Imaging Mass Spectrometry in Transmission Geometry. Rapid Commun. Mass Spectrom. 25 (6): 815-820, 2011.

McEwen, C.N., Trimpin, S. An Alternative Ionization Paradigm for Atmospheric Pressure Mass Spectrometry: Flying Elephants from Trojan Horses. Int. J. Mass Spectrom. 300(2-3): 167-172, 2011.

Inutan, E.D., et al. Laserspray Ionization—A New Method for Protein Analysis Directly from Tissue at Atmospheric Pressure with Ultrahigh Mass Resolution and Electron Transfer Dissociation. Mol. Cell. Proteomics, 10(2): 1-8, 2011.

Lomeli, S.H., et al. New Reagents for Increasing ESI Multiple Charging of Proteins and Protein Complexes. J. Am. Soc. Mass Spectrom. 21(1): 127-131, 2010.

Inutan, E.D., et al. Commercial Intermediate Pressure MALDI Ion Mobility Spectrometry Mass Spectrometer Capable of Producing Highly Charged Laserspray Ionization Ions. Anal. Chem. 83(3): 678-684, 2010.

McEwen, C.N., et al. A New Paradigm in Ionization: Multiply Charged Ion Formation from as Solid Matrix without a Laser or Voltage. Anal. Chem. 82(22): 9164-9168, 2010.

Inutan, E.D., Trimpin, S. Laserspray Ionization-Ion Mobility Spectrometry-Mass Spectrometry: Baseline Separation of Isomeric Amyloids without the Use of Solvents Desorbed and Ionized Directly from a Surface. J. Proteome Res. 9 (11): 6077-6081, 2010.

(56) References Cited

OTHER PUBLICATIONS

McEwen, C.N., et al. Laserspray Ionization on a Commercial Atmospheric Pressure-MALDI Mass Spectrometer Ion Source: Selecting Singly or Multiply Charged Ions. Anal. Chem. 82(12): 4998-5001, 2010.

Inutan, E.D., Trimpin, S. Laserspray Ionization (LSI) Ion Mobility Spectrometry (IMS) Mass Spectrometry. J. Am. Soc. Mass Spectrom. 21(7): 1260-1264, 2010. (Short Communication).

Trimpin, S., et al. Automated Solvent-free Matrix Deposition for Tissue Imaging by Mass Spectrometry. Anal. Chem. 82(1): 359-367, 2010.

Trimpin, S., et al. Laserspray Ionization—A New Atmospheric Pressure MALDI Method for Producing Highly Charged Gas-Phase Ions of Peptides and Proteins Directly from Solid Solutions. Mol. Cell. Proteomics 9(2): 362-367, 2010.

Trimpin, S., et al. A Matrix-Assisted Laser Desorption/Ionization Mass Spectrometry Method for Selectively Producing Either Singly or Multiply Charged Molecular Ions. Anal. Chem. 82(1): 11-15, 2010.

Trimpin, S., Brizzard, B.L. Analysis of Insoluble Proteins. BioTechn. 46(6):409-419, 2009.

Trimpin, S., et al. Profiling of Phospholipids and Related Lipid Structures using Multidimensional Ion Mobility Spectrometry-Mass Spectrometry. Int. J. Mass Spectrom. 287(1-3): 58-69, 2009.

Trimpin, S., Clemmer, D.E. Ion Mobility Spectrometry/Mass Spectrometry Snapshots for Assessing the Molecular Compositions of Complex Polymeric Systems. Anal. Chem. 80(23): 9073-9083, 2008.

Liu, X., et al. Mapping the Human Plasma Proteome by SCX-LC-IMS-MS. J. Am. Soc. Mass Spectrom. 18(7): 1249-1264, 2007.

Trimpin, S., et al. Fractionation and Solvent-free MALDI-MS Analysis of Polymers using Liquid Adsorption Chromatography at Critical Conditions in Combination with a Multisample On-Target Homogenization/Transfer Sample Preparation Method. Anal. Chem. 79(19): 7565-7570, 2007.

Trimpin, S., Deinzer, M.L. Solvent-free MALDI-MS for the Analysis of a Membrane Protein via the Mini Ball Mill Approach: Case Study of Bacteriorhodopsin. Anal. Chem. 79(1): 71-78, 2007.

Trimpin, S. et al. Charge-remote fragmentation of lithiated fatty acids on a TOF-TOF instrument using matrix-ionization. J. Am. Soc. Mass Spectrom. 18(1): 1967-1972, 2007.

Trimpin, S., et al. Identification of Endogenous Phosphorylation Sites of Bovine Medium and Low Molecular Weight Neurofilament Proteins by Tandem Mass Spectrometry. Biochem. 43(7): 2091-2105, 2004.

Delahunty, C., Yates, J.R. Protein identification using 2D-LC MS/MS 35(3): 248-255, 2005.

Wu, C.C., Yates, J.R. The application of mass spectrometry to membrane proteomics. Nature Biotechn. 21(3): 262-267, 2003.

Galicia, M.C., et al. Atmospheric pressure matrix-assisted laser desorption/ionization in transmission geometry. Anal. Chem. 74(8): 1891-1895, 2002.

Krause, J., et al. Studies on the selection of new matrices for ultraviolet matrix-assisted laser desorption/ionization time-of-flight mass spectrometry. Rapid Commun. Mass Spectrom. 10(15): 1927-1933, 1996.

Forward, K.M., et al. Triboelectric Charging of Granular Insulator Mixtures Due Solely to Particle-Particle Interactions. Ind. Eng. Chem. Res. 48(5): 2309-2314, 2009.

Sweeting, L.M., et al. Triboluminescence Spectra of Organic-crystals are Sensitive to Conditions of Acquisition. J. Lumin. 52:281-291, 1992.

Sweeting, L.M. 2001. Triboluminescence with and without Air. Chem. Mater. 13:854-870.

Trout, G.J., et al. Triboluminescence in Solid Methanol. Nature-Phys. Science 235(61): 174-175, 1972.

Cheng, R.J. Water Drop Freezing—Ejection of Microdroplets. Science 170(3965): 1395-1396, 1970.

* cited by examiner

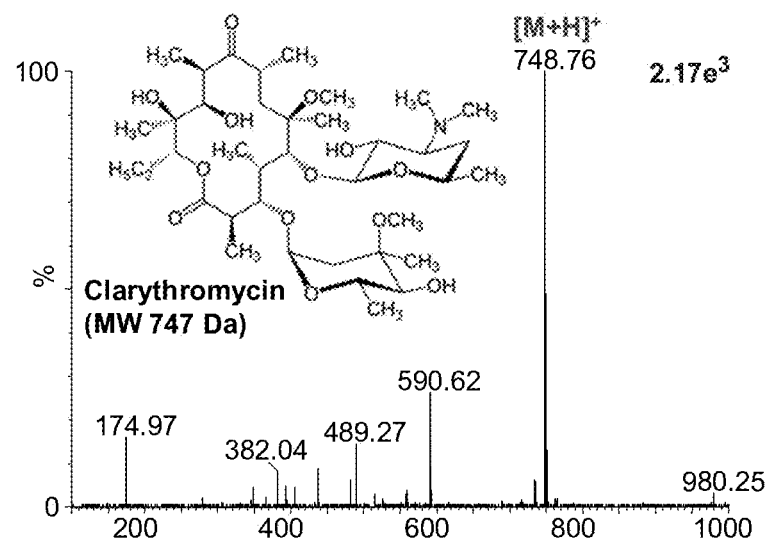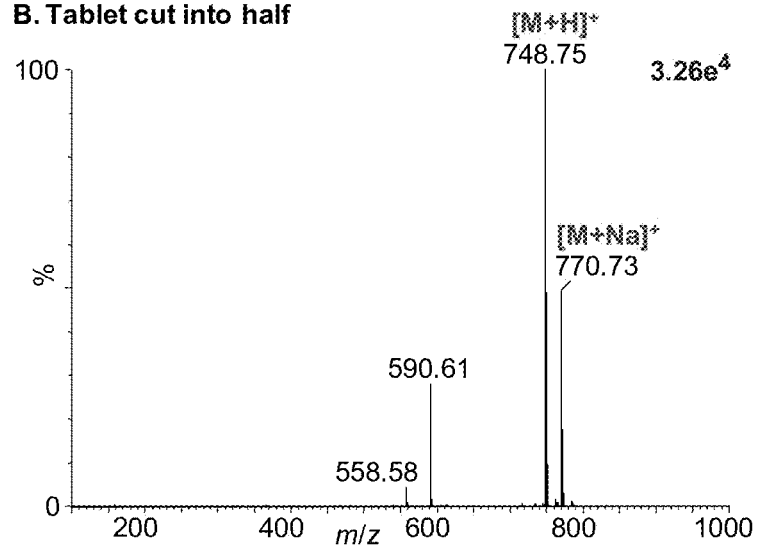
Fig. 41.

SYSTEM AND METHODS FOR IONIZING COMPOUNDS USING MATRIX-ASSISTANCE FOR MASS SPECTROMETRY AND ION MOBILITY SPECTROMETRY

CROSS-REFERENCE TO RELATED APPLICATIONS

This application claims priority to Provisional Application Ser. No. 61/649,393 filed May 21, 2012, Provisional Ser. No. 61/684,606 filed Aug. 17, 2012, and Provisional Ser. No. 61/757,040 filed Jan. 25, 2013.

FIELD OF DISCLOSURE

The disclosed systems and methods relate to mass spectrometry (MS) and ion mobility spectrometry (IMS). More particularly, the disclosed systems and methods relate to ionization facilitated by a small molecule matrix and sub-atmospheric pressure conditions.

BACKGROUND OF THE DISCLOSURE

Compounds are currently ionized in vacuum (herein defined as low pressures relative to atmospheric pressure) ion sources of a mass spectrometer by first evaporating the analyte followed by gas-phase ionization as in electron ionization or chemical ionization, or by laser ablation of the analyte either directly or in a small molecule (chemical) matrix as in matrix-assisted laser desorption/ionization (MALDI), or by use of a high velocity particle or ion as in secondary ionization mass spectrometry (SIMS) and fast atom bombardment (FAB), or by methods such as field desorption where a high voltage is placed on emitters having sharp edges or tips to generate ions, or thermospray ionization where a solution flowing into a low pressure region is heated to rapidly effect vaporization and ionization or by placing a voltage on a solution flowing from a capillary as in electrospray ionization (ESI). All of these methods require a high energy means of producing gas-phase ions for mass analysis of analyte.

The current practice for analysis of compounds which cannot be vaporized without destruction by heat is to use MALDI or ESI, and variants thereof, or the newly developed methods of inlet ionization termed laserspray ionization inlet (LSII), solvent assisted ionization inlet (SAII), and matrix assisted ionization inlet (MAII), and vacuum ionization methods termed laserspray ionization vacuum (LSIV).

MALDI is typically used with a time-of-flight (TOF) mass spectrometer and is commonly referred to as MALDI-TOF. The source region operates at very low pressure (high vacuum). MALDI uses a small molecule matrix such as 2,5-dihydroxybenzoic acid (2,5-DHB) to facilitate ionization of nonvolatile analyte but requires an expensive laser and extraction voltage, and produces mostly singly charged ions. MALDI-TOF instruments are costly and dedicated to MALDI analysis. Limitations of MALDI include high matrix related background, hot/cold spot issues leading to irreproducibility and thus are not readily applicable to extracting quantitative data. Intermediate pressure MALDI sources, operating in the milli-Torr and sub-milli-Torr pressure range, can be interfaced with instruments that are multipurpose and provide high sensitivity analysis, but these ion sources and associated lasers are also expensive. A variant of MALDI called atmospheric pressure MALDI produces ions at atmospheric pressure before entering the mass spectrometer inlet, which in the presence of the extraction voltage cause loss of ions at the inlet aperture ('rim loss'). Atmospheric pressure MALDI sources are available that operate on instruments designed for electrospray ionization (ESI) but are less sensitive than vacuum MALDI. Because MALDI produces primarily singly charged ions, the intermediate pressure and atmospheric pressure MALDI sources interfaced with instruments having limited mass-to-charge (m/z) range for singly charged ions limits the utility of the method to compounds within the limited mass range of the instrument. Therefore, for analysis of intact, high-mass compounds such as proteins, the MALDI-TOF instrument, with unlimited mass range is required. Contrary, proteins and protein complexes can be digested by enzymes and analyzed using high performance mass spectrometers (as in e.g., 'bottom up', 'shot gun proteomics') at the expense of the intact analyte information, time, cost, and expertise. Small molecule analysis is limited by the matrix background in competition with the ionization of the desired analyte (e.g., drugs and metabolites) at any of the pressure regimes used in MALDI. MALDI requires a laser and for vacuum MALDI, sample introduction from AP to vacuum is time consuming and requires expensive instrument modifications. Typical lasers for use in MALDI use laser fluencies of generally between 2 and 60 kJ m$^{-2}$. Inducing fragmentation using collision-induced dissociation (CID) of singly charged ions produces little sequence (e.g., peptides) information, especially of fragile posttranslational or other chemical modifications that frequently are lost preventing structural information of the analyte to be obtained. Newer and improved fragmentation methods such as electron transfer dissociation (ETD) and electron capture dissociation (ECD) are not applicable to singly charged analyte ions. Because of the use of a laser, MALDI is a harsher method relative to, for example, LSI (laser fluencies of generally between 40 and 150 kJ m$^{-2}$ with the laser aligned in transmission geometry) or ESI limiting applications to more sturdy, less fragile molecules and rarely to the analysis of e.g., molecular non-covalent complexes, MALDI can analyze molecular complexes after chemical crosslinking the complex prior to MALDI mass analyses.

One-Dimensional (1-D) and 2-D gel electrophoresis, sodium dodecyl sulfate polyacrylamide gel electrophoresis (SDS-PAGE) and agarose gels are used in protein and deoxyribonucleic acid (DNA)/ribonucleic acid (RNA) separation and purification, and which can be coupled with ESI and MALDI-MS as well as ion mobility-MS and MS/MS but indirectly by digesting the macromolecule(s) in the gel slice and subsequently solution extracting it from the gel environment. Nevertheless, MS overcomes the need for specific and expensive antibodies for detection using, for example, Western blots; many compounds do not have specific antibodies and therefore cannot be detected. More commonly applied are liquid chromatography (LC)-MS and MS/MS or ion mobility-MS approaches for additional separation. Common to both ESI and MALDI, and the methods derived from them, are ion suppression issues, problems with the presence of salt, and robustness.

MALDI operates from the solid state and is a surface method enabling molecular surface imaging approaches to determine the localization of certain analytes within a surface. A voltage is applied, frequently several kilovolts, to lift the ions from the surface and accelerate them to the analyzer. The matrix requires having sufficient absorption at the laser wavelength used to enable matrix desorption from the surface. Analyte ionization occurs in a region very near the matrix surface (<100 microns from the surface). A notable degree of chemical background associated with the desorption process creates significant background noise especially in the low mass region (<800 m/z). MALDI is therefore limited in this mass range for which applications range from drug development (clinical applications) to forensic analyses. To increase the speed, especially for imaging applications, expensive high repetition lasers can be employed to desorb/ionize more rapidly enable the measurement of summed mass spectra from ~100 laser shots and, in case of imaging of surfaces, ions in each mass spectrum are used to determine analyte location employing respective computing programs. Thus, the mass spectra generated from ~100 laser shots are summed into a single mass spectrum which represents one pixel in the image. Advantages of the MALDI method is that predominantly singly charged ions are produced so that interpretation is simplified, which is important for complex mixtures.

ESI is an ionization method whereby a voltage, usually several thousand volts, is placed on a capillary through which a solution is passed relative to a counter electrode which contains the inlet entrance to the vacuum of the mass spectrometer. Highly charged liquid droplets are formed in the ESI process and desolvation of these droplets leads to formation of bare ions that are analyzed by the mass spectrometer. While the MALDI method produces primarily singly charged ions, the ESI liquid introduction method produces ions of high charge states when multiple ionization sites exist on the analyte molecule. ESI methodology is not well suited for surface analysis, although a method called desorption electrospray ionization (DESI) can sample surfaces but with rather poor spatial resolution and limited in upper molecular weight range of nonvolatile compounds. A newer variation, nano-DESI, enables improved spatial resolution measurements at the expense of critical alignment and expertise. Combined methods of laser ablation of a surface with capture of the ablated material in the ESI plume can also be used to image surfaces.

Because ESI produces multiply charged ions, the method is useful with high performance mass spectrometers having limited mass range and the multiply charged ions provide improved fragmentation efficiency using e.g., CID, ECD, and ETD relative to singly charged ions making analyses on high performance mass spectrometers with limited m/z range suitable. To increase analyte charge, small amounts (frequently <10% volume) of so-called supercharging reagent can be added to the solution instead or additionally to other reagents such as acids. Detection of multiply charged ions relative to singly charged ions is more efficient, as is the ion mobility gas-phase separation of analyte ions. However, ESI requires the analyte to be in a suitable solvent to provide "sprayable" conditions. ESI is softer than MALDI making it applicable to analyzing protein complexes with suitable solvent conditions applied. ESI can be combined with "online" LC for pre-separation applicable for soluble analyte samples. This approach is not applicable for solubility restricted or insoluble analytes or where spatial and temporal resolution matters.

Numerous ionization approaches under the terminology ambient ionization have been developed to circumvent some of the problems associated with ESI and MALDI. All ambient ionization methods capable of ionizing nonvolatile compounds are variants of ESI and MALDI and while they offer advantages for certain analyses, they all increase the complexity of the ion source. None of these methods offers a simple means of rapidly introducing analyte for conversion to gas-phase ions for analysis by MS. All these methods require use of high voltage, lasers, or other sources requiring application of energy or force to the sample. Further, the current means are not well suited for automated high throughput analysis because of expense or problems associated with robustness of the methods.

New ionization methods have recently been introduced. Inlet ionization methods used in MS include laserspray ionization inlet (LSII), matrix assisted ionization inlet (MAII), and solvent assisted ionization inlet (SAII). All of these methods produce abundant highly charged ions without the use of a voltage from the solid state (MAII, LSII) or solution (SAII). Ionization occurs in a heated channel (inlet) that connects a higher pressure region (typically atmospheric pressure) and a lower pressure region (typically the first vacuum region of a mass spectrometer. In practice, the matrices or solvents disclosed for these methods require that the channel be heated to greater than 150° C. and analyte ion abundance reaches a maximum between 250 and 450° C. Ion abundances reported for these methods are not analytically useful below 150° C. The mechanism of ionization of the inlet ionization methods is purported to involve creation of droplets of matrix or solvent within the heated channel with an excess of one charge at the droplet surface and an excess of the opposite charge in the bulk of the droplet. Removal of the surface layer by for example superheating the droplets as they traverse from the high to the low pressure regions with rapid bubbling on nucleation of the droplet. However the analyte ions are formed, the ionization event occurs inside the heated channel linking a higher and a lower pressure region.

With LSII, a laser ablates the matrix with incorporated analyte, the sample, into the heated inlet where ionization occurs. In MAII, the sample is introduced physically into the heated channel producing identical ionization as LSII with the same sample. In SAII, a solvent replaces the small molecule matrix and similarly produces analyte ions when introduced into the heated channel. In all inlet ionization methods, similar to MALDI, the matrix, or solvent, is present in the sample in orders of magnitude higher molar ratio relative to the analyte.

LSII-MS is a surface method that has the potential to characterize macromolecular structures directly from their native and complex environment with high spatial resolution important in surface imaging, similar to MALDI, but producing abundant highly charged ions as long as heat can be applied to the inlet tube. Mass spectrometers with skimmer cone inlets have been retrofitted with a heatable inlet tube to produce analytically useful analyte ions for analysis by mass spectrometry. Contrary to MALDI, LSII does not require the absorption by the matrix compound at the laser wavelength. The laser can create a shockwave so that the matrix:analyte association is ablated into the heated inlet tube. LSII was introduced on high performance mass spectrometers operating at atmospheric pressure without the application of any electrical field demonstrating its usefulness for tissue analysis and surface imaging.

A requirement for all of the inlet ionization methods is a heated inlet tube linking atmospheric pressure and the vacuum of the mass spectrometer, requiring the inlet channel be heated to greater than 150° C. for analytically useful results, especially when organic matrices are used as in MAII or LSII. Most mass or ion mobility spectrometer ion sources are not equipped with such a heated inlet tube and must be retrofitted. A large number of small molecule compounds have been shown to produce multiply charged mass spectra of peptides and small proteins at inlet temperature >400° C. Even so, the matrices reported for MAII and LSII that require a hot inlet to produce ions in good yield are also sufficiently nonvolatile that they collect on ion transmission elements within the instrument causing contamination over time and loss of instrument sensitivity. More volatile matrix compounds would alleviate this problem and a few (1,4-dihydroxy-2,6-dimethoxybenzene (DHDMB), salicylamide, 3,4-dihydroxyacetophenone, mono-methylfumarate, 4-trifluoromethylphenol) were discovered that produce analytically useful gas phase analyte ions when introduced into a heated inlet channel when the channel was heated to less than 150° C. and as low as 50° C. Some of these matrices (e.g., DHDMB) produced multiply charged analyte ions when introduced to a skimmer cone inlet using a source block temperature of 150° C., or by laser ablation of the sample in vacuum. This latter vacuum method in which an inlet channel is not available and the only energy or force supplied to the sample is from the laser is called laserspray ionization vacuum (LSIV).

LSIV was introduced on vacuum sources offering advantages and disadvantages described above for MALDI (vacuum source) except that it has an additional advantage of producing multiply charged ions from analyte similar to SAII, LSII, MAII, and ESI. Conditions for LSIV operation combine the requirements of LSII and vacuum MALDI requiring sufficient absorption of the matrix at the wavelength of the laser used and in a timeframe that allows the matrix to be removed from the matrix:analyte association by desolvation which are stringent experimental conditions. Similar to MALDI, fragile gangliosides cannot be analyzed using LSIV, contrary to LSII. The most prominent LSIV matrix at intermediate pressure is 2,5-dihydroxyacetophenone (2,5-DHAP), also used as a MALDI and LSII matrix. The most prominent LSIV matrix at low pressure (high vacuum) is 2-nitrophloroglucinol (2-nitro-benzene-1,3,5-triol, 2-NPG). In LSIV, a laser is used to desorb/ablate the sample from vacuum conditions to form multiply charged ions directly from surfaces in intermediate pressure and low pressure mass spectrometer ion sources. Without a means of supplying heat to desolvate the charged matrix:analyte particles or droplets produced by laser ablation, LSIV is limited in its ability to analyze higher molecular weight proteins. The largest protein detected to date on an intermediate pressure source is lysozyme, molecular weight 14300, with charge states identical to ESI and inlet ionization methods using the same Waters SYNAPT G2 (Quadrupole ion mobility spectrometry (IMS) TOF mass spectrometer with a 8000 m/z upper limit). With a low pressure MALDI-TOF source, LSIV produces multiply charged ions of carbonic anhydrase.

The method described herein differs from and improves the above described ionization methods. This method produces multiply charged ions by using a matrix that when exposed to sub-atmospheric pressure conditions spontaneously produces analyte ions of charge states similar to the inlet ionization methods, but without the need of a heated channel or a force that allows the matrix:analyte association to enter the gas phase. Unlike with inlet ionization, the initial ionization event occurs from the surface of the substrate upon which the matrix:analyte, the sample, is placed by exposing the sample to sub-atmospheric pressure available with any mass spectrometer. The MAIV process is spontaneous and continues without the application of a force. No external energy is necessary, so that ionization is initiated by the energy already in the system. This initial ionization event is not dependent on a heated channel, but is affected by heat, which can be above or below room temperature, applied to the substrate, and requires exposure to sub-atmospheric pressure to initiate the ionization event. Thus, simply placing the sample using an appropriate matrix compound into a vacuum ion source of a mass spectrometer initiates the ionization event that produces abundant analyte ions. Likewise, by placing the sample in sub-atmospheric pressure conditions using an atmospheric pressure ion source inlet, such as is used with ESI, using an appropriate matrix the ionization event is initiated spontaneously. In either case, heating or cooling the substrate onto which the sample is placed, using methods known to those practiced in the art, extends the compounds that spontaneously produce ions from the method described herein. This method will be referred to as matrix assisted ionization vacuum (MAIV) and matrices that produce analyte ions by this method for analysis by mass spectrometry or ion mobility are referred to as MAIV matrices. MAIV is usefulness for tissue analysis and surface imaging of such as those of endogenous and exogenous origin and examples include drugs, metabolites, pesticides, lipids, peptides, proteins, chemically or posttranslational modified peptides or proteins, protein complex, receptors, ligands, catalysts, carbohydrates, glycans, antibodies, biomarkers, and other compounds produced by synthesis, such as synthetic polymers, on mass range limited mass spectrometers. These analytes can be pure or present in biological/synthetic environments such as urine, blood, skin, tissue sections, biofilms, eatable goods, flesh, vegetable surfaces, drug pills, bacterial, microbial, artificial bone, archaeological artifacts, painting, or synthetic polymer films, and others. The production of highly charged ions directly from surfaces in a soft manner and in high abundance allows sequencing of for example peptides and proteins using for example ETD.

SUMMARY OF THE DISCLOSURE

Embodiments disclosed herein provide systems and methods for producing ions, singly or multiply charged, and analyzing compounds of widely varying molecular weights including small molecules as well as macromolecules using matrices and vacuum and referred to as matrix assisted ionization vacuum (MAIV). We disclose here the ability to incorporate analyte into a matrix, or into a solvent in which the MAIV matrix is dissolved, called the sample, to produce ions from the analyte when the sample is introduced into a sub-atmospheric pressure (vacuum) region of a mass spectrometer or ion mobility spectrometer. With this method, analyte ions are produced without need of any high energy source such as a laser, high voltage, or high velocity particle for ion generation. The ions produced by this method have charge states similar to ESI, LSII, LSIV, and MAII. Thus, proteins are multiply charged and fall within the m/z range of mass spectrometers commonly used in MS.

In MAIV, analyte ions are created at the surface of a sample holder or substrate without the use of a laser or voltage producing ions in charge states similar to ESI. The MAIV the sample can be manipulated from atmospheric pressure or from the vacuum of common ion sources but does not necessitate an ion source now common with all mass spectrometers. The ion source can be eliminated using only an inlet to the mass spectrometer which can be simply a pin-hole leak. The diameter size of the hole and the type of substrate define the applications. In any case ionization is through exposure to sub-ambient conditions in which the sample is in fluid contact with sub-ambient pressure of the mass or ion mobility analyzer. When the sample is exposed to sub-atmospheric pressure, ionization commences spontaneously and is continuous until the matrix in the sample is depleted or, for multiple sample, the sample substrate is moved to the next the sample or removed from the sub-atmospheric pressure region. Ionization can be prolonged by, for example, cooling the substrate, or intensified but for a shorter duration by heating the substrate. From the same sample through changes of the voltages, especially in the source region, multiply and singly charged MAIV ions can be formed of peptides at will.

The MAIV matrices so far discovered when placed in sub-atmospheric pressure, or heated to less than 150° C., or placed in vacuum and heated to less than 100° C., splinter matrix particles from the surface. These particles have charge. It is therefore postulated that this splintering process initiates the ionization event, but ionization directly from the matrix surface is possible. The charged particles splintered from the surface may undergo further splintering producing smaller charged particles. The splintered particles have either excess positive or excess negative charge.

Similar to all ionization methods that produce analyte ions from charged droplets or particles, a process is necessary to remove the matrix or solvent, commonly referred to as desolvation. In ESI a heated gas or heated inlet tube are used to desolvate the droplet and release the bare analyte ion. With some MAIV matrices, no external energy is required to produce the bare analyte ions. However, by providing external energy, a wider range of compounds act a MAIV matrices spontaneously producing charge particles which, when desolvated, produce the bare analyte ions. Means of enhancing evaporation of the sample as well as subsequent desolvation of charged particles from MAIV matrices include radiative (e.g. infrared (IR), visible, ultraviolet (UV)) or convective heat, microwave and radiofrequency radiation, collisions with gas or surface, and other means known to those practiced in the art. Frequently, improved desolvation increases the ion abundance observed and enhances CID and ETD fragmentation. Therefore, MAIV matrices evaporate or sublime under sub-atmospheric pressure at temperatures below 150° C. and ideally below 75° C.

According to the above postulates the MAIV matrix must splinter off particles from the matrix surface that have excess positive or negative charge. One means of producing a charge when a surface cracks (splinters) is through the mechanism that produces triboluminescence or light when a crystal is crushed. The light, or lightening is caused by a discharge between cracked surfaces that have opposite charges. Some of the known MAIV matrices are also known to triboluminescence. The above mechanistic discussion is meant to provide insight and if not found to be correct in its entirety in the future, will not alter the claims of this application.

With a MAIV matrix, the sample can be exposed or inserted to sub-atmospheric pressure of a mass spectrometer or ion mobility spectrometer, by default available, and analyte ions (of positive and negative charge, hereafter referred to positive and negative ions) are produced without a laser or a high voltage. Voltages are used to guide the ions to and through the analyzer and to the detector.

MAIV matrices produce ions spontaneously when exposed to sub-atmospheric pressure. Some MAIV matrices spontaneously produce analyte ions at ambient temperature and others require the matrix be heated, typically by heating the substrate to less than 150° C. and preferably less than 100° C. at or near atmospheric pressure. With MAIV matrices that evaporate or sublime at sub-atmospheric pressure only when heat is applied to the matrix or its substrate, desolvation energy usually enhances ion abundance. The MAIV ion formation is continuous as in ESI. These matrices may benefit from added heat/cold to a channel connecting two different pressure regions, or to the sample substrate (the sample holder), but unlike reports for inlet ionization (especially MAII), in which optimization was reported to occur between about 250 and 450° C., MAIV matrices optimize at temperatures between −80° C. and +150° C. (if no sign is provided, the temperature is above 0° C.), and produce analytically useful analyte ionization between room temperature and about 75° C. at or near atmospheric pressure. The optimal pressure/temperature values change similarly to the pressure/temperature phase diagram associated with a matrix compound. Also, unlike inlet ionization an inlet (e.g., a channel or inlet tube, or skimmer is not a requirement and the ionization event is not initiated by using a force to transfer the matrix: analyte sample into the inlet.

The substrate with the MAIV the sample can be mechanically introduced to a vacuum source similar to solid probe introduction in electron and chemical ionization methods or sample plate introduction in analyte ionization commences as soon as the sample experiences the sub-atmospheric conditions without the use of a laser or the use of a heated channel. Spontaneous ionization can be controlled through temperature control of the substrate surface, the use of matrix combinations, or limiting the exposure to the vacuum conditions by, for example, placing the sample within a capillary that allows only a small surface area of the sample to experience the sub-atmospheric pressure. Because some of the MAIV matrices optimize at or around ambient temperature and use no high voltage or laser, in principle, any mass spectrometer with any ion source or inlet configuration is operational with MAIV. Commercially available inlets of atmospheric pressure ion sources (e.g., skimmer or inlet tube), with or without modifications, can be exposed to the operator without need of the ion source enclosure because the inlet for these MAIV matrices can be near ambient temperature and without application of more than a few volts for focusing the ion beam. Further, the only requirement for ionization being the vacuum inherent in the operation of the analyzer, the energy necessary to operate the instrument for the sample ionization is reduced. Thus, this safe and low energy requirement ionization method is ideal for field portable instruments as well as for fragile compounds (protein complexes, posttranslational protein modifications such as phosphorylations, fragile chemical modifications such as catalysts, or gangliosides containing fragile sialic acid modifications are examples that tend to fragment or explode using high energy ionization sources (MALDI). Further, the simplicity and robustness of the MAIV method makes it potentially useful for clinical analyses.

The disclosed system and method comprises placing a matrix with incorporated analyte in fluid contact with a region of sub-atmospheric pressure, typically generated by the pumping system of an ion mobility or mass spectrometer. This MAIV method is applicable to vacuum ion sources such as used with matrix-assisted laser desorption/ionization (MALDI) or with electron (EI) or chemical ionization (CI), and atmospheric pressure ionization (API) sources used with electrospray ionization (ESI) or atmospheric pressure chemical ionization (APCI), but does not require a laser as in MALDI, added heat as in EI, CI, or APCI to vaporize volatile compounds, or a high voltage as used in ESI and in MALDI. Methods are described that are capable of producing abundant singly or multiply charged ions for use in MS and ion mobility-MS and MS/MS using fragmentation methods including collision-induced dissociation (CID), electron transfer dissociation (ETD), and electron capture dissociation (ECD) as examples. The systems and methods can be modified for certain advantages by using smaller or multiplexed surfaces/containers, and high throughput analyses using matrices with low thermal requirements for analyte ion formation, or with the addition of heat or cooling supplied to the sample surface or substrate, or to the inlet region, or by additional of a gas slow (preferably air) in close proximity to the sample or aimed at the sample to provide enhanced ion abundance to obtain structural characterization using (CID) and high performance fragmentation such as ECD or ETD known to those practiced in the art.

This method allows analysis of compounds having a wide range of volatility as well as compounds of widely differing molecular weights by simply introducing the analyte in an appropriate matrix into a vacuum region of a mass spectrometer. For example, bovine serum albumin (BSA), molecular weight 66 kDa, produces abundant multiply charge molecular ions using the matrix 3-nitrobenzonitrile (3-NBN) with the sample (matrix:analyte) placed in solution on e.g., a traditional MALDI plate, dried (although the drying step is not necessary as it can occur within the vacuum system), or, alternatively the matrix and analyte can be ground together (the sample prepared 'solvent-free'; it should be understood that the phrase "solvent-fee" covers means that avoids the use of a solvent during matrix deposition), and inserted into the intermediate pressure MALDI source of, for example, a Waters Corporation SYNAPT G2 mass spectrometer. Highly charged protonated molecular ions are observed and fragment ions can be generated, especially from highly charged ions using CID, ETD, ECD and variations thereof. Other MAIV matrices include 2-nitrobenzonitrile (2-NBN), 5-methyl-2-nitrobenzonitrile, coumarin, methyl-2-methyl-3-nitrobenzoate, methyl-5-nitro-2-furoate, bronopol (2-bromo-2-nitropropane-1,3-diol), as well as 3-nitrobenzaldehyde working well when prepared 'solvent-free' additionally or in substitution to solvent-based sample preparations. In general, the compounds for matrix are within the range between 50 and 600.

Alternatively, the mass spectrum can be obtained using a API inlet typically used with ESI by maintaining the inlet below 150° C., and preferably below 100° C. and placing the sample or matrix solution and then analyte solution, or vice versa, onto, for example, filter paper and placing the sample on the filter paper substrate against the inlet aperture. The paper creates sufficient vacuum for ionization to occur even though some air is able to flow through the gas permeable paper. MAIV matrices provide the first example of converting nonvolatile compounds to gas phase ions by simply exposing matrix/analyte, the sample, to sub-atmospheric pressure. 6-Nitro-o-anisonitrile, and phthalic anhydride are examples of MAIV matrices that produce ions with vacuum assistance at ambient temperature additionally to those compounds that function as MAIV matrices on the vacuum source (listed in [00026]). 2,5-DHAP is an example of compounds that are MAIV matrices when heat is applied to the substrate or matrix.

Unlike MAII in which heat is applied to the inlet, in MAIV heat can be applied directly to the matrix by, for example, heating the substrate to which it is deposited. This is advantageous relative to MAII in that the requirement of a heated inlet to produce ions is eliminated so that a wider range of instruments and conditions are useful with MAIV. Any compound that produces gas-phase ions by exposure to sub-atmospheric pressure when cooled, at ambient temperature, or when the matrix is directly heated is considered a MAIV matrix. These matrix compounds sublime or evaporate when exposed to sub-atmospheric pressure at ambient temperature or at temperatures below about 100° C. and spontaneously produce ions from incorporated analyte for analysis by mass or ion mobility spectrometers. Because charged matrix:analyte particles or droplets are believed to be the source of analyte ion formation in MAIV, desolvation of the charged particle/droplet can be enhanced with, for example, application of heat, collisions of the charged particles/droplets with gas or a surface, and by fields such as radiofrequency fields used in MS.

In MAIV, ionization can be enhanced by shaking the substrate by, for example, vibrations produced by an ultrasonic or a piezoelectric device or simply by a vortexer. Adding heat or cold to the surface on which the matrix is applied also can alter the ion abundance observed. Using these methods, the ionization event can be made to have a short duration with increased ion abundance per unit time, or to be prolonged with less ion abundance over extended time. Ionization can also be prolonged by limiting the area of the sample exposed to sub-ambient conditions such as but not limited to the use the sample deposited inside of a capillary tube or pipet tip, made of, for example, glass, metal, or polymer, instead of being placed on a flat surface. Heating the matrix or the surface onto which the sample is applied allows a wider range of compounds to perform as MAIV matrices. For example, 3-NBN produces abundant ions at sub-atmospheric pressure at substrate temperatures at least as low as 25° C., whereas 2,5-DHAP produces analytical useful results when heat (>60° C.) is applied to the substrate.

MAIV is applicable with any instrument that has an ion source operated under vacuum conditions. Such instruments are commonly used with gas chromatography (GC)/MS and having electron and chemical ionization sources, as well as with MALDI sources. With a vacuum source, the sample consisting of a MAIV matrix with incorporated analyte need only be exposed to the vacuum to begin producing ions. Heat applied to the substrate holding the sample under vacuum conditions is useful for enhancing ion formation with some matrices. Various methods for applying energy to aid desolvation of charged particles/droplets downstream from the surface, such as collisions, IR, microwaves, and radiofrequency radiation, and other approaches known to those practiced in the art can be used to increase analyte ion abundance. If the sample is placed close to ion extraction and focusing lens, known to those practiced in the art, the analyte ions produced from the MAIV matrix will be accelerated and guided to travel through the mass analyzer or ion mobility device to the detector where a signal is generated for amplification and conversion using a computer to provide an output.

Alternatively, ion sources that are designed to work with atmospheric pressure ionization methods such as ESI, APCI, and atmospheric pressure MALDI also work with MAIV. There are a number of possibilities for producing analyte ions for MS analysis using MAIV at atmospheric pressure. Simply exposing the MAIV matrix to the entrance aperture of an API inlet on a substrate creates sufficient vacuum for ionization to commence. Holding the substrate, to which the sample is applied, onto the inlet aperture of the mass or ion mobility analyzer produces ions by creating a perfect or an imperfect vacuum seal at the entrance. A permeable surface such as filter paper with the sample applied and dried can be placed against the entrance, or a modified entrance having a larger aperture, to produce ions from larger sample surfaces or multiple samples deposited (e.g., ideally using multichannel pipet dispenser) on the substrate. Applying multiple samples to a strip of paper, or appropriate ribbon, and moving the strip or ribbon to successively expose the samples to the vacuum produces a high throughput means of analyzing multiple samples individually. The samples not exposed to the vacuum may be at atmospheric pressure. Likewise, the sample can be applied in a 2-dimensional array (e.g., a 96-well plate or pipet tip array for loading of multiple samples simultaneously to the 2-D substrate) and an x, y, (z)-stage employed to sequentially places the samples at the entrance aperture of the mass or ion mobility spectrometer. With API inlets, typically air flow is preferred so that air permeable substrate or an imperfect seal provides optimum results. A solution consisting of the matrix, analyte, and a volatile solvent such, but not limited to, methanol, acetonitrile, water, and mixtures thereof can be injected into the channel to produce analyte ions. This method is also subject to high throughput analyses.

With MAIV, the inlet linking atmospheric pressure and vacuum can have various size openings, including some larger than the pumping capacity of the instrument allows, so long as the substrate produces a sufficient vacuum seal not to vent the instrument. An isolation valve, as for example a ball valve, can be used to isolate the vacuum of the instrument from atmospheric pressure when the sample substrate is not against the inlet aperture.

One means of rapid and automated sampling is the use of well plates with the samples in the wells. A well can be pushed against the inlet aperture or the aperture of an extension of an inlet tube to create the sub-atmospheric pressure at the well bottom. The sample in the well is ionized and swept into the analyzer for separation by mass-to-charge or size, shape (also known as cross section), and charge. The well plate can be moved to expose the next well to the vacuum of the analyzer through the inlet. Turning off the vacuum isolation valve, which can be done automatically, allows larger inner diameter inlet tubes to be moved to the next well position without venting the instrument. Larger inlet inner diameter channels may improve the sensitivity of the analysis, but at the expense of requiring an in-line valve. A flat surface can be analyzed in a similar fashion to the well plate by having the inlet aperture with a sufficiently large opening to cover the entire sample. This can be done using, for example, a conical inlet.

Another alternative approach is to use, for example, a valve, such as a ball valve, that has indentations to hold small containers in which the sample is placed. A container holding the sample can be loaded into one of the indentations of the valve at, as a simple example, the upper position of a four indentation valve. The upper indentation and lower indentation are open to atmospheric pressure and the horizontal indentation opens to the analyzer vacuum. Turning the valve in one direction moves the upper position with the container to the position that exposes it to the instrument vacuum. If a container is used to hold the sample, the entrance to the vacuum in some embodiments is too small for the container to enter the opening. Ionization commences on exposure of the sample to sub-atmospheric conditions. In this position, the new upper indentation can be automatically loaded with the sample or blank or a container with a blank or the sample. Once sufficient ion current is accumulated, a computer can send a signal to turn the valve so that the spent container is now in the bottom position and falls into a waste collection and the second the sample is simultaneously exposed to vacuum to initiate ionization while the top position is again ready to be loaded with another the sample. Blanks can be run between the samples to eliminate potential carryover. Ions produced by such an arrangement can be guided into the analyzer for analysis using a gas flow or using lens elements, including radiofrequency guides known to those practiced in the art. Other arrangements which will be obvious to those practiced in the art can be used with MAIV matrices to produce analyte ions for high throughput with and without automation. Examples are tissue analysis, drug analysis, protein and peptide analysis, carbohydrate analysis, and in general small and large molecule analysis.

Besides the ease of ionization, low cost, and safety of MAIV and its application to a wide array of instruments and approaches, the method also provides advantages for ionization where a low energy ionization process is preferred. An example is the analysis of complexes, such as protein-drug, or protein-protein complexes which are unstable to any energy source. Another application is in studying ion structures (cross sections) by ion mobility where energy supplied in the ionization process can affect the ion structure. Another example is the ability to observe structures directly from surfaces, as in biological tissue, to characterize the compounds in the tissue without application of energy, as happens with, for example, MALDI analysis. Yet another example is in the analysis of analyte in thin layer chromatography (TLC) plates, paper chromatography, and 1-D and 2-D gel electrophoresis or from LC in an online or offline approach. Analysis of blood spots directly from paper is yet another example. The substrate can be precoated with matrix so that analyte only needs to be added. Such a simple and robust ionization process, requiring only application of a matrix solution and exposure to sub-atmospheric pressure and capable of ionization of volatile (e.g., drugs) and nonvolatile compounds (e.g., large proteins, fragile complexes or modifications), is expected to have numerous applications including in clinical analyses (e.g., high speed sample introduction of biological matrixes such as urine and whole blood), omics applications (using e.g., the more traditional bottom up approaches based on 1-D and 2-D gels or LC or in top down proteomics), field portable instruments, and forensic analyses.

An additional advantage of this method relates to sensitivity. Ionization initiated through vacuum conditions is more sensitive than ionization initiated at atmospheric pressure because the transfer of ions from atmospheric pressure to vacuum is an inefficient process. This is directly seen with MALDI-TOF (a vacuum ionization method) instruments which have comparable or better sensitivity than ESI (an atmospheric pressure ionization method) even though the efficiency of ionization is orders of magnitude less than the ionization efficiency of ESI. Thus, the MAIV method of ionization is highly sensitive because ions are formed under vacuum conditions eliminating the disadvantageous transfer of ions from atmospheric pressure to the vacuum of the analyzer.

Another advantage of this method relates to continuous ion formation. One distinct advantage of this is that no hot/cold spot issues are observed which limit MALDI applications. In MAIV, the sample can be rapidly changed, contrary to the best efforts used with ESI and without cross contamination either through rapid moving surfaces (e.g., using an 'endless' paper) or containers (e.g., using a ball valve arrangement). The continuous ion formation is also ideal for improved fragmentation to determine the structure of an analyte using CID, ETD or ECD as examples.

A difficulty of the MAIV approach with ion sources built for vacuum ionization is that MAIV matrices that do not require a heated substrate are volatile in vacuum and evaporation/sublimation begins as soon as the sample is placed under sub-atmospheric pressure conditions. The pump down time to reach a sufficiently low pressure for the mass spectrometer to operate can result in evaporation or sublimation of the sample in its entirety if the matrix is too volatile. This can be circumvented to some extent by cooling the sample and/or the substrate before placing the sample on the substrate into the instrument. Another solution is to have a mechanically cooled substrate by, for example, refrigeration of the substrate or the substrate housing. Restricting the sample surface area exposed to vacuum also extends the time for ion formation, but at the expense of lower ion abundance during any single acquisition. Smaller pumping volumes can be engineered to allow fast pump down so that less of the sample is lost before the instrument is ready to acquire data.

Another problem relates to the difficulty of introducing multiple the samples into the vacuum for analysis. These problems are circumvented by having a system, where only one of the samples is exposed to vacuum at any one time. These approaches are also advantageous for quantitative analyses, especially incorporating internal standards. Finally, providing the sample substrate which can be heated increases the range of compounds that act as MAIV matrices spontaneously producing ions from analyte. The use of a laser below the threshold for ionization or ablation of the matrix, or the employment of a gas flow, or gently rubbing the substrate exposed to sub-atmospheric pressure, or ultrasonic vibration of the container, or other means of shaking or vibrating (e.g. piezoelectric) the sample are means of initiating or enhancing MAIV.

BRIEF DESCRIPTION OF DRAWINGS

FIG. 41 illustrates MAIV analyses of Clarithromycin (MW 747) directly from a tablet using the 3-NBN matrix and the AP source.

DETAILED DESCRIPTION OF DISCLOSURE

Figure 1:
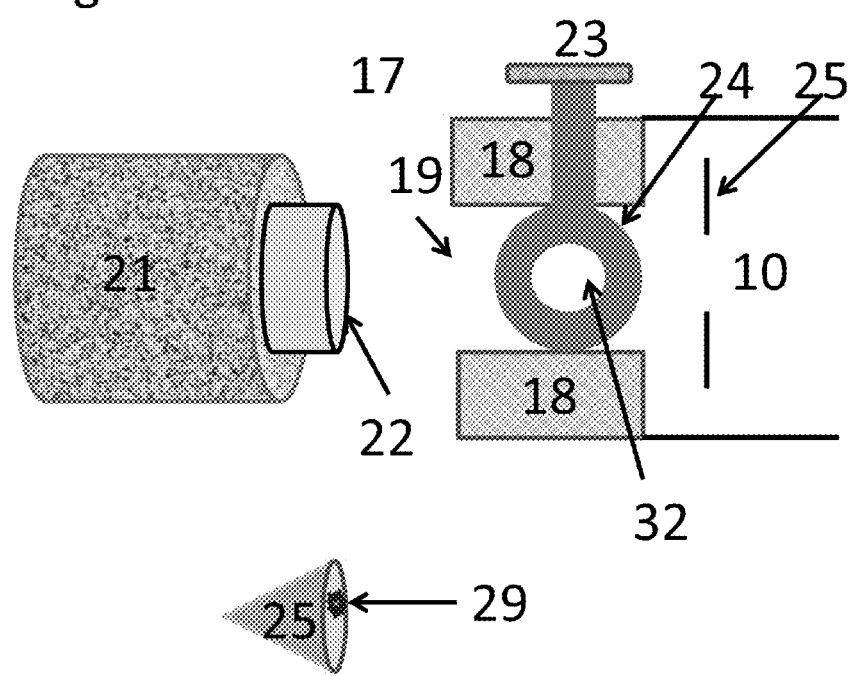
FIG. 1 illustrates an embodiment of a system for introducing the matrix with incorporated analyte, the sample, from a higher to a lower pressure for ionization and analysis of the analyte by MAIV.

In the invention described here, ionization occurs in the sub-atmospheric pressure that can be associated with the ionization region of commercial mass spectrometers such as the commercial or modified inlets (inlet tubes, skimmers, etc.) of an atmospheric pressure ionization source or a vacuum ionization source of a mass spectrometer or ion mobility spectrometer facilitated by an appropriate small molecule matrix such as, but not limited to 3-nitrobenzonitrile (3-NBN), 2-nitrobenzonitrile (2-NBN), 5-methyl-2-nitrobenzonitrile, coumarin, methyl-2-methyl-3-nitrobenzoate, methyl-5-nitro-2-furoate, bronopol (2-bromo-2-nitropropane-1,3-diol), 3-nitrobenzaldehyde, 6-nitro-o-anisonitrile, and phthalic anhydride and certain derivatives thereof. More compounds such as 2,5-DHAP act as MAIV matrices when the sample or the sample substrate are heated. Other means of creating sub-atmospheric pressure to the sample can be used with this method such as a pin-hole leak. Providing means for enhanced evaporation or sublimation of matrix from the gas phase charged particles or droplets produced in the initial spontaneous ionization event can enhance ion formation. Means of providing energy to enhance this desolvation process include heat by such means as radiative as in microwave, IR, visible, or UV radiation, radio frequency fields, gas flow and collisions with gaseous molecules or solid surfaces, and other methods known to those practiced in the art. None of the matrices require a force to propel the matrix: analyte association into enter the gas phase.

Multiply and singly charged ions of volatile and nonvolatile analyte compounds are formed without the need for application of voltages for analyte ionization; the commercial mass spectrometer separates and detects the formed ions according to the mass-to-charge ratio and ion mobility analyzers by the charge, size, and shape of the ion. No lasers are needed, but can be used to provide heat to the sample surface or the substrate onto which the sample is applied to enhance spontaneous ionization and increase the compound types that work as MAIV matrices. Using a laser beam to heat the matrix provides identical results to heating the sample by, for example, heating the substrate. A laser beam provides a means of locally heating a specific area of the sample. Similarly, a gas flow can be used to evaporate the sample gently. Just as heating the sample can extend the compound types that work as MAIV matrices spontaneously producing ions using exposure to sub-atmospheric pressure, preferably between 750 mmHg and $1 \times 10^{-7}$ mmHg, cooling the sample can also extend the method to more volatile compounds acting as MAIV matrices.

The matrix may be mixed with the analyte in a solvent and the sample applied to a substrate for placement at or near the ionization region (e.g., inlet aperture of the atmospheric pressure or the ion extraction element of the intermediate pressure mass spectrometer or ion mobility spectrometer) so long as the sample is at sub-atmospheric pressure. Depending on the MAIV matrix, heat may be applied to the matrix or the substrate onto which it is applied and to the inlet region of the mass spectrometer. The solvents can be the same or different for the matrix and analyte, and the analyte can be in the same solution as the matrix or separate solutions that are mixed before analysis. Salt additives can be used for certain compounds such as but not restricted to synthetic polymers. Buffer conditions can be used for protein-small ligand and protein-protein complexes but are not restricted to these examples. Ammonium salts can be added to the matrix or analyte to reduce chemical background or enhance analyte ion abundance. MAIV operates at low and high pH using a variety of different acids or bases, and at neutral pH. The sample solution can be dried or in solution when introduced against or within a region near the inlet influenced by the low pressure of the instrument. If the sample is introduced in solution the lower pressure conditions and heat aids solvent vaporization and subsequently ionization. Negative and positive mode measurements can be performed according to the preferred analyte structure such that acidic molecules (e.g., fatty acids) preferentially ionize in the negative mode and basic compounds (e.g., hydrophilic peptides, drugs) preferentially ionize in the positive mode. With the MAIV method, the mass range is extended by multiple charging of the analyte for use of low and high performance mass spectrometers with their full capabilities including, but not limited to, accurate mass measurements, high mass resolution measurements, improved ion mobility separation, high efficiency detection using image charge detection, high efficiency fragmentation of multiply charged ions using CID, and high performance fragmentation using ECD and ETD known to those practiced in the art. Small molecules such as drugs, prescription and illicit, and their metabolites, lipids, carbohydrates, triglycerides, proteins and protein-complexes are some analyte examples. Because hot/cold spot issues, limiting MALDI at atmospheric pressure and vacuum, are eliminated and ion production is continuous as in ESI, irreproducibility and quantitation issues are minimized with MAIV, similarly to the continuous ion formation in ESI.

Multiplexing with MAIV exceeds the throughput of direct injection ESI and does not have issues with clogging capillary tubes or the need of heated desolvation gas. In MAIV, less chemical background is observed relative to ESI and MALDI. MAIV is also tolerant to the presence of salts commonly found in biological materials (urine, tissue, whole blood as examples). This method performs well at and near physiological conditions without the need of addition of acid or base, extending the applicability to acid and base labile analytes and chemical and posttranslational modifications.

Cooling of the sample substrate extends the life time of the ion formation process and the applicability to a number of matrices. The sample container outlet to vacuum conditions can be restricted extending the life time of the MAIV ion formation process and a means of capping the containers until ready for ionization offers the ability to multiplex many the samples in a vacuum source similar to vacuum MALDI but without the need of the laser used with MALDI. In case of a well plate array of samples, additionally or alternatively, a film (inexpensive and disposable) can be used to cover the array well plate openings that can be penetrated individually to initiate MAIV ionization and analyses. The lifetime of the signal can also be extended by use of binary matrices for which one of the matrices is a common LSI or MALDI matrix. Examples are adding 2,5-DHB, α-cyano-4-hydroxycinnamic acid (CHCA), or sinapinic acid (SA) to a MAIV matrix in which the MAIV matrix can be as low as 5% of the mixture. By extension, more than two matrices can be mixed so long as one is a MAIV matrix.

Because no additional energy or force is required, MAIV is applicable to fragile molecules such as gangliosides and non-covalent complexes. Gas flow aids in more rapid ionization of the sample provided that sub-atmospheric pressure conditions are maintained and also extends the applicability to more matrices. Gases, collisions with surfaces, and radiofrequency fields downstream from the sample aid in producing higher abundance of the analyte ions, especially with less volatile MAIV matrices and two or more matrices combined with one being a MAIV matrix.

Specificity of analyte ionization can be obtained through suitable matrices and matrix combinations. Temporal resolution is achieved using fast introduction of the sample to the vacuum of the mass spectrometer inlet. Spatial resolution analyses is obtained by miniaturizing the matrix deposition area onto the surface of interested, or by using a pin-hole leak to provide vacuum conditions to a small area of the sample, or a gas flow pointed at the surface or by use of a laser below the matrix/laser threshold to heat a small area of the sample in fluid contact with the sub-atmospheric pressure of the analyzer.

The substrate onto which the matrix is placed may be a variety of materials that do not unduly add to the background or suppress ionization. The substrate may be impervious to surrounding atmosphere, typically air or nitrogen gas, or permeable allowing some flow of gas through the substrate. Typically, with an atmospheric pressure ion source, gas flow aids transfer of ions to the mass analyzer, and thus, some airflow enhances ionization using inlets of API sources. The gas flow can be achieved by use of permeable substrates, imperfect vacuum seals, or by controlled gas leaks. Vacuum ionization sources use voltage to direct ions from the substrate towards the analyzer. Materials for the substrate such as, but not limited to, paper (especially filter paper), metal (plate, foil, or mesh), glass plates or tubes (filled/deposited inside or outside with the sample), synthetic or natural polymers (e.g., well plates, pipet tips), and fibers can be used to introduce the sample to the sub-atmospheric pressure region where ionization commences. Substrates can be materials used for 1- and 2-dimensional separations (paper chromatography, TLC plates, gels (e.g., SDS-PAGE, agarose). The MAIV matrix is deposited manually or sprayed on the surface or deposited directly into the material containing the analyte, the surface affixed to or exposed to the vacuum for MAIV ionization of individual spots, regions or the entire 2-D and 3-D surface of flat or curved objects. Sampling the surface in a systematic fashion, similar to imaging by MS, provides the location of the respective analyte such as a small drug from a dollar bill or a protein from a 1-D gel but without the necessity of a laser while providing spatial and temporal analyses. The analyte to be analyzed can be on a material (e.g., pesticide on a fruit) or part of a material (e.g., active ingredient of a drug directly from a pill (tablet) surface, illicit drugs in hair, mouse brain tissue, living skin or flesh). Some MAIV matrices are natural content of spices (e.g., coumarin) or part of cosmetics (e.g., bronopol).

With MAIV, a variety of means can be employed to achieve rapid and automated analyses. For example, a system can be employed using a metal, polymer, paper, cotton, or fiber ribbon onto which matrix and analyte can be applied by syringe or automatically using an autosampler known to those practiced in the art. The ribbon may be pulled from a roll onto a second roll so that matrix and analyte can be applied separately or together onto the ribbon automatically or by hand, using for example a syringe, placed between the first roll and the instrument inlet. The second roll can be used to pull the ribbon so that it unwinds from the first roll moving the sample across the inlet, exposing the sample deposited continuously or discontinuously, to the vacuum of the mass spectrometer. In this way, multiple analytes are analyzed sequentially as the samples cross the sub-atmospheric region at the mass spectrometer or ion mobility spectrometer inlet aperture. It should be noted that rolls of ribbon are not required nor is it necessary to use a ribbon, as even sheets of, for example, filter paper with the sample applied in a 2-D grid pattern can also be automatically moved, irrespective of the direction and at a desired speed, across the inlet entrance as described above to effect ionization of analyte. In some arrangements, the substrate surface does not have to be in fluid contact with the inlet aperture but sufficiently close to experience the sub-atmospheric pressure in close proximity to the inlet aperture. The gas flowing into the inlet and across the sample, whether by passing through a permeable substrate or by way of a poor vacuum seal of the substrate with the inlet aperture, can be warmed to aid the initial ionization process. Pipet tips (single, or arranged in a line or array) dried, semi-dry, or wet with the sample can be brought near or in fluid contact with the inlet aperture and a robot can be used to automate this process. Again the ionization process is initiated when the sample experiences sub-atmospheric pressure. Similarly, tissue sections and gel sample surfaces can be specifically analyzed using this principle by using a xyz-stage to bring a specific sample area to close proximity or by penetrating the surface layer. Well plates, commonly used for high throughput studies, will also suffice as a substrate. The sample loaded into wells can be allowed to dry and use of a robot or x, y, (z)-stage can move the various wells individually to the ionization region. The mass spectrometer or vacuum ion mobility spectrometer's inlet can be extended with a tube rather than the necessity of bringing the well plate or other surfaces that may be flat to the inlet of the instrument of a modified API inlet as long as the extension head is provided to hold a sufficiently wide area and provide a good enough vacuum seal. Either the well plate can be moved or the inlet tube extension moved so as to have the sample in a well in intimate contact with the inlet or inlet extension. Using, for example, the MAIV matrix 3-NBN eliminates instrument contamination by the matrix because the matrix readily sublimes through exposure to the vacuum of the instrument. The matrix can be pre-applied to a surface such as a ribbon, paper, or well plate in order to simplify the process of loading the sample. With pre-loaded matrix, only a solution of analyte needs to be applied. Analyte concentrations from femtomolar to millimolar can be used routinely with the MAIV method. Cooling the substrate to −80° C. before insertion into the vacuum source area extends the sensitivity into the mid to high attomole range by delaying ionization until the sample is loaded into the proper position for ion transmission.

Application of matrix to a surface using methods for matrix deposition in MALDI and LSI imaging allows images of certain compounds including but not limited to drugs, metabolites, lipids, peptides and proteins administered and endogenous, from chemical surfaces such as catalysts and synthetic polymers, to be obtained using MAIV methods. Example surfaces include films, cell cultures, microbial communities, or tissue sections from certain organs or flesh. For example, moving the surface covered with the MAIV matrix across the inlet aperture to the vacuum region of the instrument produces a low resolution image without the need of a laser. The resolution of the image is related to the diameter of the area exposed to the vacuum by the inlet aperture. Thus, a pin-hole leak will produce a higher resolution image but with lower sensitivity than a larger aperture. Analyses of the composition and composition changes relative to position can be obtained for the entire surface or specifically targeted areas of interest. Simply depositing matrix in a small area of the surface and exposing the surface to sub-atmospheric pressure conditions produces ions only from compounds at the surface exposed to the matrix solution. A resistive heater or gas stream can also be used to locally heat a specific area or array of a surface. A laser can also be employed similar to LSII using a MAIV matrix, but unlike LSII, the laser is used to heat the sample and not for ablation. Mass spectrometers without a heated inlet linking atmospheric pressure and the vacuum of the mass spectrometer can be used for imaging with high spatial resolution using a MAIV matrix and a laser. In this case, the sample may be manipulated at atmospheric pressure or higher pressure, and unlike LSII and MAII, the inlet can be at or near ambient temperature. Alternatively, if the sample is subjected to sub-atmospheric pressure, the laser can be used simply to heat the surface to effect ionization. In this case, infrared lasers are preferred with matrices that do not absorb at the ultraviolet or visible. For imaging, MAIV matrices that require the sample or substrate be heated before spontaneous ionization commences are preferred.

A MAIV matrix in solution using volatile solvents including water when introduced into an inlet tube to the vacuum of a mass spectrometer substantially lowers the temperature required on the inlet tube relative to SAII. By using a Tee adapter, matrix solution can be added to, for example, a LC effluent to enhance ion abundance and the multiple charge states allowing extension of the mass range of analytes such as proteins and large peptides to high performance mass spectrometers with mass range limited capabilities and to enhance fragmentation using CID, ETD, and ECD and variations thereof as well as increase the effectiveness of ion mobility separations on mass and ion mobility spectrometers lacking the application of an heated inlet tube source. The sample can be supplied indirectly using methods common to offline LC-MALDI (solid state from e.g., surfaces or well plates) or online LC-ESI (solution state, from nano and microliter flow) known to those practiced in the art.

Some MAIV matrices (e.g., 3-NBN) can not only produce ions for analysis, but can also be used as an ETD reagent. Thus, a glow discharge is used for producing negative ions of gaseous matrix molecules within the vacuum of the mass spectrometer, usually the first vacuum stage following the inlet. The negative ions of the matrix can be trapped by ion optics such as quadrupole elements within the mass spectrometer and allowed to react with positive ions produced from the analyte in the matrix trapped in the same region. Electron transfer from the negative ions of the ETD reagent to the multiply charged positive analyte ions in the trap cause ETD fragmentation of the positive ions for further analysis which will be obvious to those practiced in the art. The charged ETD reagent gas can be used on mass spectrometers such as the Waters Corporation SYNAPT G2 to perform sequence and posttranslational modification analysis of peptides and proteins. Analyte fragmentation is achieved by switching between cation and reagent anion injection into a trap region of the mass spectrometer; this process can be automated and accomplished within a few hundred milliseconds. The use of this method relative to commonly used ETD methods is that the MAIV matrix is also the ETD reagent eliminating the necessity for a separate apparatus to introduce the ETD reagent. ETD is applicable to vacuum sources (MALDI, EI, CI) through modifications obvious to those trained in the art.

Ion mobility and mass spectrometers with and without coupling the two technologies can be employed with this analyte ionization method such as those used for clinical, homeland security, field portable and hand-held device applications.

FIG. 1 is a representation of one embodiment of a device for introducing the sample to a region of sub-atmospheric pressure where gas phase ions from the analyte are produced without the necessity of a laser, voltage, or any external energy or force applied to the sample of substrate, although energy sources may be useful for certain applications and for use of certain MAIV matrices. In the embodiment shown, a valve (23) separates a higher pressure region (17) from a lower pressure region (10). The higher pressure region 17 may be at atmospheric pressure and the lower pressure region 10 at an intermediate pressure that lies between the higher pressure in region 17 and the vacuum of the analyzer. The valve in one representation is a ball valve with an opening 32 through the ball that, when opening 32 is in the direction shown in the figure, segregates the higher (17) and lower (10) pressure regions so that they are no longer in fluid contact with each other. When probe 21 is inserted into the valve body 18 so that the sample holder 22 inserts into the valve body 18 through channel 19, it provides a sufficient seal so that valve 23 may be turned 90 degrees so that the opening 32 places the sample holder 22 in fluid communication with the lower pressure region 10 without detrimentally raising the pressure in region 10. Turning ball valve 24 so that opening 32 is 90 degrees to the flow of gas from region 17 to region 10, allows removal of probe 22 by blocking the flow of gas without substantially affecting the pressure in region 10. Placing the sample 29 into the substrate 25 and placing the substrate 25 into the substrate holder 22 allows the sample 29 in substrate 25 to be placed into channel 19 using probe 21. Ions from the analyte are formed from the sample when valve 23 is turned 90 degrees so that opening 32 of the valve is aligned so that the sample 29 is in fluid contact with the sub-atmospheric pressure of region 10. Other valve technology that separates a lower from a higher pressure region may be used. The analyte ions produced from sample 29 on being exposed to sub-atmospheric pressure are extracted through opening 32 and accelerated and guided into the mass analyzer using lens elements represented by 25 and know to those practiced in the art. The small gas volume created when probe 21 blocks opening 19 allows valve 23 to be opened without having detrimental impact on the pressure in region 10. In other representations, opening 19 can be larger and the pressure reduced in this region by a separate pumping stage that can be opened and closed by an operator or automatically. The method of sample introduction to vacuum can be manual or automated. By using this method of the sample 29 introduction directly into a vacuum region of a mass spectrometer, ion losses associated with transfer of ions from atmospheric pressure to vacuum are eliminated and the sensitivity of the analysis improved. Sensitivity is also improved using this introduction method because the time that the sample experiences sub-atmospheric pressure to the time analysis begins is short.

Figure 2:
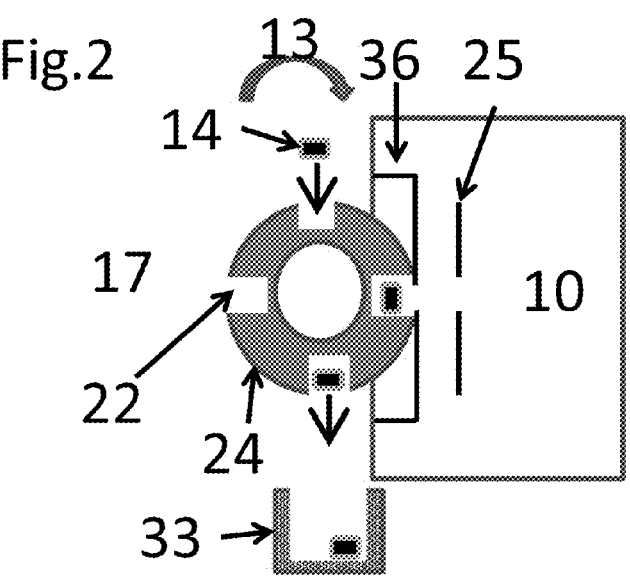
FIG. 2 illustrates another embodiment of a system for introducing the sample from a higher to a lower pressure for analysis using mass spectrometry or ion mobility spectrometry.

FIG. 2 is a representation of another embodiment of a device for introducing the sample to a sub-atmospheric pressure region associated with a mass spectrometer or ion mobility spectrometer for analysis of gas phase ions spontaneously formed from the analyte in the sample when exposed to sub-atmospheric pressure. In this embodiment, 24 represents a vacuum valve within a casing, the casing or body of the valve is not shown for simplicity. The valve can turn as shown by 13 either manually or automatically. In this representation, the valve has four wells 22 that hold substrate 14 into which the sample 29 is placed. It is understood that more or less than four wells may be used. The sample may also be placed directly into the wells rather than onto or into a substrate 14. The valve isolates a higher pressure region 17 from the lower pressure region 10 that is in fluid contact with the vacuum of the analyzer. In this representation, substrate 14 containing the sample 29 is placed in the top well as denoted by the top arrow in the drawing pointed downward. It is understood that other representations not shown are also operational. Turning the valve clockwise, as shown by 13, by 90 degrees places the substrate 14 and sample 29 in fluid contact with the lower pressure region 10. In the embodiment, restriction 36 prevents the substrate from exiting the valve well 22. Once exposed to the sub-atmospheric pressure of region 10, ionization of the analyte commences. The analyte ions, which may be singly or multiply charged, are extracted and guided through lens elements 25 into the analyzer for separation by mass-to-charge (m/z) and fragmentation using mass spectrometry or separation by charge, shape, and size by ion mobility. As shown in the illustration by the lower arrow pointing downward, the substrate that had previously been exposed to vacuum, after turning the valve 90 degrees is in the lower position and falls from well 22 of valve 24 into waste container 33. The empty valve can be rotated to the top position to be filled with another the sample 29. Blanks may be run between samples to assure no carryover between samples. If substrate 14 is not used and the sample 29 is placed directly into well 22, the well 22 to the left and open to region 17 in this embodiment is cleaned while the well to the right in the representation is exposed to vacuum of region 10 of ionization of the sample in that well. This process can be manual or automated.

Figure 3:
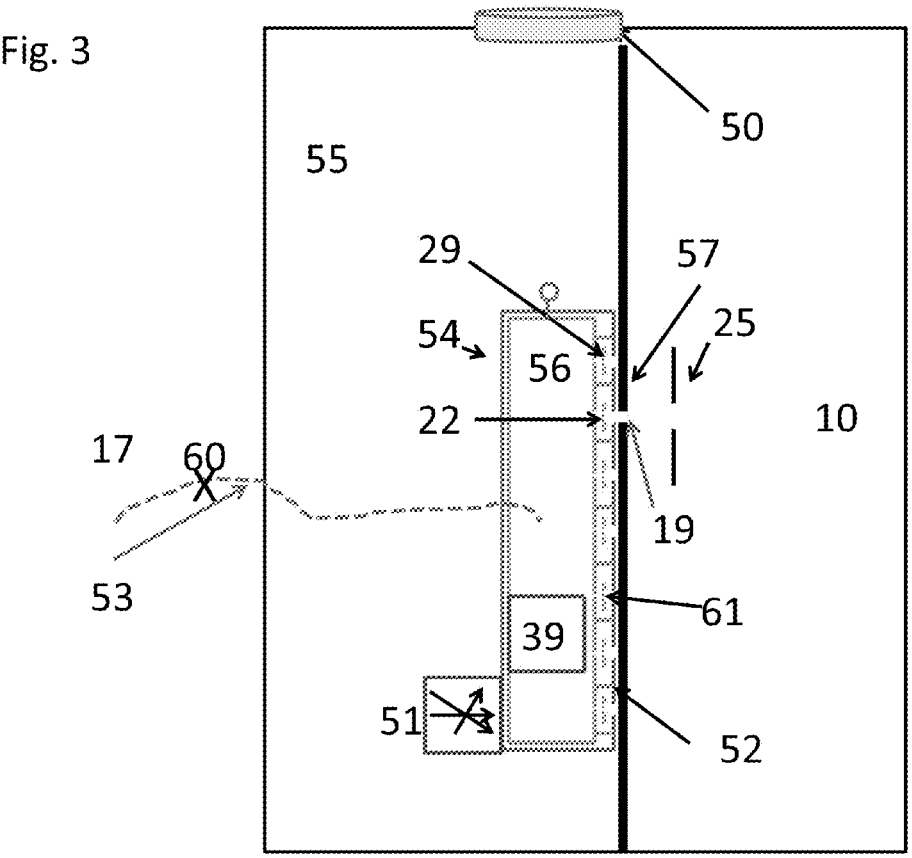
FIG. 3 illustrates another embodiment of a system for introducing multiple the samples individually from a higher pressure region to a lower pressure region for analysis of the analyte incorporated in the MAIV matrix. It should be understood that the multiple samples can be analyzed in rapid sequence or simultaneously through multiple channel. In dual channel mode, the second channel could realize the standard prepared with known concentrations as a MAIV sample.

FIG. 3 is an embodiment of another representation of an arrangement whereby multiple samples can be acquired sequentially using a vacuum source 55 of a mass spectrometer with a vacuum stage entrance 50 similar to those used for introducing the sample stage in MALDI. This arrangement, known to those practiced in the art allows stage 56 to be inserted into the vacuum source chamber 55 and held against the plate 57 that separates region 55 form region 10. Stage 56 fits tightly against plate 57 and may be spring loaded to form a vacuum seal except for a single channel 19 in plate 57 leading to the vacuum region 10 in fluid contact with the lower pressure region of the mass analyzer. Ion extraction lens 25 is directly aligned with channel 19 to extract ions formed from the sample 29 to be into region 10 to be separated by mass-to-charge in the mass analyzer. Chamber 56 can be moved with x, y, z-stage 51 to expose different wells 22 to channel 19 and the vacuum of region 10. In order for each well 22 in stage 56 to be at sufficiently high pressure to minimize sublimation or evaporation of sample 29, the stage is sealed from the vacuum in the source 55 so that the pressure in 56 can be higher than the pressure in region 55. A tube 53 leading from region 17 that may be at atmospheric pressure allows gas to flow into stage 56 controlled by a leak valve 60. The leak is controlled by a valve so that the pressure in 56 is regulated. A capillary channel 61 between stage 56 and well 22 allows sample 29 to be in fluid contact with the pressure of stage 56. Heater 39 in some embodiments is used to heat stage 56 and the sample 29. Using a MALDI sample plate and a MALDI source only a single sample can be loaded into the vacuum for ionization. In this arrangement multiple samples can be loaded into the vacuum source 55 and sealed from the vacuum so that ionization does not occur until the sample 29 is exposed to the vacuum of region 10 by being aligned with channel 19. Each well 22 is separated from every other well. The advantage of exposing the sample to sub-atmospheric pressure of a vacuum ion source is that transferring the ions to the analyzer is more efficient than with atmospheric pressure ion sources. Other embodiments of such an arrangement can be envisioned including an arrangement in which the wells are sufficiently large to hold a section of tissue for analysis by application of a MAIV matrix to the tissue and inserting the stage with tissue into the vacuum source.

Figure 4:
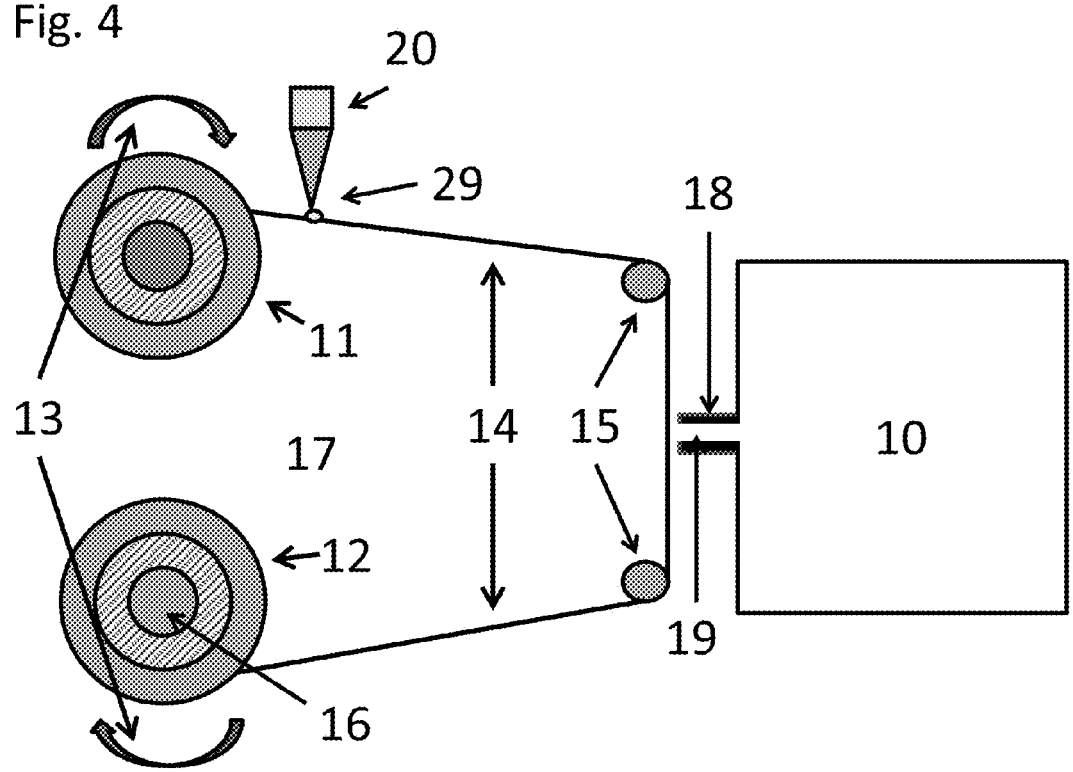
FIG. 4 illustrates another embodiment of a system for automatically or manually introducing the samples from a high pressure region, typically atmospheric pressure, to a sub-atmospheric pressure region for ionization and transfer of the ions to an ion mobility or mass analyzer for analysis.

FIG. 4 is a representation of an embodiment of a method that can be utilized to apply the sample to a substrate, which in some embodiments is a belt or ribbon. The substrate 14 transfers the sample 29 applied to the substrate 14 by device 20 to a sub-atmospheric pressure region 19 for ionization of the analyte and transfer of the ions into a mass or ion mobility analyzer for analysis of the analyte. In this embodiment, a higher pressure region 17, which in some embodiments is at atmospheric pressure, is in fluid contact with a lower pressure region, which in some embodiments is the first vacuum stage of an analyzer, by an inlet 18 with channel 19. The channel 19 of inlet 18 provides fluid contact of regions 17 and 10 and in some embodiments is the inlet of an atmospheric pressure ionization mass spectrometer or ion mobility spectrometer and in some embodiment is a skimmer cone or a tube inlet. In some embodiments the channel of inlet 18 is sufficiently large that it transmits more gas from region 17 to region 10 than the pumping system of the ion mobility or mass analyzer can tolerate when substrate 14 is not covering channel 19 of inlet 18. In such an embodiment, a valve can be inserted into inlet 18 to restrict gas flow when substrate 14 is not covering channel 19. Alternatively, the channel 19 of inlet 18 can be made sufficiently small that the analyzer is operational when the inlet is not covered by the substrate 14 as is common with inlets of atmospheric pressure mass spectrometers.

In one embodiment of the method describe here, a spindle 11 holds a substrate 14, which is one embodiments is a ribbon. The substrate 14 in some embodiments is made from paper, especially filter paper, fabric, polymer, plastic, metal, or other material that does not contribute substantially to the ions observed by the analyzer. The substrate 14 is pulled over rollers 15 and onto spindle 12. The spindle 11 in some embodiments is spring loaded to keep substrate 14 tight between spindles 11 and 12. Spindle 12 turns in direction 13 to pull the substrate 14 from spindle 11 over rollers 15 and onto spindle 12. Axel 16 in some embodiments is attached to a motor drive to turn spindle 12. Device 20, which in some embodiments is a pipette tip, loads the sample onto ribbon 14 while the ribbon is moving from spindle 11 to spindle 12. In another embodiment device 20 is an autosampler known to those practiced in the art and is used to introduce analyte in solution to the substrate 14. In such an arrangement, a second device 20, either before or after the autosampler, applies the MAIV matrix in a solvent to the substrate 14 using, for example, a syringe pump. The entire assembly is positioned so that the substrate 14 moves across channel 19 of inlet 18 so that the substrate 14 is either in direct contact with channel 19 of inlet 18 or in very close proximity to channel 19 of inlet 18. The sample applied to substrate 14 from a solution by device 20 dries as the sample moves toward inlet 18. When the sample experiences the vacuum at channel 19, ions are formed from the analyte in the sample 29. In this representation, substrate 14 is gas permeable. A heated gas flow (not shown) is directed in a narrow diameter stream at substrate 14 in close proximity to the inlet channel 19 of inlet 18. By heating the substrate 14 or the sample 29, ionization may be enhanced. In one embodiment, inlet 18 is heated to enhance evaporation of sublimation of the matrix. The movement of the substrate 14 and application of the sample 29 to the ribbon in one embodiment is automated.

Figure 5:
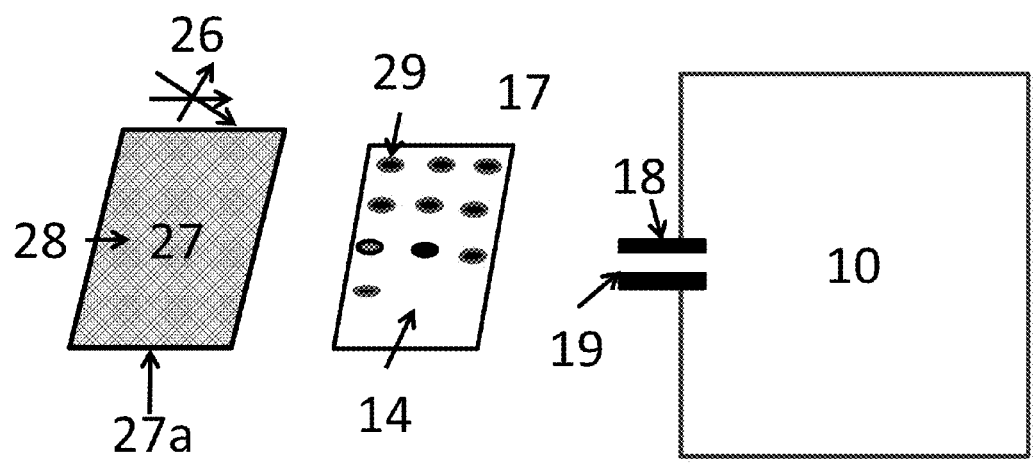
FIG. 5 illustrates another embodiment of a system for automatically or manually introducing the sample to sub-atmospheric pressure to initiate ionization.

FIG. 5 is a representation of an embodiment of another method for obtaining rapid and automated analyses of the sample using the MAIV method. Inlet 18 with opening 19 provides fluid communication between a higher pressure region 17 and a lower pressure region 10. The higher pressure region in some embodiments is at atmospheric pressure and the lower pressure region 10 is in fluid communication with the vacuum of the mass analyzer or ion mobility analyzer. Plate 27 has a frame 27a that holds a mesh or screen 28 which is gas permeable. Substrate 14 in one embodiment is filter paper onto which the sample 29 is loaded, typically using 1 or a few microliters of the sample 29 in a solvent. Substrate 14 is affixed to plate 27 so that it partially or entirely covers screen or mesh 28. The assembled device is attached to a stage that moves plate 27 with substrate 14 held close to or in interment contact with channel 19 of inlet 18 in two or three directions as is common using xy- and xyz-stages used with microscopy. The plate 27 with substrate 14, having the samples 29 applied, is placed perpendicular to inlet 18 and either touching inlet 18 so as to cover opening 19 or very nearly touching inlet 18. In the case where the substrate 14 does not physically touch inlet 18, it must be sufficiently close to the entrance to channel 19 to create a sub-atmospheric pressure environment for the sample 19 when it and inlet 19 are close proximity with one another. When the sample 19 experiences a lower pressure than in region 17, due to the influence of region 10 through inlet opening 19, the sample 29 produces gas phase ions from the analyte for analysis in the analyzer. Plate 27 can be moved using an xy- or xyz-stage 26 to sequentially expose each the samples 29 to sub-atmospheric pressure to produce analyte ions for analysis. This process in some embodiments is automated similar to matrix assisted laser desorption, but here the plate 27, substrate 14, and the sample 29 in some embodiments is at atmospheric pressure rather than vacuum. Gas blown through a heated tube (not shown) of diameter similar to the diameter of the sample spots applied to the substrate can be used to enhance ionization with some matrix materials. Likewise, heating inlet 18 can enhance the MAIV process when using certain MAIV matrices.

Figure 6:
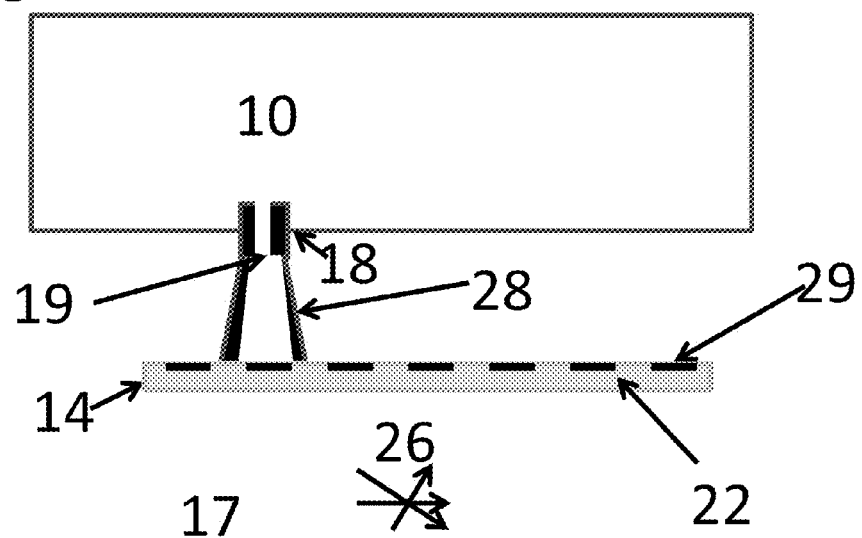
FIG. 6 illustrates another embodiment of the system represented in FIG. 5.

FIG. 6 is yet another representation of an embodiment of a method to introduce the sample 29 to sub-atmospheric pressure from a high pressure region 17, typically at atmospheric pressure for ionization of the analyte and analysis by mass spectrometry or ion mobility spectrometry. In this embodiment, inlet 18 with channel 19 provide fluid communication between a higher pressure region 17 and a lower pressure region 10 similar to FIG. 5. The inlet 18 has an extension 28 which extends channel 19 so that it flares into a cone with a larger opening to region 17. Substrate 14 with the sample 29 is manipulated using x, y-stage 26 to sequentially move the samples 29 so that they are in intermit contact with channel 19 of extension 28. In one embodiment, the sample 29 is placed in wells 22 in substrate 14. The exit of channel 19 to region 17 has a larger diameter than the diameter of the wells 22 of the substrate 14 so that the wells 22 and the sample 29 are in fluid contact with the low pressure region 10 of an analyzer when the wells 22 and the channel 19 are perfectly aligned so that the sample 29 is at sub-atmospheric pressure and analyte ions are formed. The gas leak through the well 22 when not precisely aligned with channel 19 aids in transferring the analyte ions into the analyzer for analysis. This method is some embodiments is automated and controlled by a computer.

Figure 7:
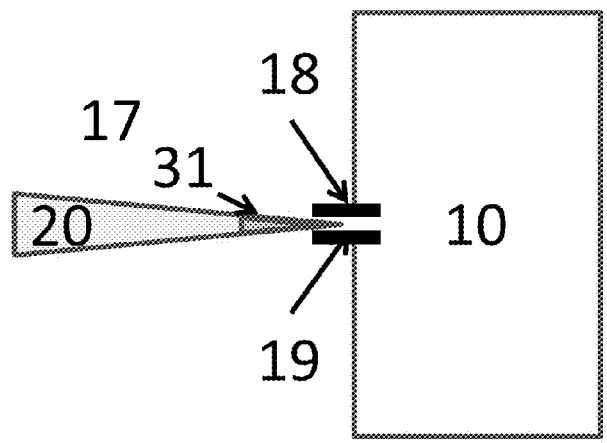
FIG. 7 illustrates another embodiment of a system for introducing the MAIV matrix and analyte, the sample, in solution to a sub-atmospheric pressure region to initiate ionization.

FIG. 7 is another representation of an embodiment of a method for ionizing the sample using the MAIV method. In this representation, the sample 29 composed of a MAIV matrix and analyte in solution is introduced directly into opening 19 of inlet 18 using, for example, a pipette 20 with solution 31 containing the sample 29. Addition of a MAIV matrix to the solution substantially reduces the temperature required for inlet 18 to produce ions of the analyte relative to solvent assisted inlet ionization, SAII, which uses a solvent without added matrix. Thus, abundant ions can be produced from both skimmer and tube inlets below 150° C., a temperature in which SAII does not produce ions in a skimmer inlet and produces analyte ions in low abundance in a tube inlet. In some embodiments, this method is automated.

Figure 8:
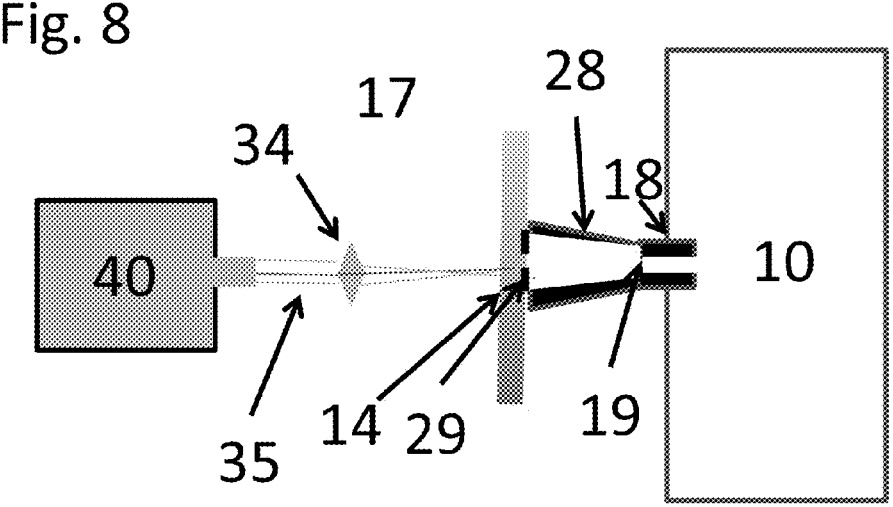
FIG. 8 illustrates another embodiment of a system in which a laser is used to heat a small area of the sample to aid ionization by the MAIV method.

FIG. 8 is another representation of an embodiment demonstrating how the MAIV ionization method can be used in conjunction with a laser. Although the representation is of an atmospheric pressure ionization inlet, this approach also is operational with a vacuum source. Shown in the embodiment in FIG. 8 is a higher pressure region 17 and a lower pressure region 10 in fluid communication with each other through channel 19 of and extension 28 of inlet 18. Extension 28 with conical opening of channel 19 into region 17 provides a larger area to cover sample 29 on substrate 14. Substrate 14 is one embodiment is a glass microscope slide which is transparent to the laser beam 35 from the laser 40. Placing the substrate 14 against the conical extension 28 produces an imperfect seal between 28 and 14 exposing the sample 29 to a pressure lower than in region 17. By using a matrix such as 2,5-DHAP which needs to be warmed to act as a MAIV matrix, a laser can be used to heat the matrix in the localized area by transmitting the laser beam through a focusing lens 34 so that it focuses on the sample 29. The area of the sample heated by absorption of the laser energy produces analyte ions. By rastering the laser beam across the sample while acquiring mass spectra, images of the location of compounds in the sample 29 can be obtained using imaging software. The sample in some embodiments is a section of biological tissue.

Figure 9:
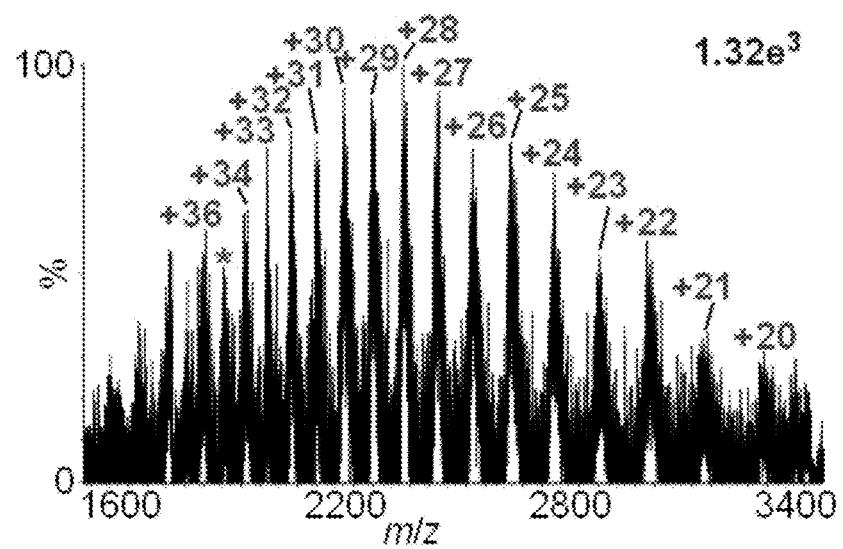
FIG. 9 illustrates the MAIV mass spectrum of bovine serum albumin (BSA) (Molecular weight [MW] ~66000) using the vacuum MALDI source, hereafter the vacuum source, of a Waters SYNAPT G2 ion mobility spectrometry (IMS) mass spectrometry (MS) instrument without the laser and using 3-NBN as the matrix.

FIG. 9 illustrates the MAIV mass spectrum of bovine serum albumin (BSA) (Molecular weight [MW] ~66000) using the vacuum MALDI source, hereafter the vacuum source, of a Waters SYNAPT G2 ion mobility spectrometry (IMS) mass spectrometry (MS) instrument without the laser and using 3-NBN as the matrix.

Figure 10:
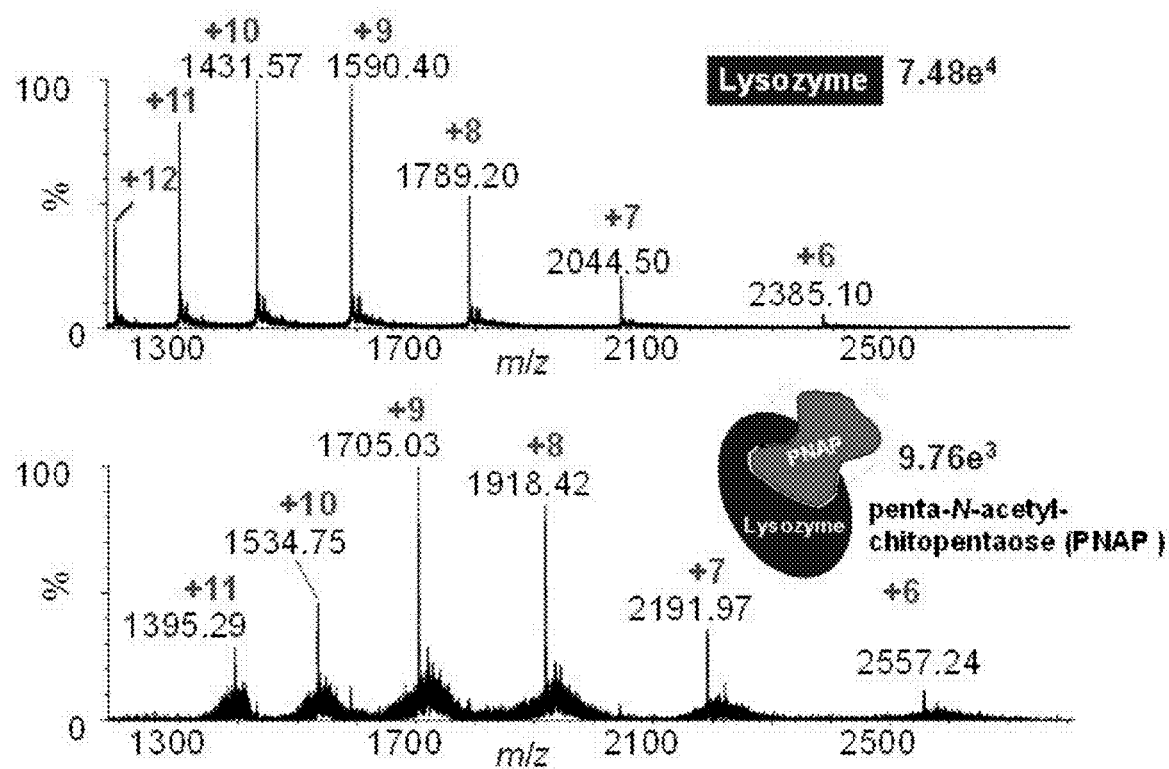
FIG. 10 (top) illustrates MAIV of lysozyme (MW 14300) and (bottom) its complex with a small peptide (PNAP) analyzed from buffered solution using 3-NBN as matrix on the vacuum source.

FIG. 10 (top) illustrates MAIV of lysozyme (MW 14300) and (bottom) its complex with a small peptide (PNAP) analyzed from buffered solution using 3-NBN as matrix on the vacuum source.

Figure 11:
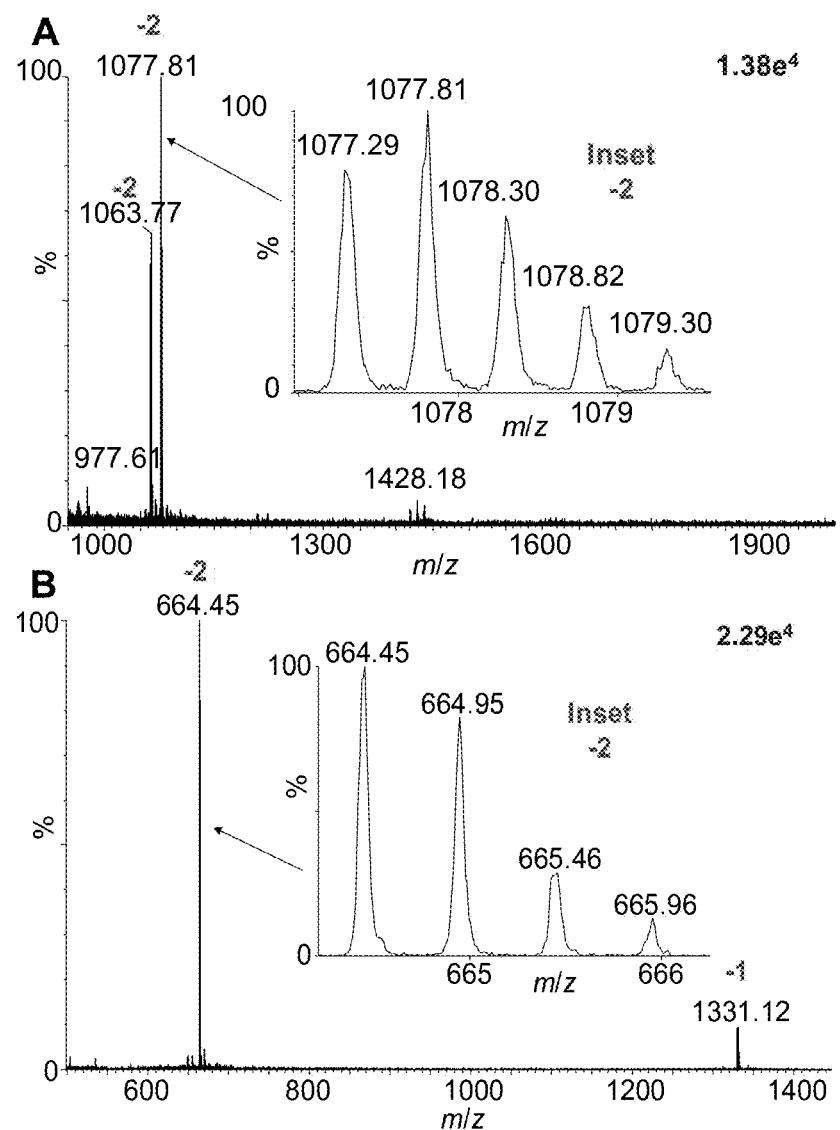
FIG. 11 illustrates MAIV of the fragile non volatile compounds: (top) GT1b gangliosides (MW 2128 and 2156) and (bottom) a phosphorylated peptide (MW 1332) using the vacuum source and negative mode detection.

FIG. 11 illustrates MAIV of the fragile non volatile compounds: (top) GT1b gangliosides (MW 2128 and 2156) and (bottom) a phosphorylated peptide (MW 1332) using the vacuum source and negative mode detection.

Figure 12:
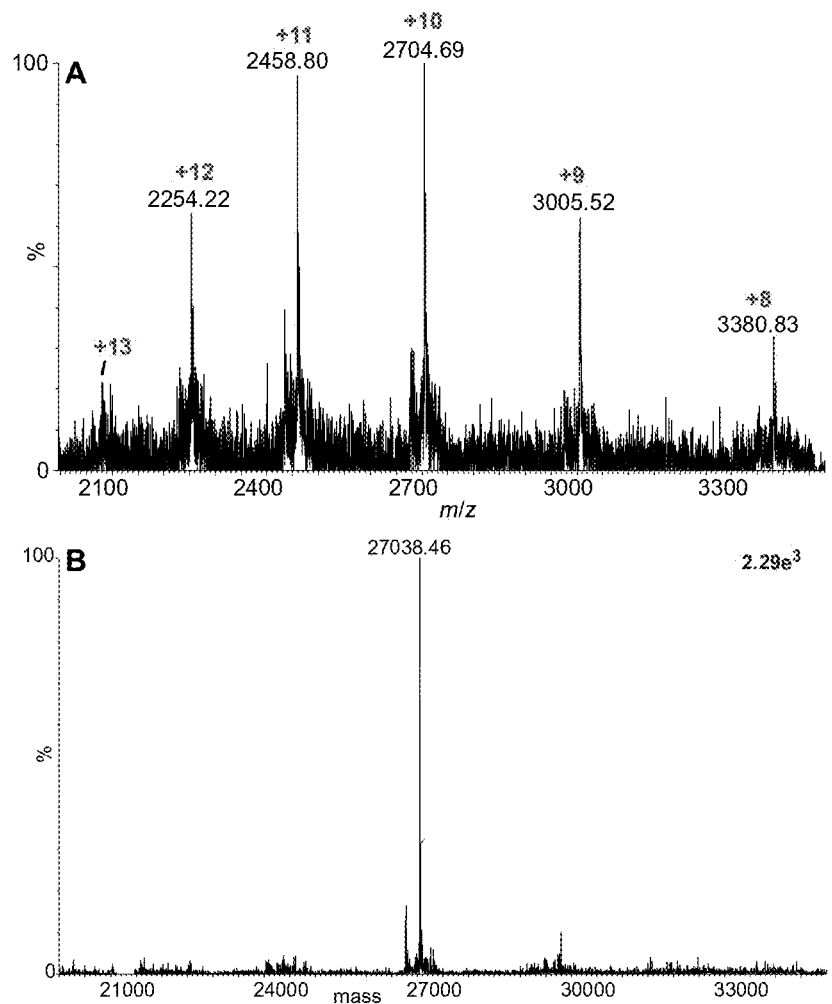
FIG. 12 illustrates MAIV of the membrane protein bacteriorhodopsin (MW ~27000) 3-NBN as matrix using the vacuum source. Multiply charged ions are observed (top).

FIG. 12 illustrates MAIV of the membrane protein bacteriorhodopsin (MW ~27000) 3-NBN as matrix using the vacuum source. Multiply charged ions are observed (top). It should be understood that deconvolution programs can be used as is exemplified in the bottom mass spectrum.

Figure 13:
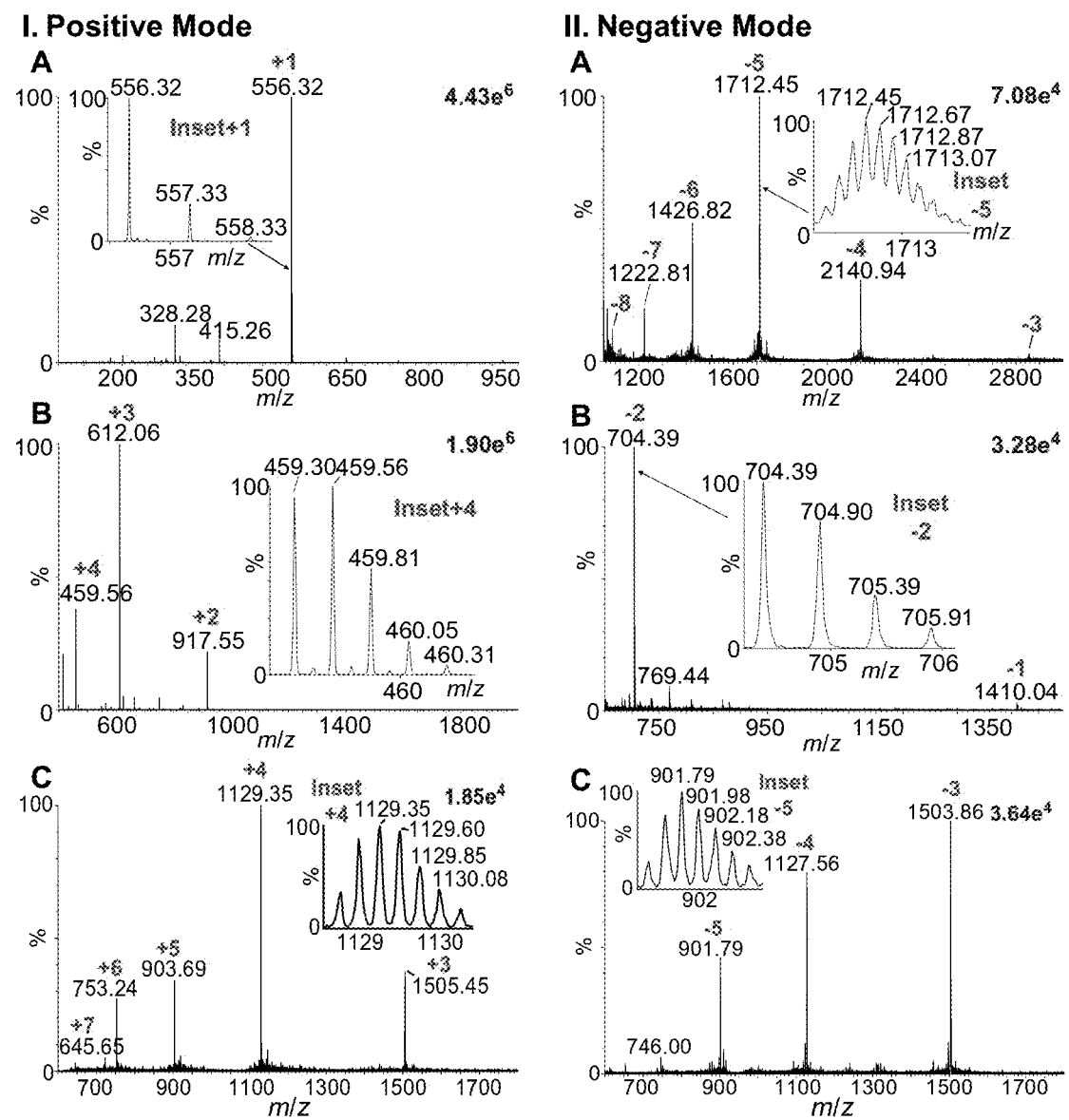
FIG. 13 illustrates MAIV of a variety of analytes using the vacuum source.

FIG. 13 illustrates MAIV of a variety of analytes using the vacuum source. The left panel shows the positive and the right panel the negative mode measurements using 3-NBN as the matrix.

Figure 14:
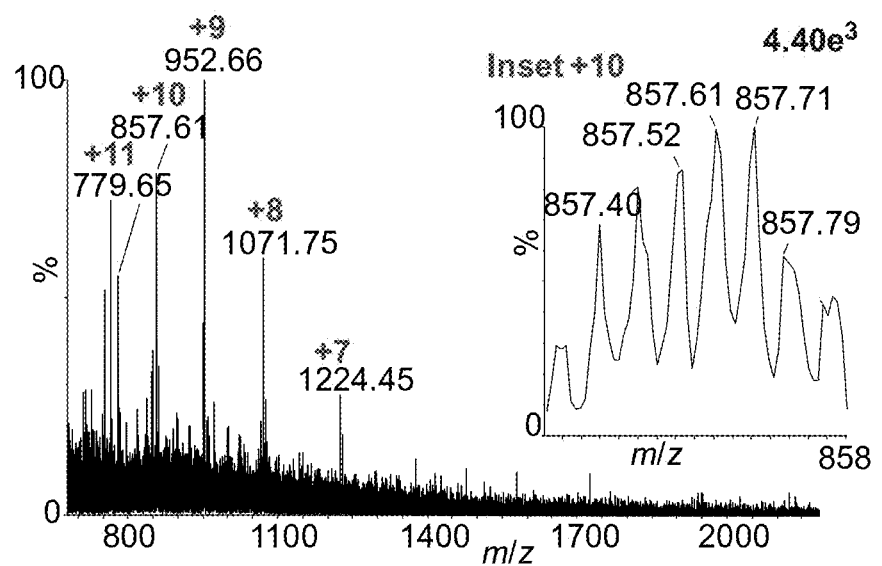
FIG. 14 illustrates MAIV using the vacuum source with 3-NBN as the matrix and 50 fmol of ubiquitin. The inset illustrates the isotopic distribution of charge state +10 of ubiquitin.

FIG. 14 illustrates MAIV using the vacuum source with 3-NBN as the matrix and 50 fmol of ubiquitin. The inset illustrates the isotopic distribution of charge state +10 of ubiquitin.

Figure 15:
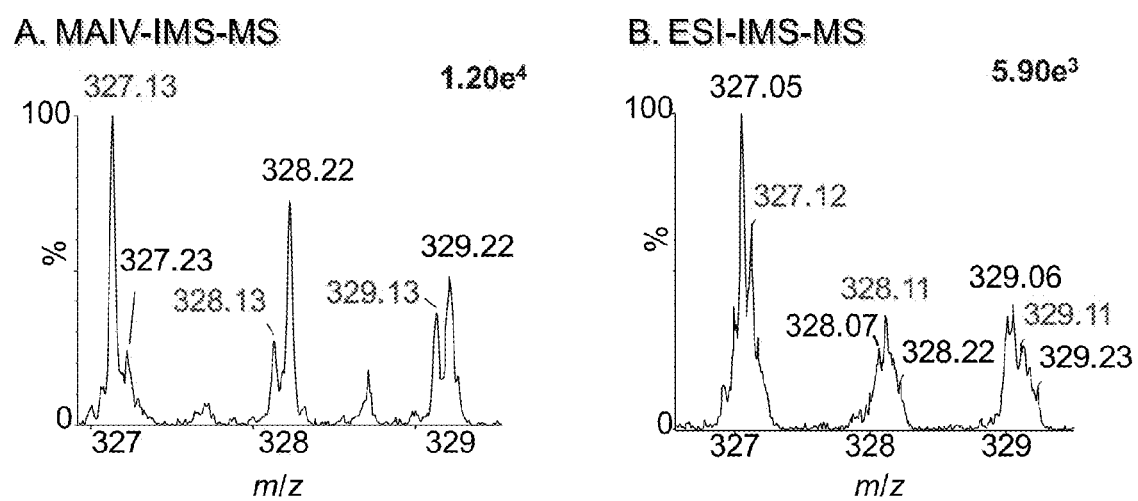
FIG. 15 illustrates analyses of 5 femtomoles of clozapine. The left panel is the MAIV results using 3-NBN as matrix on the vacuum source and the right panel using ESI.

FIG. 15 illustrates analyses of 5 femtomoles of clozapine. The left panel is the MAIV results using 3-NBN as matrix on the vacuum source and the right panel using ESI.

Figure 16:
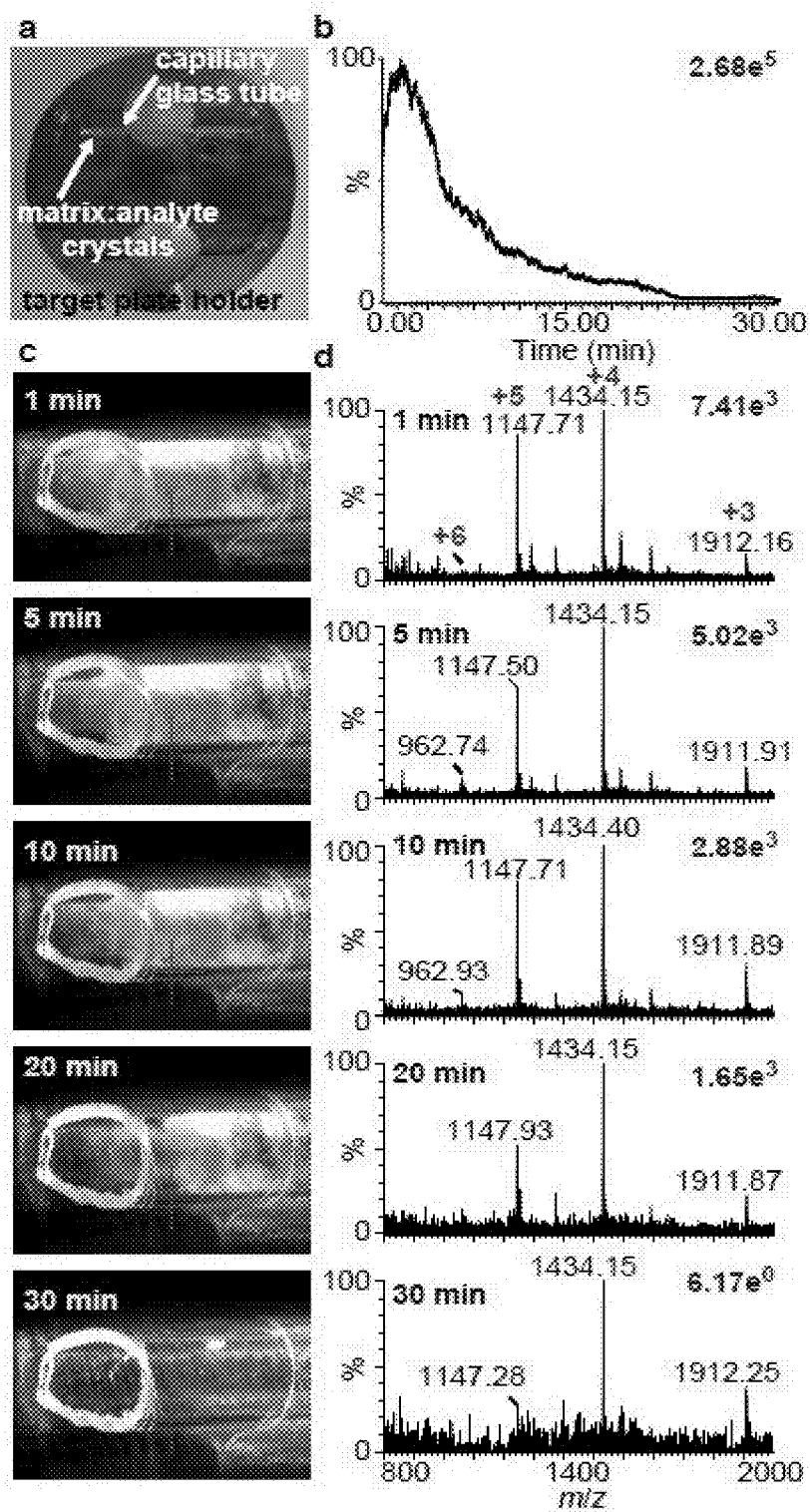
FIG. 16 illustrates MAIV using 3-NBN as matrix on the vacuum source using a capillary as the substrate into which the sample was dried to prolong ionization.

FIG. 16 illustrates MAIV using 3-NBN as matrix on the vacuum source using a capillary as the substrate into which the sample was dried to prolong ionization. Ionization is extended from about 1 minute when the 3-NBN matrix is applied to a traditional MALDI target plate to about 30 minutes in the capillary.

Figure 17:
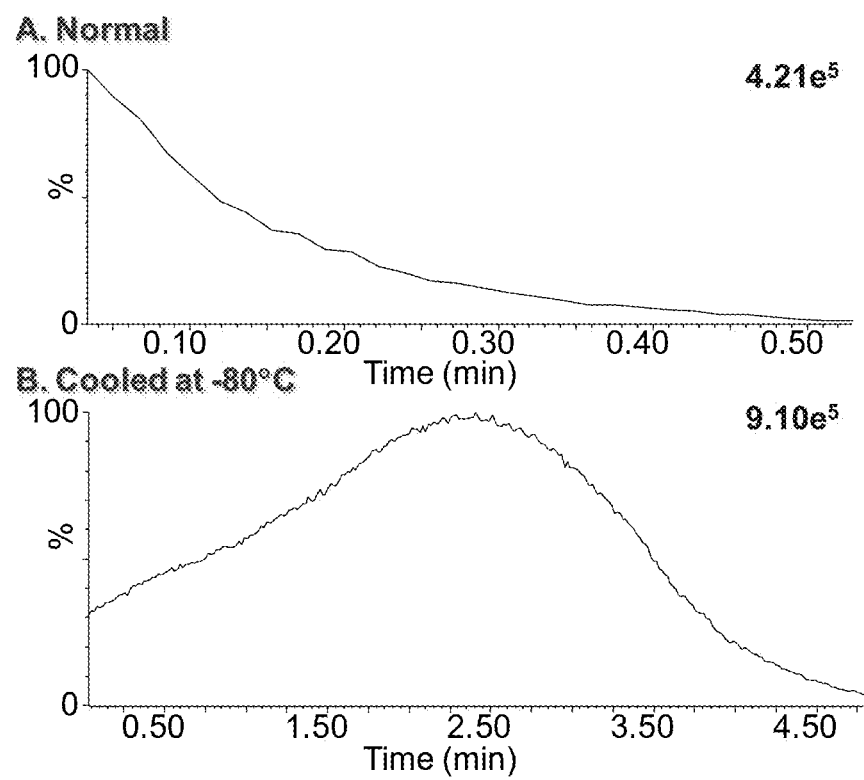
FIG. 17 illustrates another method for extending the time of ionization using 3-NBN with vacuum source MAIV.

FIG. 17 illustrates another method for extending the time of ionization using 3-NBN with vacuum source MAIV. The left panel illustrates the total ion chronograms and the right panel the mass spectra. The top row was obtained when the substrate was loaded into the vacuum source at room temperature and the bottom row illustrates when the substrate (metal) was cooled to −80° C. and immediately introduced to the vacuum source. Ionization is extended from about 1 minute to 11 minutes.

Figure 18:
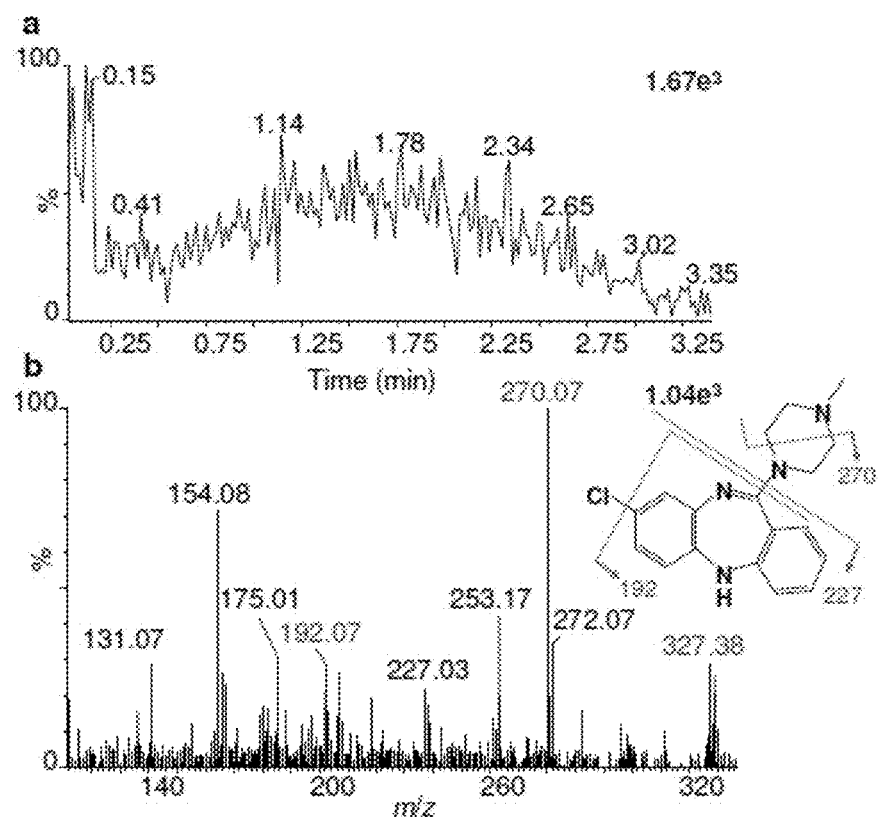
FIG. 18 illustrates MAIV using the vacuum source and the substrate at −80° C. to obtain the MS/MS spectrum of clozapine (MW 328) at 900 attomoles deposited on the metal plate.

FIG. 18 illustrates MAIV using the vacuum source and the substrate at −80° C. to obtain the MS/MS spectrum of clozapine (MW 328) at 900 attomoles deposited on the metal plate.

Figure 19:
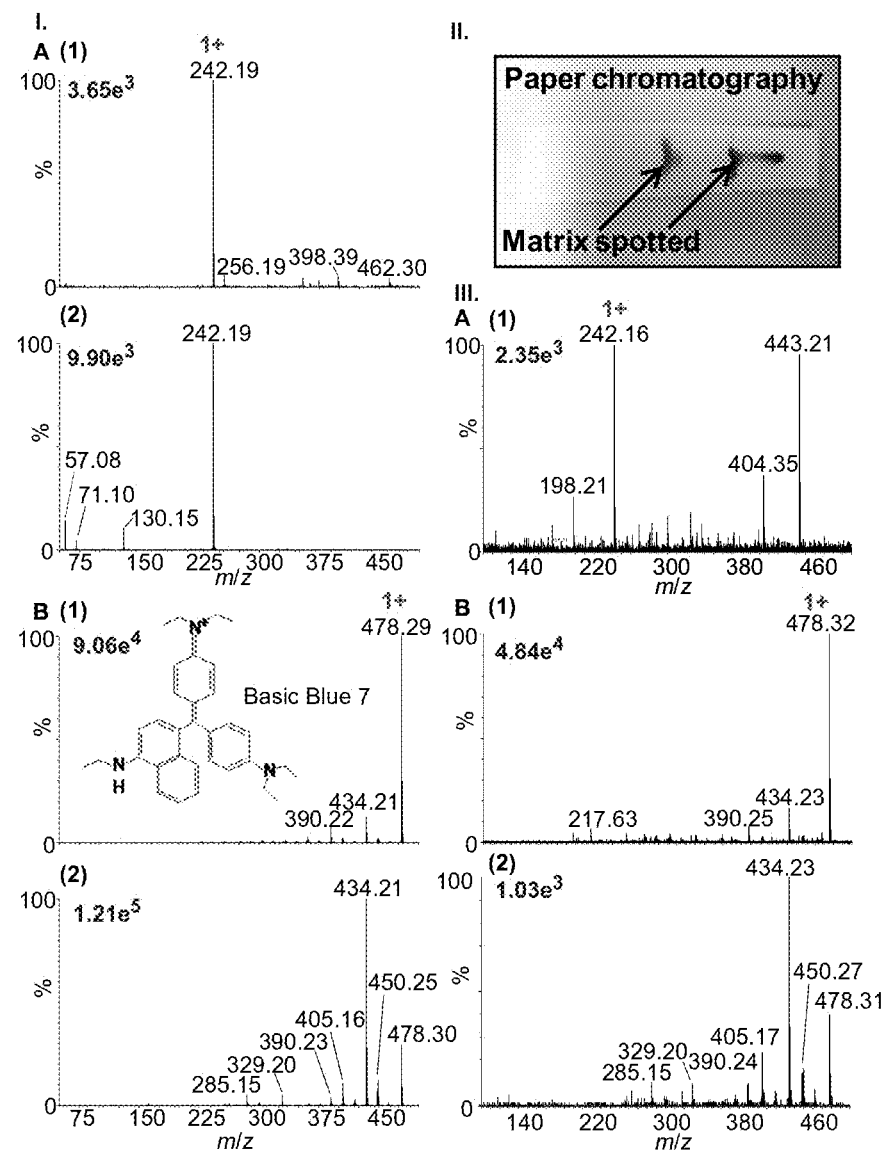
FIG. 19 illustrates MAIV mass spectra using the ESI source and the matrix 3-NBN and paper chromatography to separate compounds in a marker pen.

FIG. 19 illustrates MAIV mass spectra using the ESI source and the matrix 3-NBN and paper chromatography to separate compounds in a marker pen: (1) MS and (2) MS/MS of (A) red and (B) blue ink marked on filter paper with 3-NBN; (I) analyzed as individual spots, (II) photograph of the filter paper after separation of the two inks, and (III) analysis after separation: (1) MS and (2) MS/MS.

Figure 20:
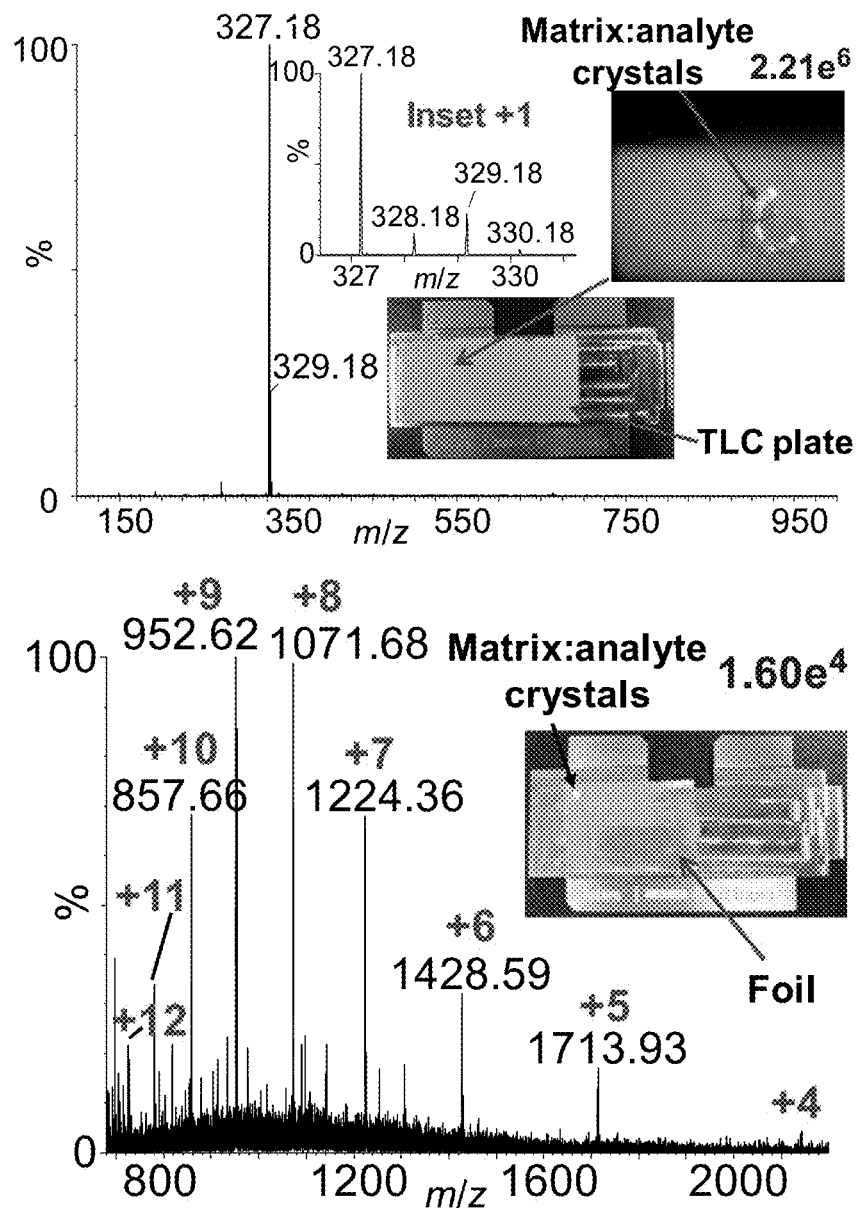
FIG. 20 illustrates MAIV from (top) a thin layer chromatography (TLC) plate and (bottom) a metal foil using the vacuum source and 3-NBN as matrix.

FIG. 20 illustrates MAIV from (top) a thin layer chromatography (TLC) plate and (bottom) a metal foil using the vacuum source and 3-NBN as matrix.

Figure 21:
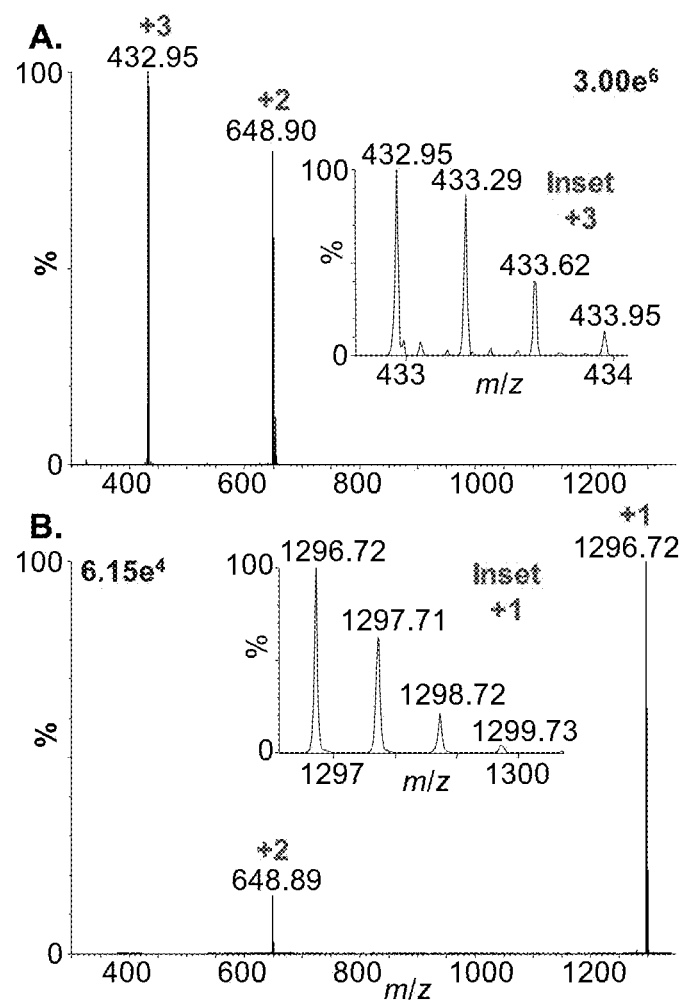
FIG. 21 illustrates MAIV of a peptide using 3-NBN as matrix and the vacuum source.

FIG. 21 illustrates MAIV of a peptide using 3-NBN as matrix and the vacuum source. (top) low voltages applied and (bottom) extraction voltages applied in the vacuum source.

Figure 22:
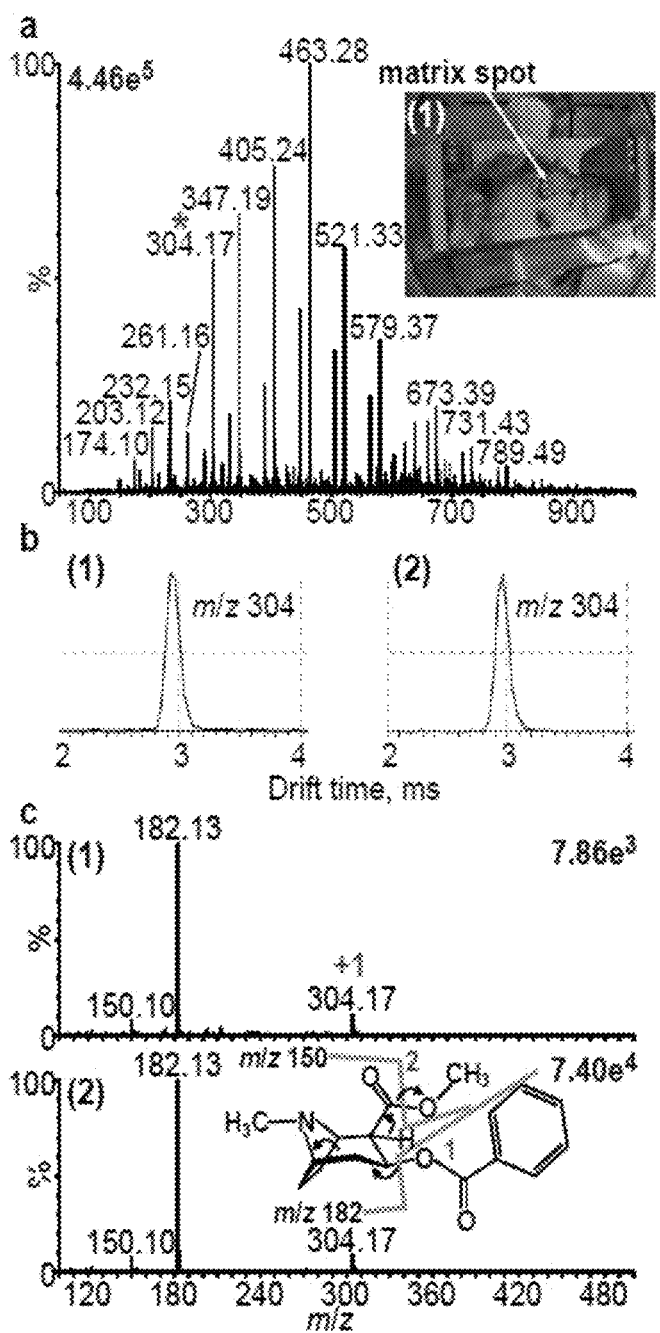
FIG. 22 illustrates MAIV applying the matrix 3-NBN to a small area of a 20 dollar bill using the vacuum source.

FIG. 22 illustrates MAIV applying the matrix 3-NBN to a small area of a 20 dollar bill using the vacuum source. Only the one eye of the President was marked with the matrix and analyzed by IMS-MS and MS/MS identifying a polymer (PPG) and the presence of cocaine. This exemplifies the sensitivity and spatial analyses of the MAIV method.

Figure 23:
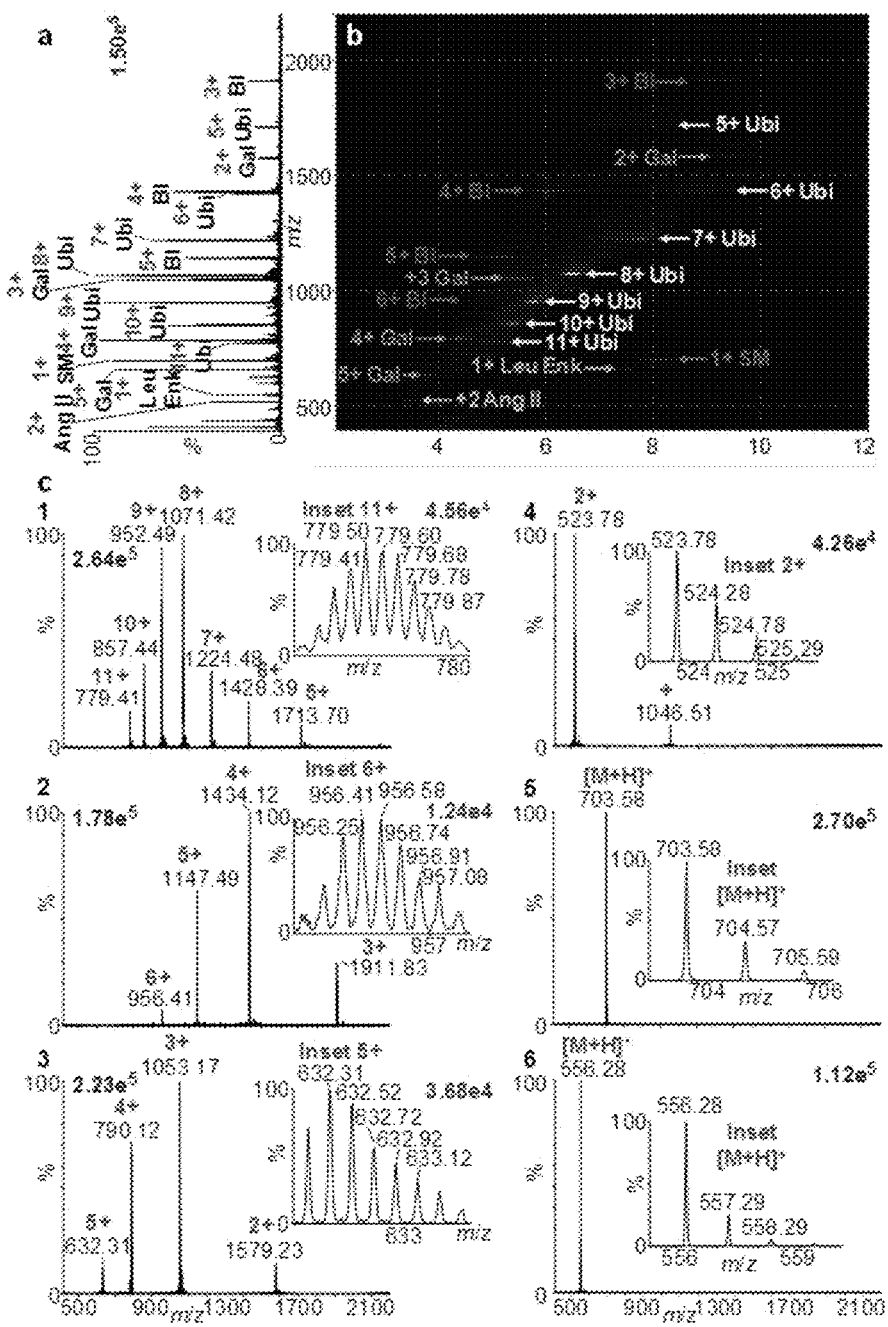
FIG. 23 illustrates MAIV using the vacuum source and 3-NBN as matrix. Ions are instantaneously formed and separated as well as detected (IMS-MS).

FIG. 23 illustrates MAIV using the vacuum source and 3-NBN as matrix. Ions are instantaneously formed and separated as well as detected (IMS-MS). Charge states fall into families and detailed information can be extracted (drift times, m/z). For example, the mass spectra of all 6 components in the mixture of small drugs to proteins are obtained with little interference from each other.

Figure 24:
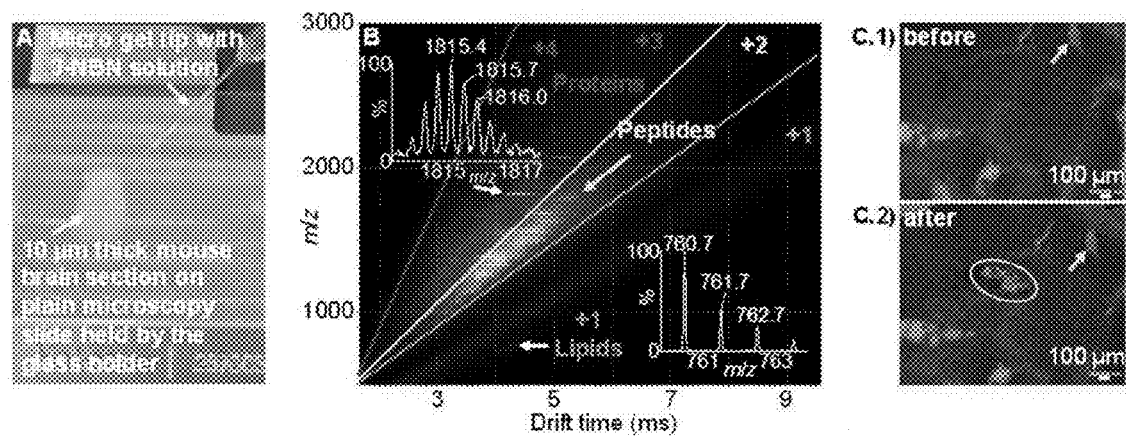
FIG. 24 illustrates the MAIV mass spectra of a delipified tissue section using the 3-NBN matrix and the vacuum source.

FIG. 24 illustrates the MAIV mass spectra of a delipified tissue section using the 3-NBN matrix and the vacuum source. The left panel shows a picture of deposition of the matrix using a micropipette, the IMS-MS 2-D plot with inset mass spectra and indication of the respective charge state families and the right panel shows tissue (top) before and (bottom) after MAIV-IMS-MS analyses providing spatial analyses.

Figure 25:
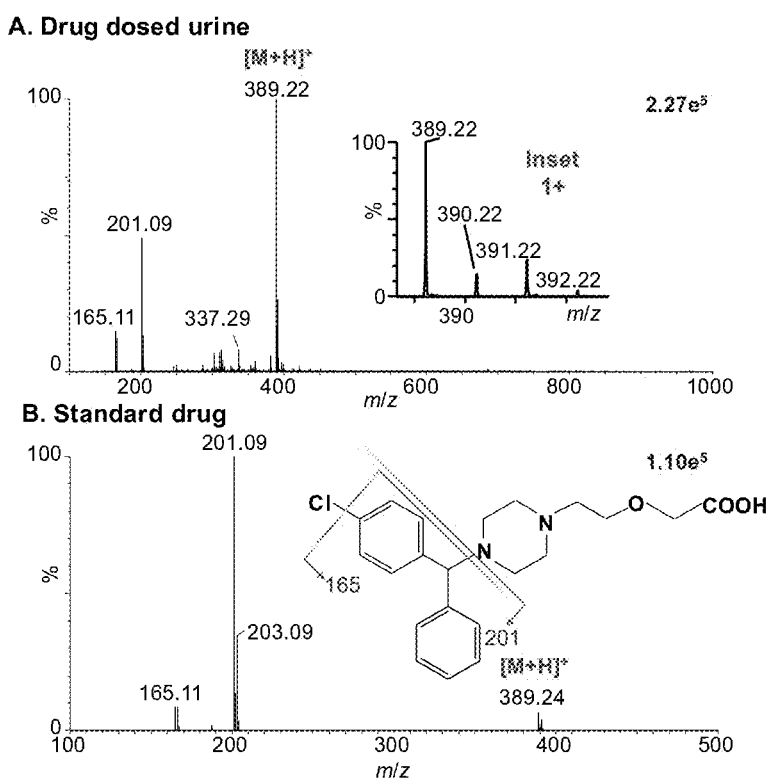
FIG. 25 illustrates MAIV of drug dosed urine characterizing Cetirizine (MW 388) using the vacuum source and 3-NBN as the MAIV matrix (metal plate substrate).

FIG. 25 illustrates MAIV of drug dosed urine characterizing Cetirizine (MW 388) using the vacuum source and 3-NBN as the MAIV matrix (metal plate substrate). Top: mass spectrum and bottom MS/MS (CID) fragment spectrum. It should be understood that in-source fragmentation can be used for certain applications.

Figure 26:
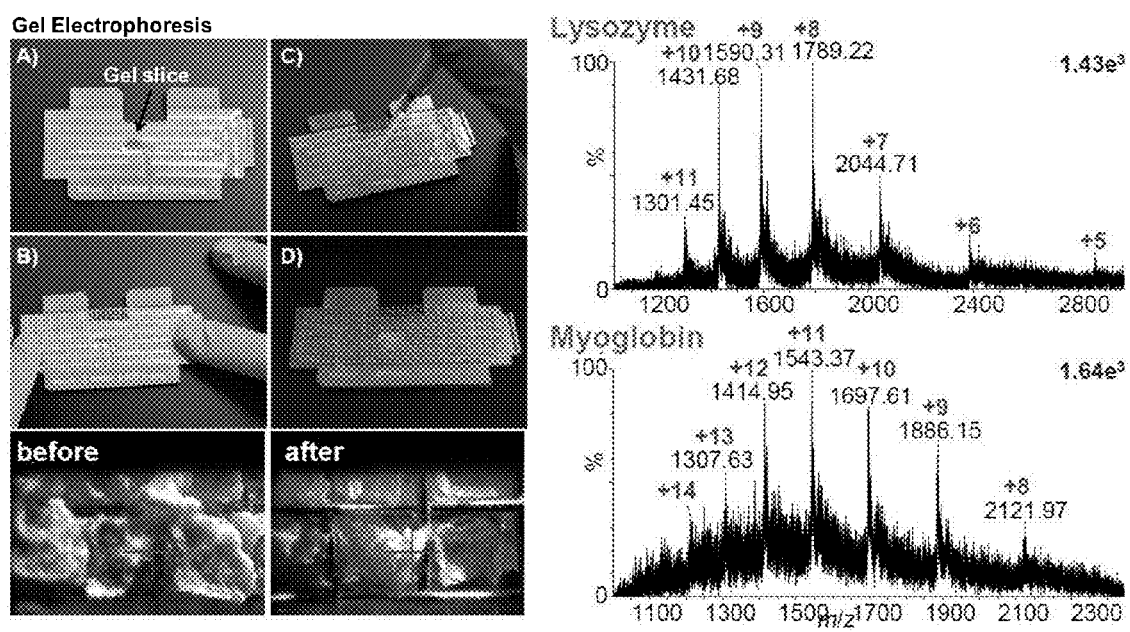
FIG. 26 illustrates MAIV of 1-D gel (gel slices analyzed after gel electrophoresis) using the vacuum source.

FIG. 26 illustrates MAIV of 1-D gel (gel slices analyzed after gel electrophoresis) using the vacuum source. After gel separation, the gel piece is adhered to the plate through a mesh and the matrix pipetted into the gel for extraction of the protein out of the gel and direct protein analyses by IMS-MS.

Figure 27:
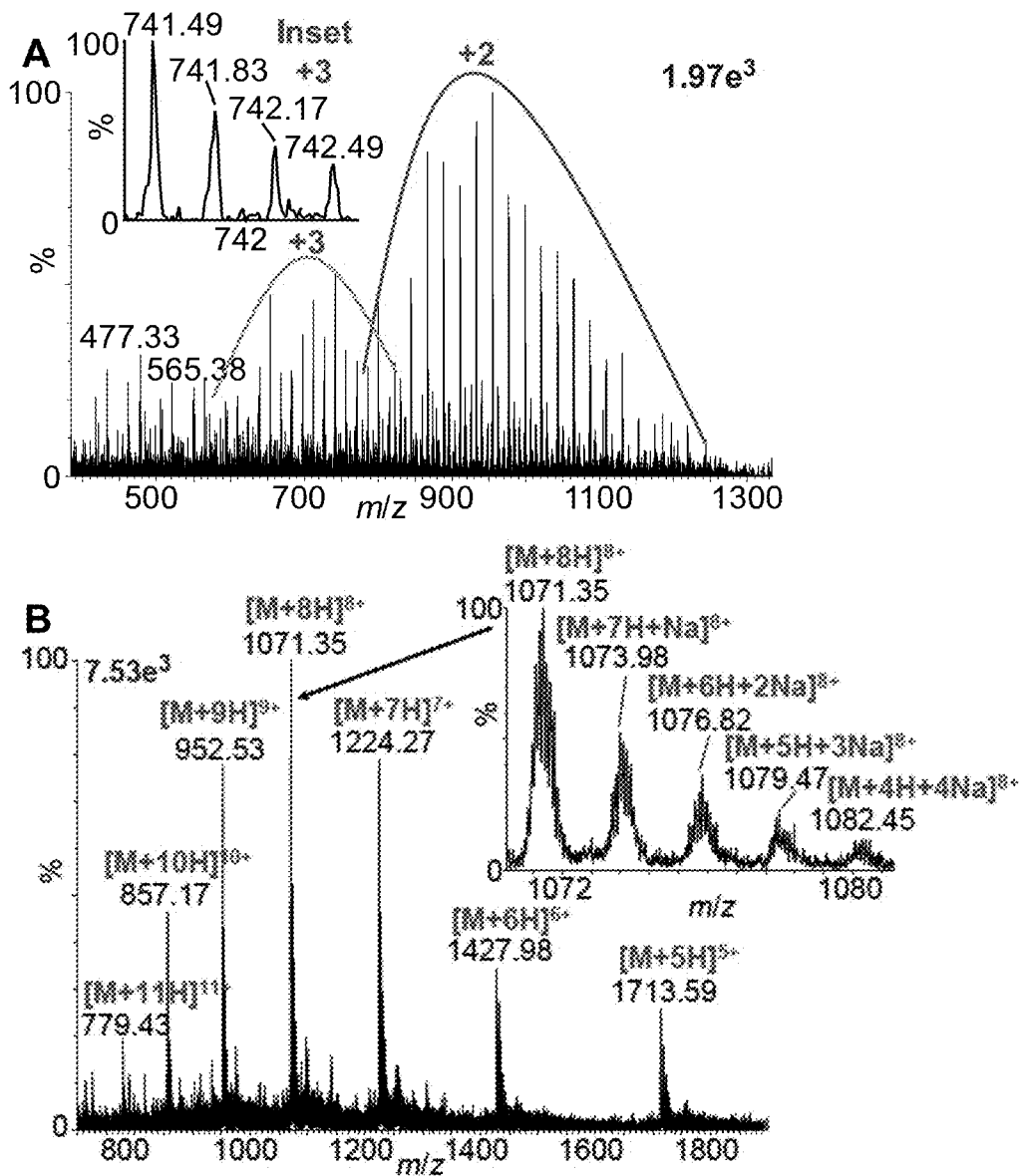
FIG. 27 illustrates MAIV using the vacuum source of (top) a synthetic polymer (PEGDME 2000) using LiCl and (bottom) ubiquitin (MW 8561) and 1 M NaCl as salt additives to the sample solution using 3-NBN as the matrix.

FIG. 27 illustrates MAIV using the vacuum source of (top) a synthetic polymer (PEGDME 2000) using LiCl and (bottom) ubiquitin (MW 8561) and 1 M NaCl as salt additives to the sample solution using 3-NBN as the matrix. The insets show the isotopic distribution of charge states. Synthetic polymers frequently depend on salt addition for forming ions in MS and are useful with MAIV. The protein is robustly analyzed by MAIV in the presence of high salt content and desirably as protonated ions.

Figure 28:
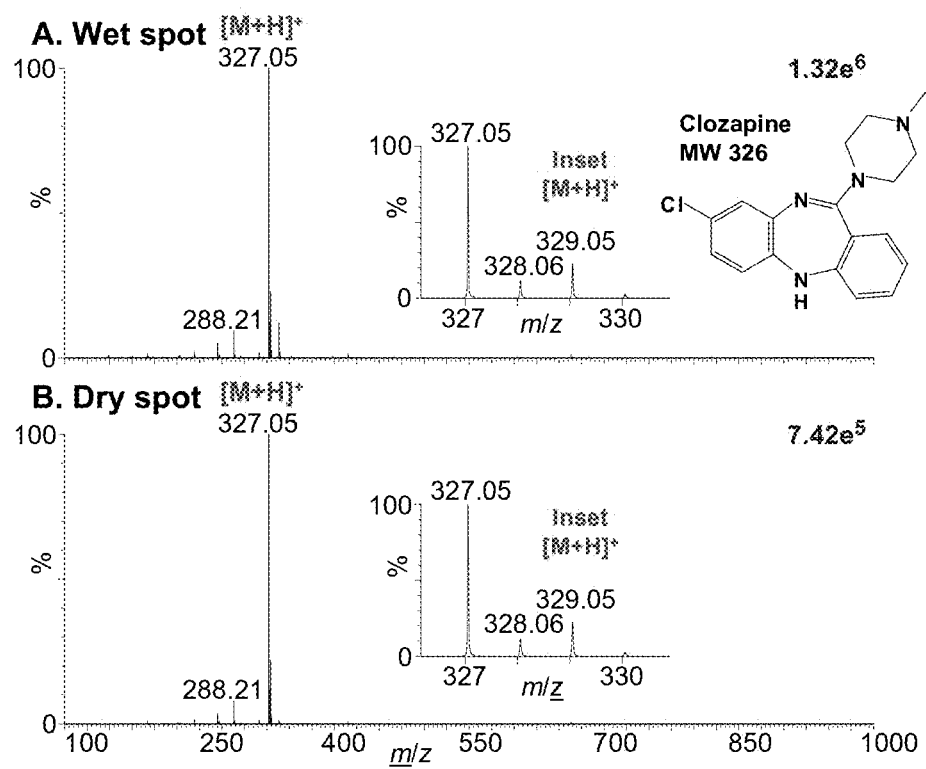
FIG. 28 illustrates the MAIV analyses of (top) a wet sample spot and (bottom) completely dried sample spot using 3-NBN as the matrix prior to introduction to the vacuum source.

FIG. 28 illustrates the MAIV analyses of (top) a wet sample spot and (bottom) completely dried sample spot using 3-NBN as the matrix prior to introduction to the vacuum source.

Figure 29:
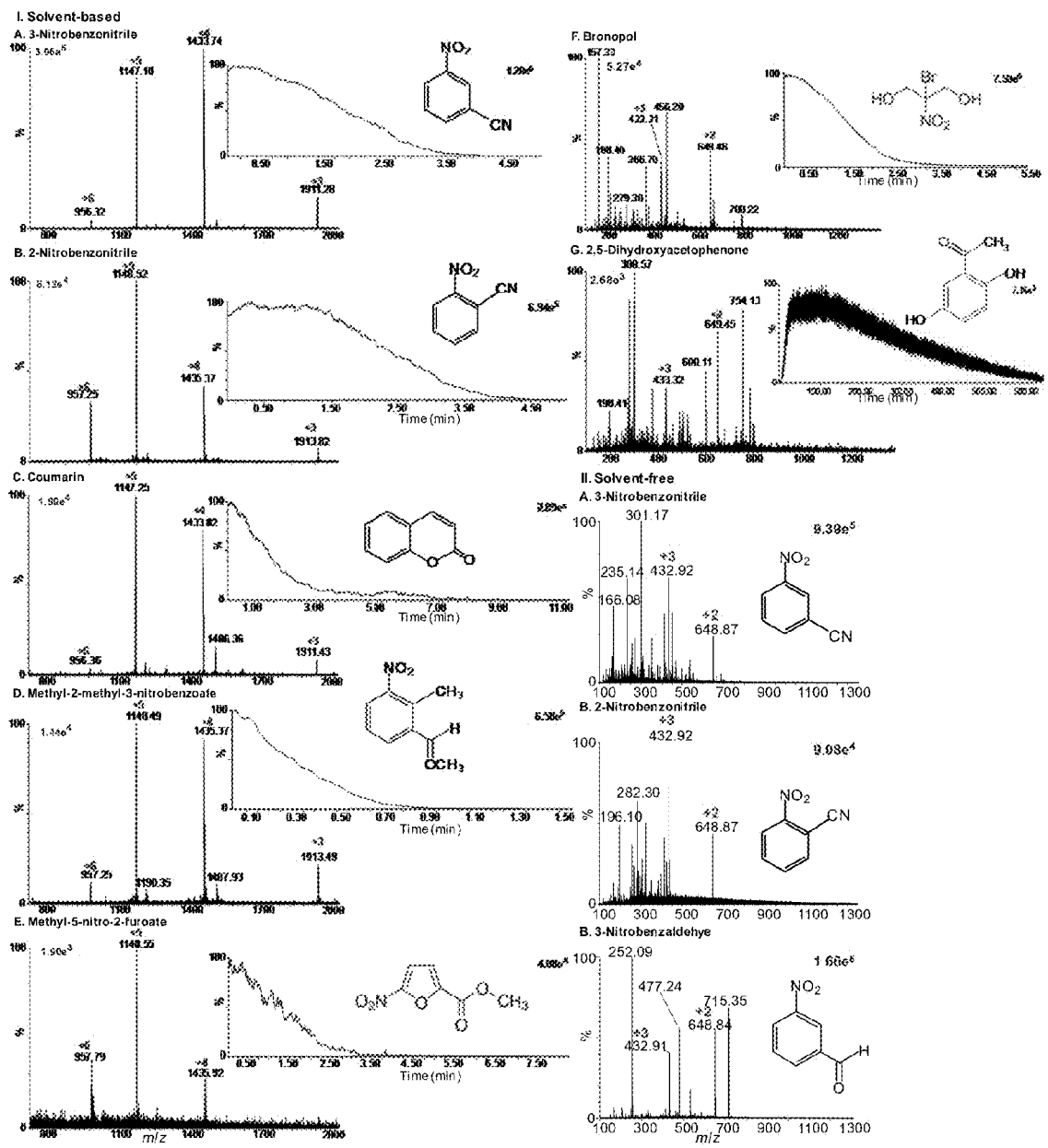
FIG. 29 illustrates eight MAIV matrices using the vacuum source. The matrix structure used is indicated in each mass spectrum.

FIG. 29 illustrates eight MAIV matrices using the vacuum source. The matrix structure used is indicated in each mass spectrum. Seven samples were prepared solvent-based using the droplet and three solvent-free. The total ion chronogram's (TIC's) (right) provide an indication of the duration of the ionization process.

Figure 30:
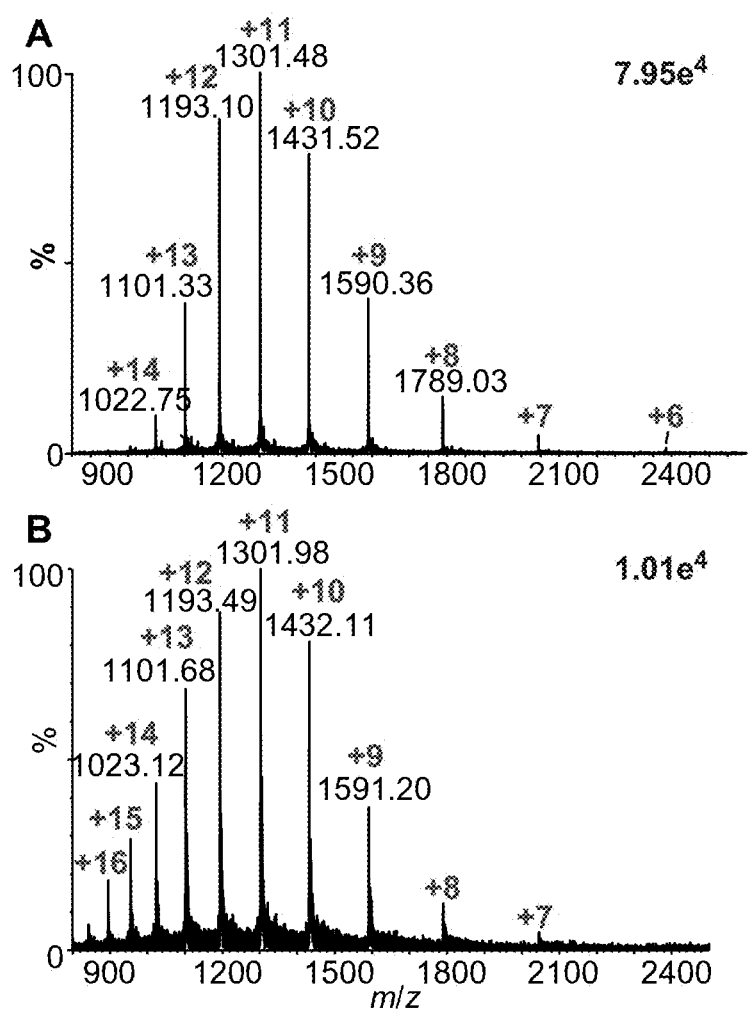
FIG. 30 illustrates MAIV of lysozyme (MW 14300) using a binary matrix mixture of 3-NBN:CHCA 1.6:1 and (top) the vacuum source or (bottom) the AP source.

FIG. 30 illustrates MAIV of lysozyme (MW 14300) using a binary matrix mixture of 3-NBN:CHCA 1.6:1 and (top) the vacuum source or (bottom) the AP source.

Figure 31:
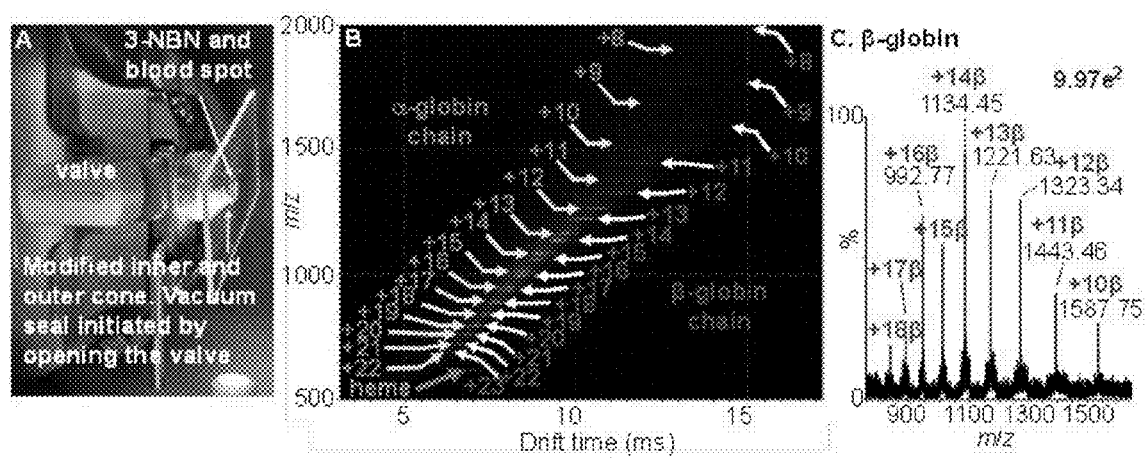
FIG. 31 illustrates MAIV of whole blood extracted from a band aid using the modified ESI skimmer cone (from here on referred to as the AP source).

FIG. 31 illustrates MAIV of whole blood extracted from a band aid using the modified ESI skimmer cone (from here on referred to as the AP source). A picture of the design using a glass plate (left), the IMS-MS 2-D plot of drift time versus m/z (middle) exemplifying the output of combining instantaneous ionization with instantaneous separation and detection, and the cleanly separated beta chain of hemoglobin obtained through the IMS separation (right). A unique pictorial 'snap-shot' is obtained of the biological matrix blood.

Figure 32:
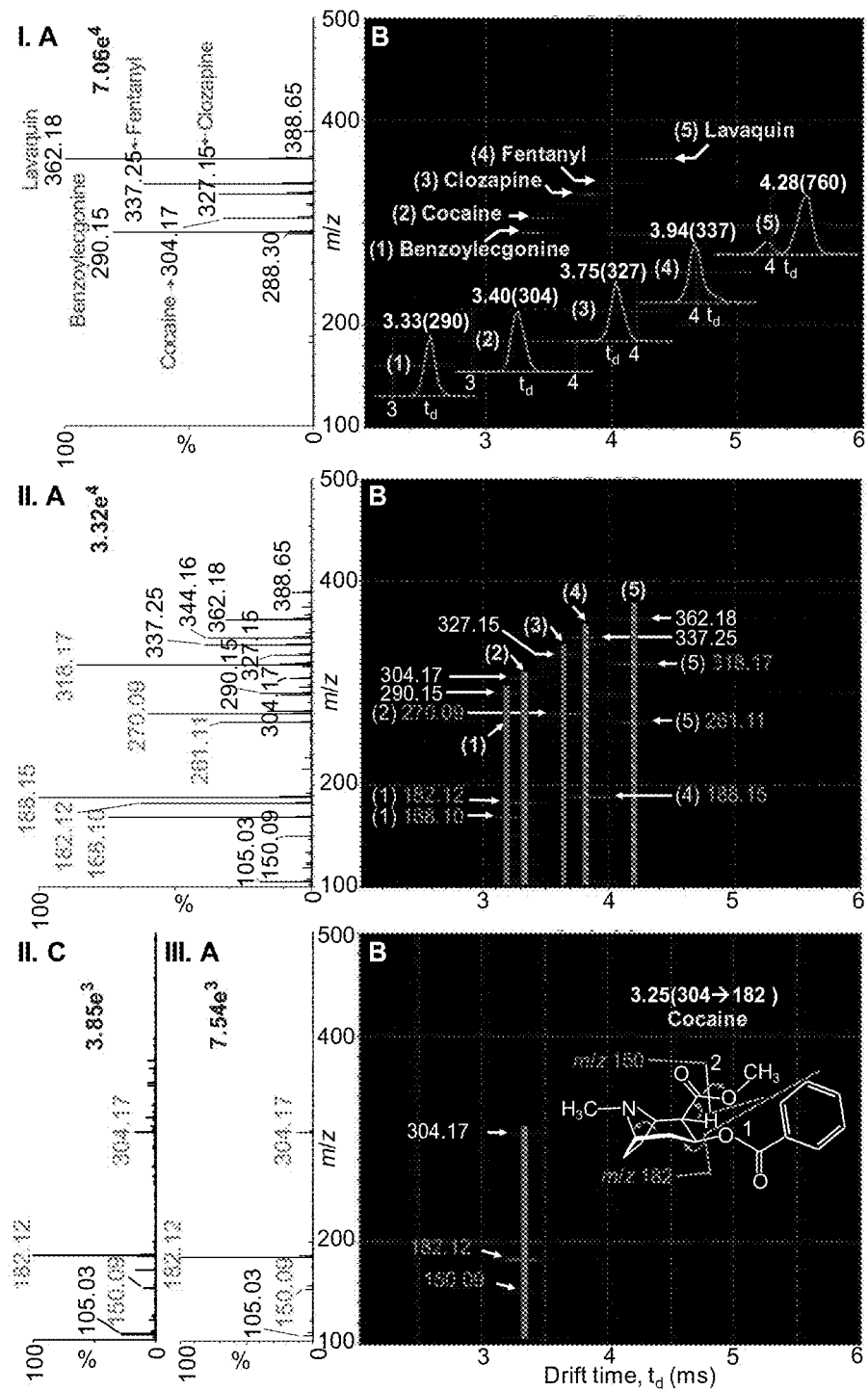
FIG. 32 illustrates using the source displayed in FIG. 31 to analyze by MAIV-IMS-MS a mixture of five drugs.

FIG. 32 illustrates using the source displayed in FIG. 31 to analyze by MAIV-IMS-MS a mixture of five drugs. Top: Mass spectrum (left) and IMS-MS 2-D plot (right). The extracted drift times and m/z values are sufficiently distinctive to identify compounds using this so called nested dataset. Middle: the entire set of ions is fragmented (CID) simultaneously without precursor selection and MS/MS data extracted for each compound and characterization achieved. MS/MS total mass spectrum (left) and IMS-MS 2-D plot (right). Bottom: the extracted MS/MS dataset is displayed for cocaine: mass spectrum (left) extracted from experiment without precursor selection and (right) traditional CID with precursor selection including the respective 2-D plot (far right) with an inset for fragmentation path.

Figure 33:
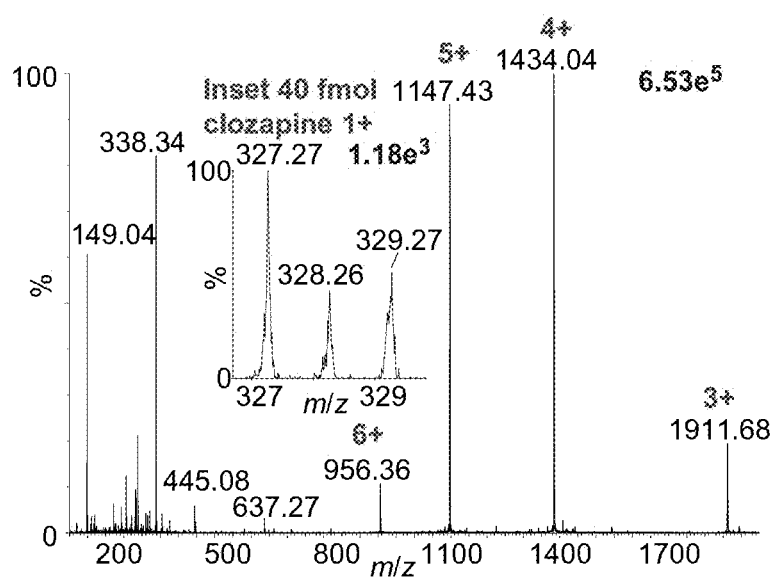
FIG. 33 illustrates MAIV of 40 fmol clozapine and 20 pmol bovine insulin using 3-NBN. Incorporating the IMS dimension increases the dynamic range of the experiment.

FIG. 33 illustrates MAIV of 40 fmol clozapine and 20 pmol bovine insulin using 3-NBN. Incorporating the IMS dimension increases the dynamic range of the experiment.

Figure 34:
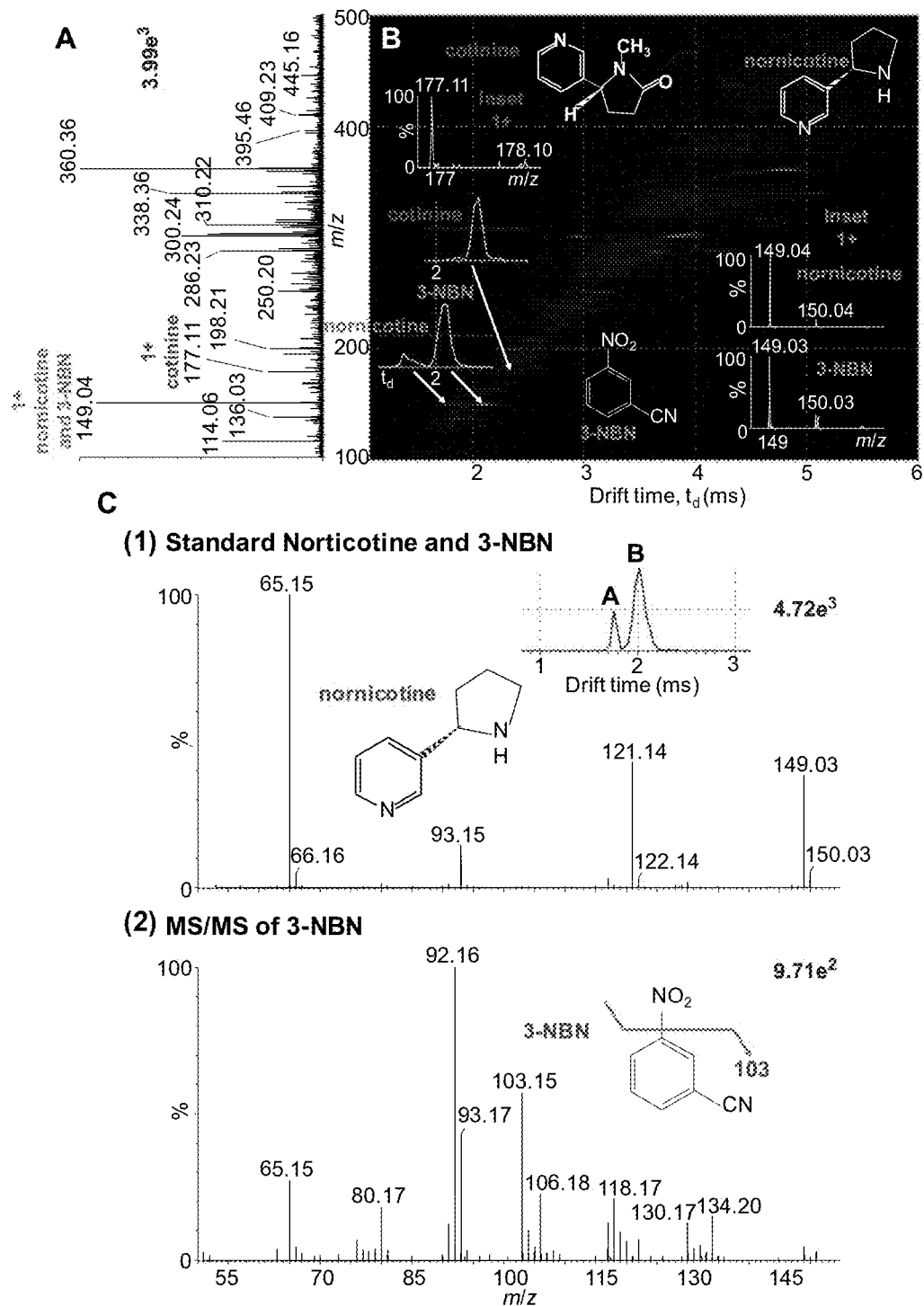
FIG. 34 illustrates MAIV of nicotine and nornicotine using 3-NBN. Incorporating the IMS dimension separates isobaric molecules of nornicotine and 3-NBN.

FIG. 34 illustrates MAIV of nicotine and nornicotine using 3-NBN. Incorporating the IMS dimension separates isobaric molecules of nornicotine and 3-NBN.

Figure 35:
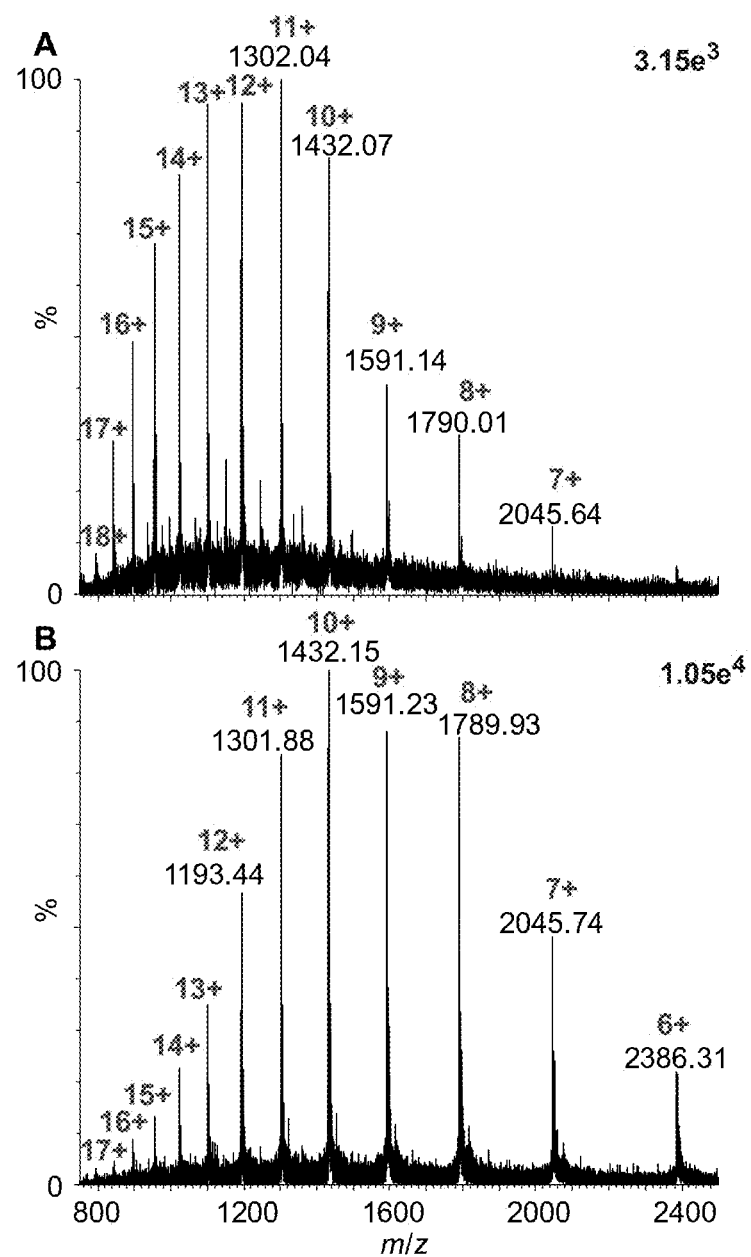
FIG. 35 illustrates MAIV of lysozyme using 3-NBN from a buffered solution showing the mass spectra (top) in which the solution of analyte was added to filter paper and while wet the matrix in a separate solution was added, and (bottom) the matrix solution was added to filter paper and dried. To this precoated matrix layer the analyte was added.

FIG. 35 illustrates MAIV of lysozyme using 3-NBN from a buffered solution showing the mass spectra (top) in which the solution of analyte was added to filter paper and while wet the matrix in a separate solution was added, and (bottom) the matrix solution was added to filter paper and dried. To this precoated matrix layer the analyte was added.

Figure 36:
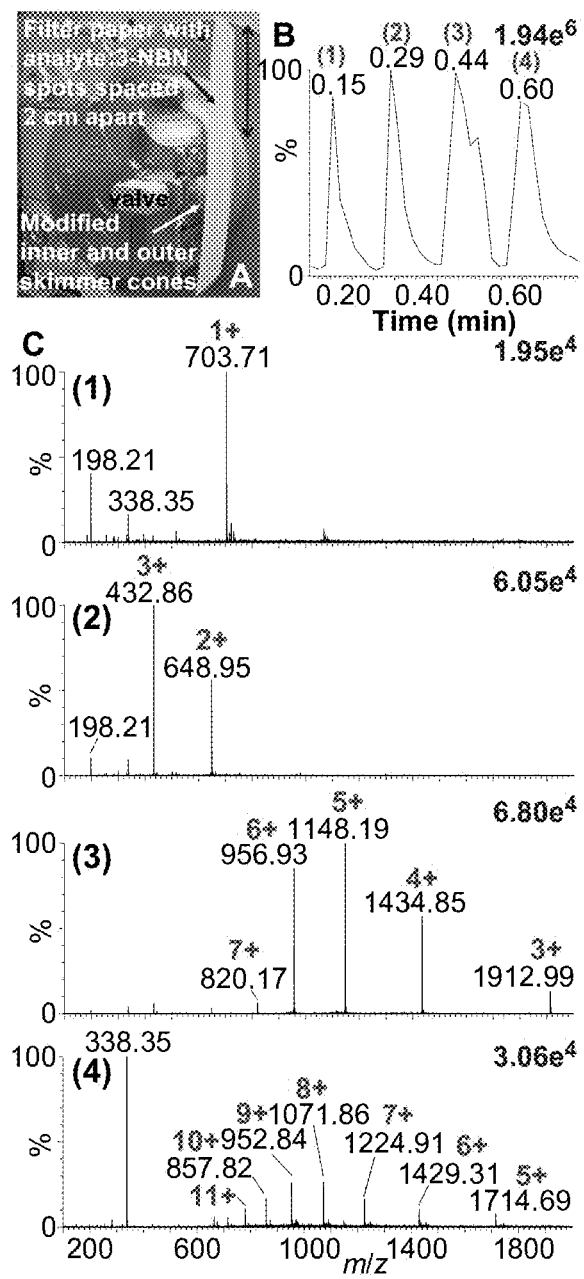
FIG. 36 illustrates MAIV using 3-NBN of four different samples in less than 1 minute using the AP source sliding the paper strip, onto which the sample was applied, across the inlet opening to create sub-atmospheric pressure at the sample.

FIG. 36 illustrates MAIV using 3-NBN of four different samples in less than 1 minute using the AP source sliding the paper strip, onto which the sample was applied, across the inlet opening to create sub-atmospheric pressure at the sample. A picture of the design is shown (top left), the TIC is shown (top right), and the mass spectra is shown (bottom).

Figure 37:
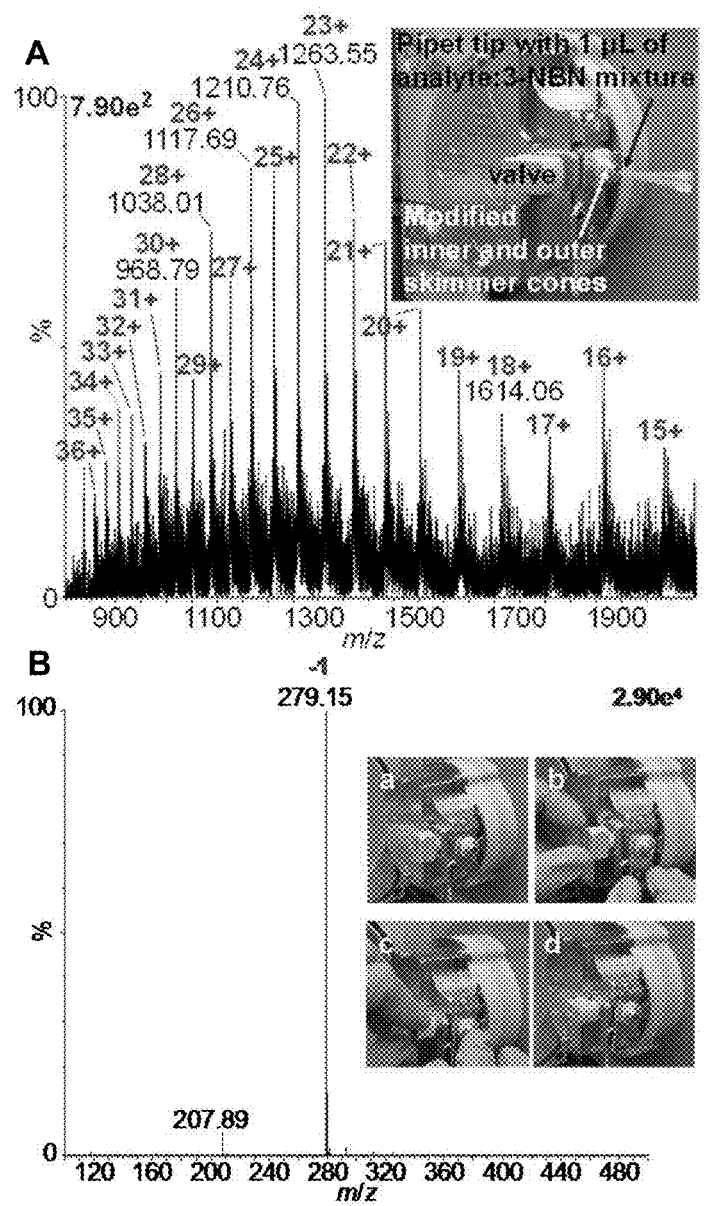
FIG. 37 illustrates MAIV using (top) a pipet tip as a sample substrate as demonstrated in FIG. 7.

FIG. 37 illustrates MAIV using (top) a pipet tip as a sample substrate as demonstrated in FIG. 7. A picture of the method (top) and the mass spectrum (bottom) of carbonic anhydrase (MW ~29,000) using the solvent system 1:1 acetonitrile:water with 3-NBN as the matrix. Alternatively (bottom) a glass plate substrate (top) is used to analyze a fatty acid (MW 280) in the negative mode using the solvent system methanol with the 3-NBN.

Figure 38:
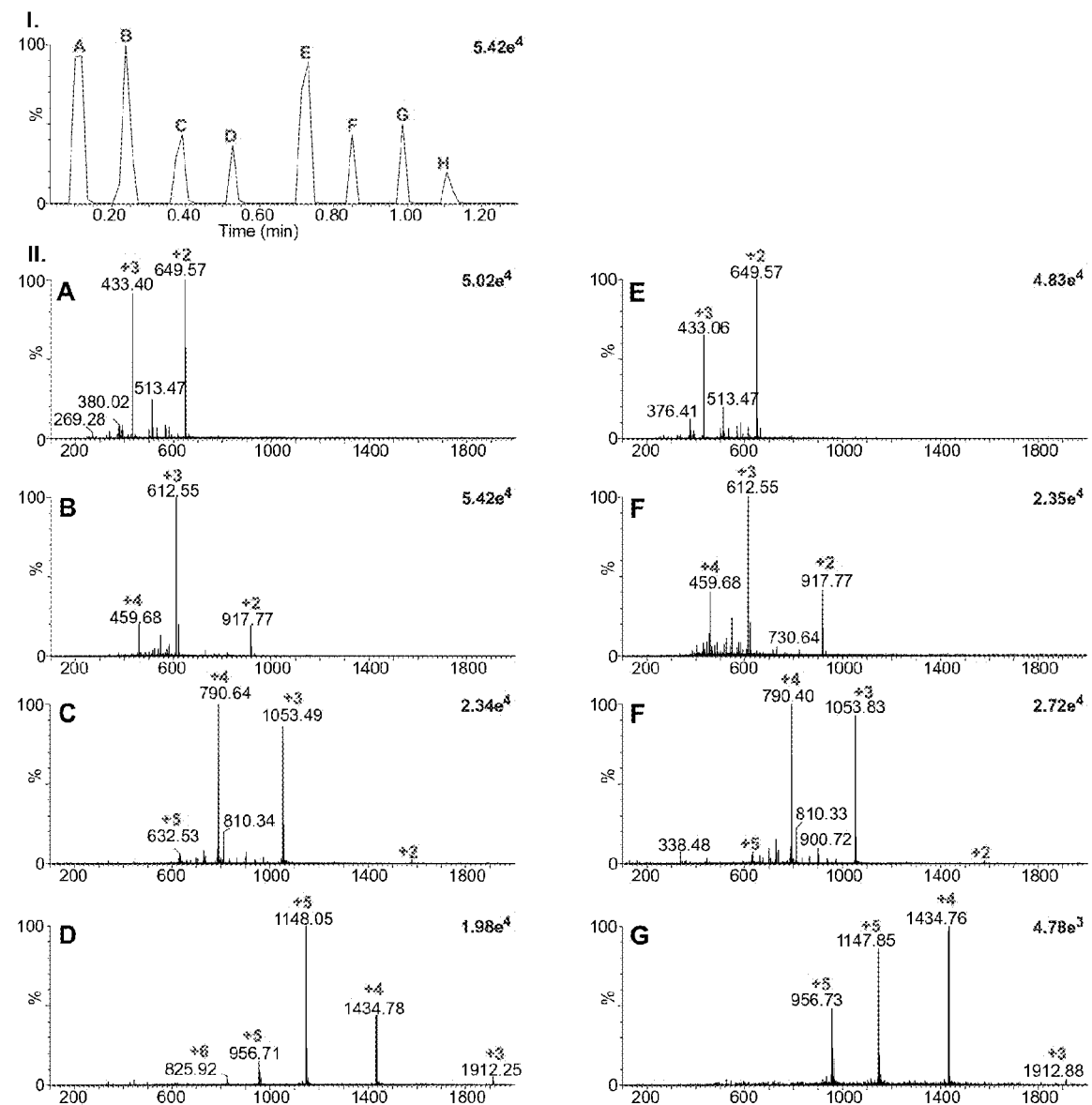
FIG. 38 illustrates MAIV with 3-NBN as the matrix using a 8-channel multiple pipet tips dispenser.

FIG. 38 illustrates MAIV with 3-NBN as the matrix using a 8-channel multiple pipet tips dispenser.

Figure 39:
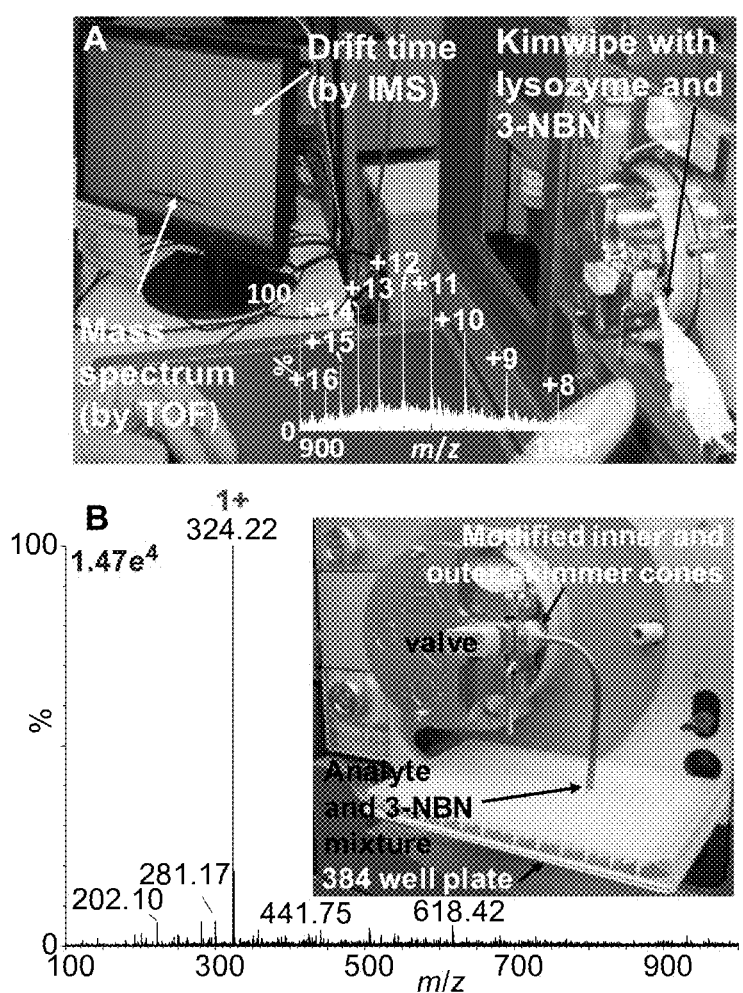
FIG. 39 illustrates MAIV and the 3-NBN matrix of LSD (MW 323) using the AP source with a nozzle extension analyzing the sample from the bottom of one well of the well plate similar to FIG. 6.

FIG. 39 illustrates MAIV and the 3-NBN matrix of LSD (MW 323) using the AP source with a nozzle extension analyzing the sample from the bottom of one well of the well plate similar to FIG. 6.

Figure 40:
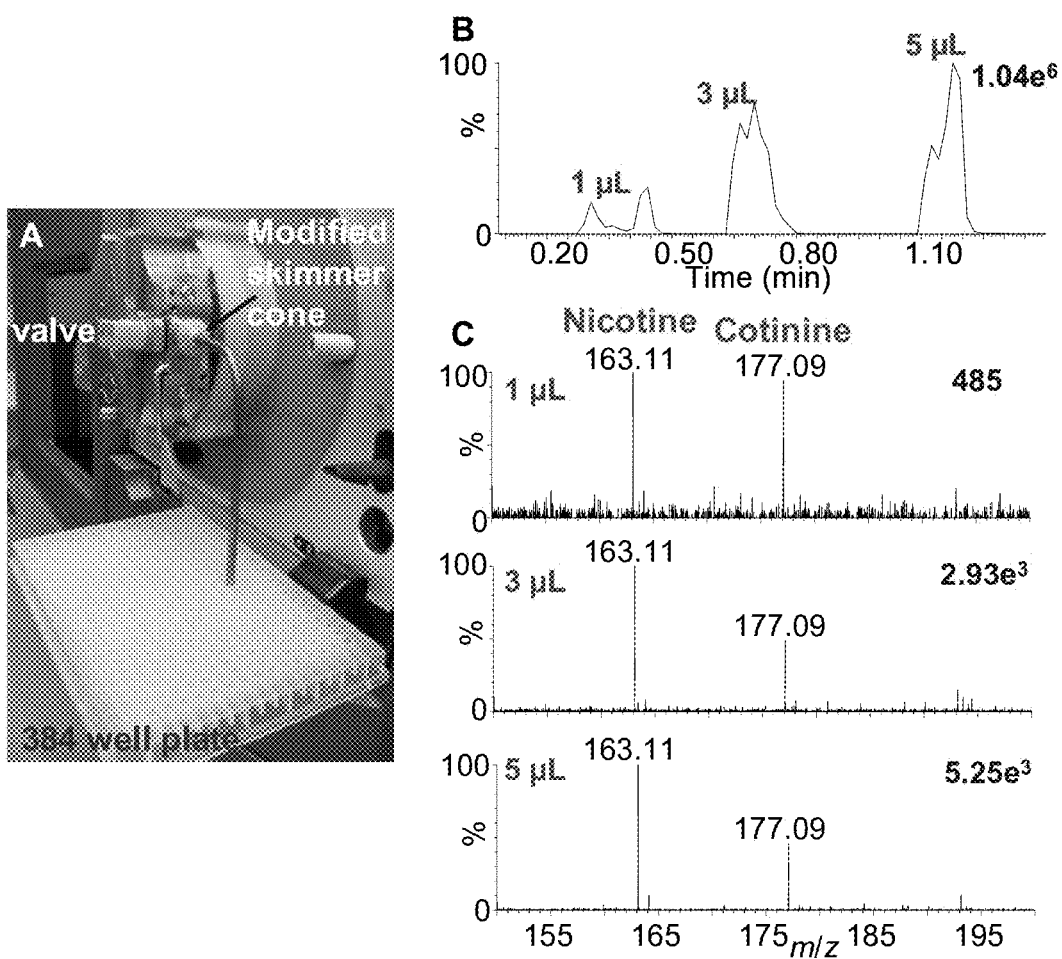
FIG. 40 illustrates MAIV and the 3-NBN matrix of nicotine (MW 162) using the AP source analyzing the sample from well of the 384-well plate (pictures top left).

FIG. 40 illustrates MAIV and the 3-NBN matrix of nicotine (MW 162) using the AP source analyzing the sample from well of the 384-well plate (pictures top left). 1, 3 and 5 µL of 5000 ng mL$^{-1}$ nicotine were deposited in separate well. This increase is reflected in the TIC. The nearly background free mass spectra are shown to the bottom right.

FIG. 41 illustrates MAIV analyses of Clarithromycin (MW 747) directly from a tablet using the 3-NBN matrix and the AP source.

Figure 42:
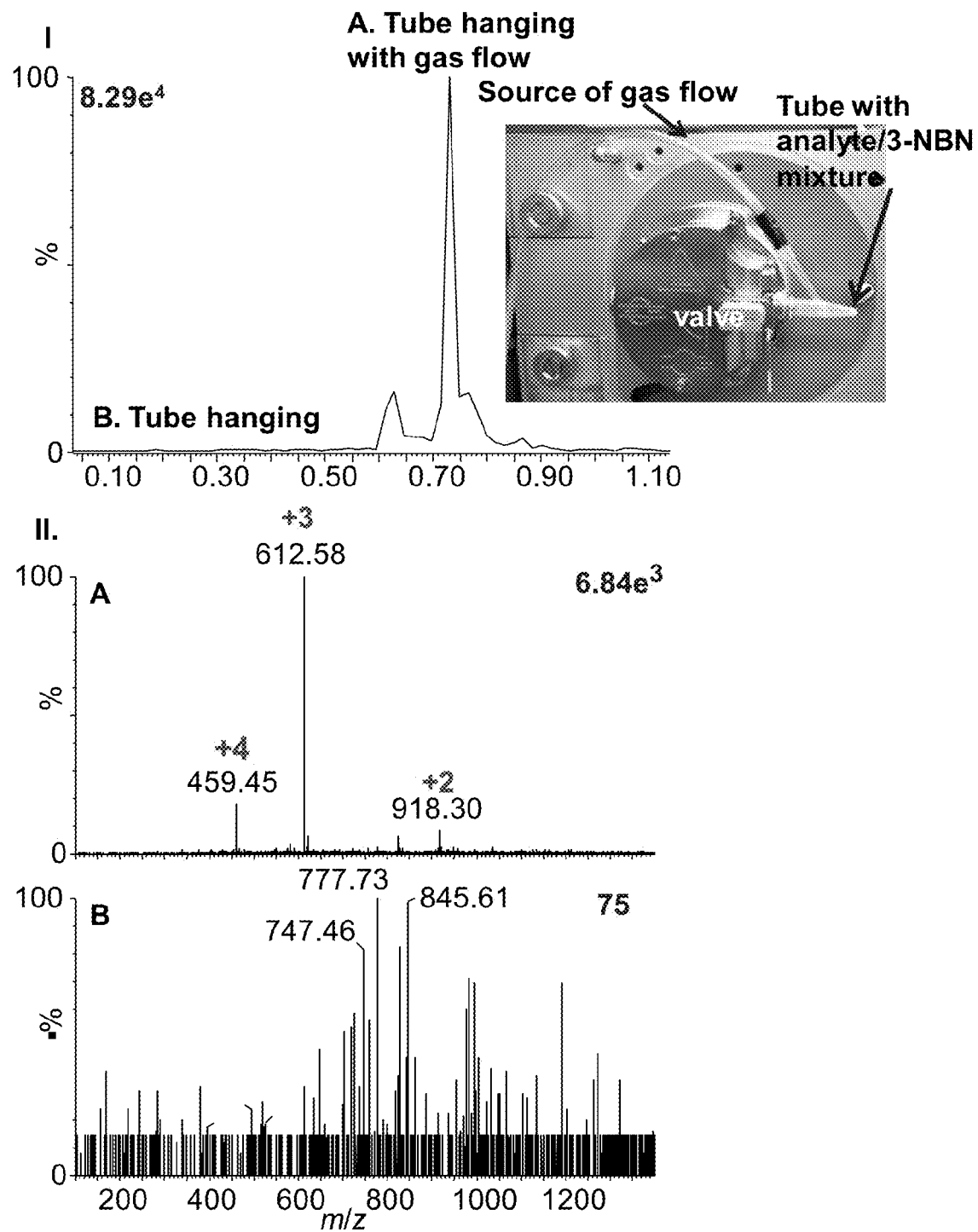
FIG. 42 illustrates MAIV using the AP source and 3-NBN as the matrix. Top: Picture and TIC provide view of the set up and the TIC's (right) provide an indication of the duration of the ionization process.

FIG. 42 illustrates MAIV using the AP source and 3-NBN as the matrix. Top: Picture and TIC provide view of the set up and the TIC's (right) provide an indication of the duration of the ionization process. A stream of gas close to the sample aids in ionization as shown in the middle Figure; bottom is the result of no airflow provided.

Figure 43:
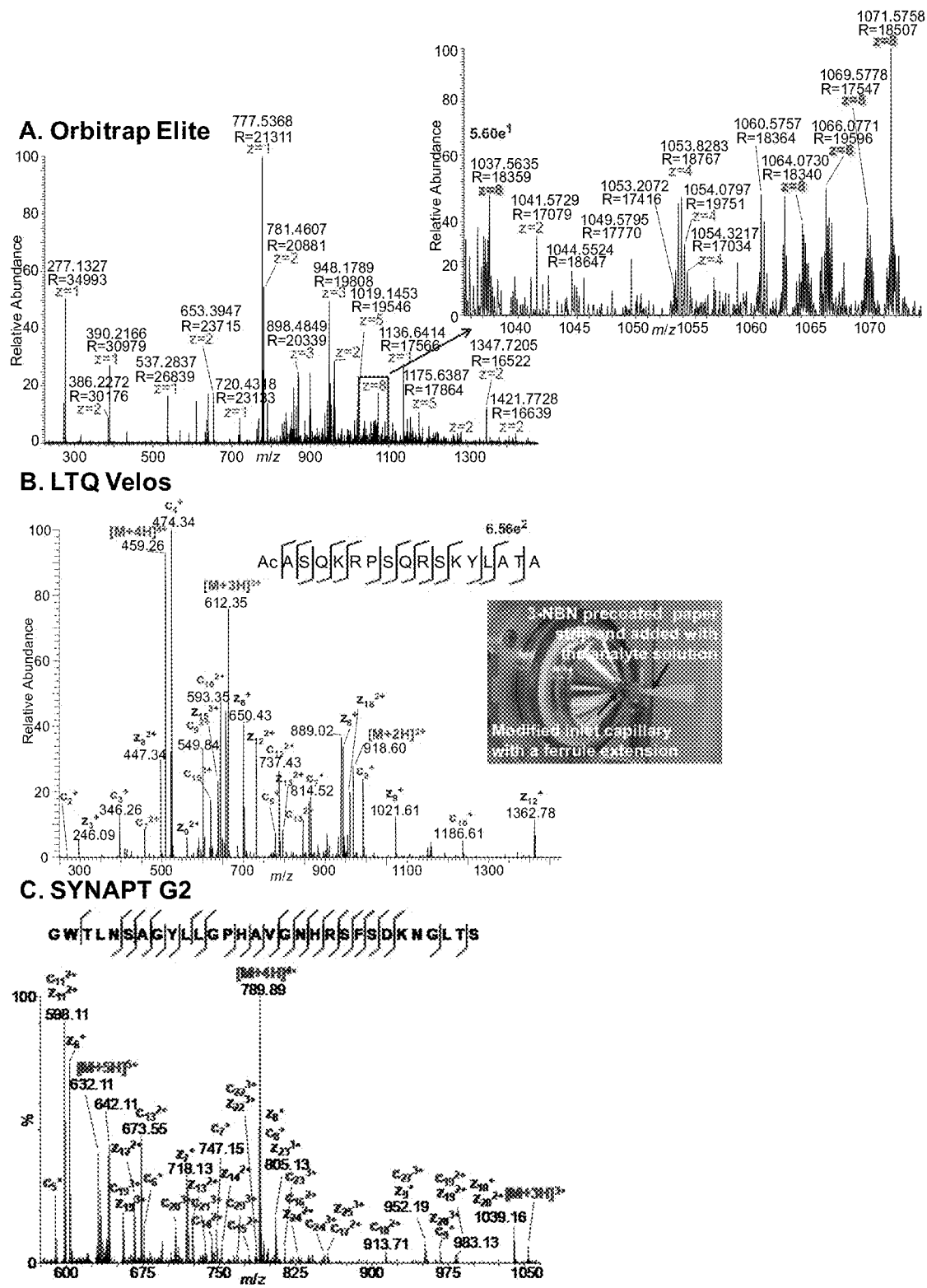
FIG. 43 illustrates MAIV-ETD using the AP source.

FIG. 43 illustrates MAIV-ETD using the AP source. Top: Ubiquitin charge state +11 on Orbitrap using the glass plate as the substrate with a vacuum leak; Middle: charge state +4 of myelin basic protein (MBP) on LTQ Velos using a paper (see picture to the right) as the substrate; Bottom: Galanin charge state +5 on SYNAPT G2 using foil as the substrate. Fragment ions are sorted in the IMS dimension according to charge states (not shown) providing speed in acquisition and analyses.

Figure 44:
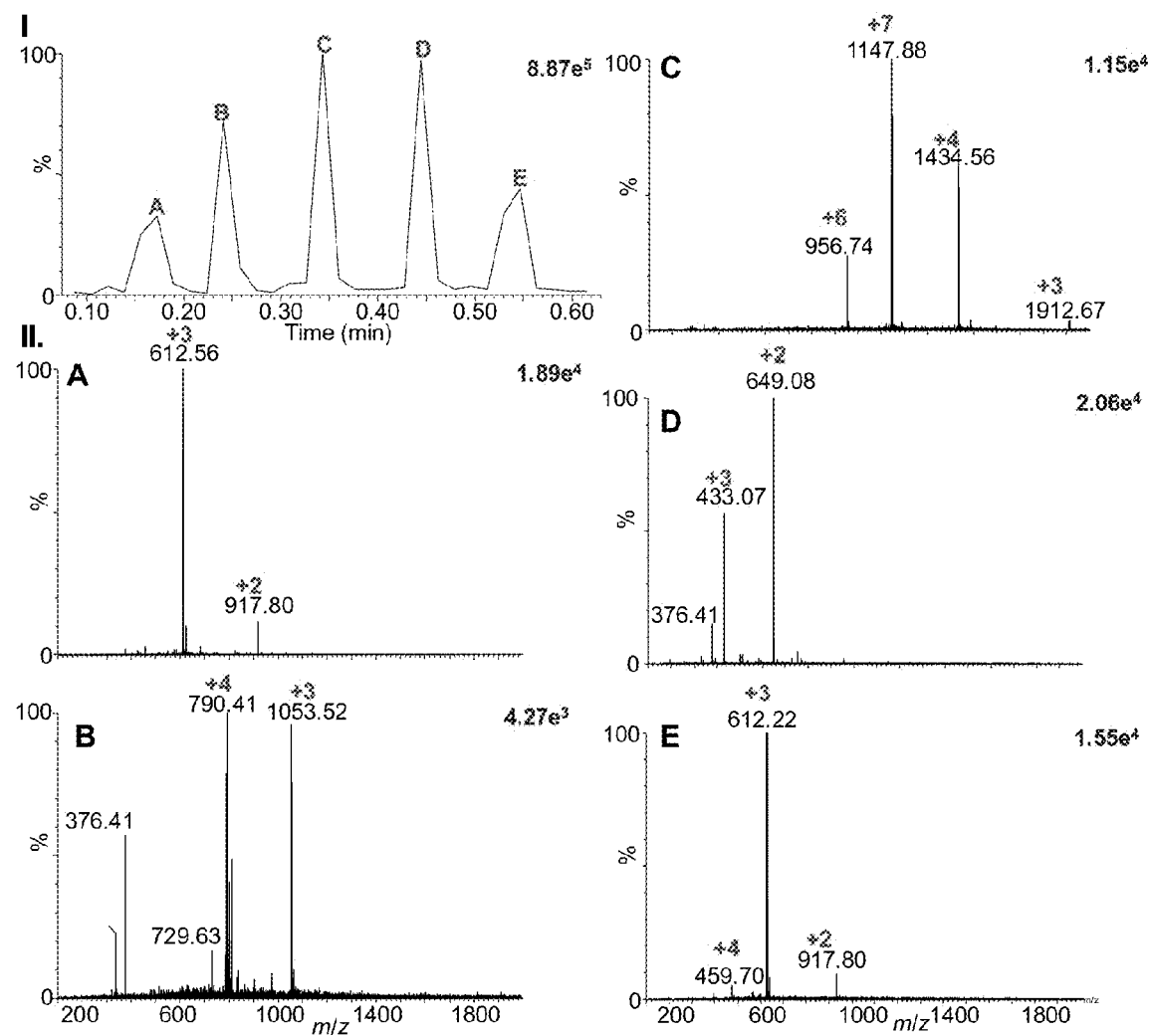
FIG. 44 illustrates MAIV using 3-NBN of five different samples in less than 3 seconds using a gently adjusted laser to heat the sample close to the skimmer cone similar to FIG. 8.

FIG. 44 illustrates MAIV using 3-NBN of five different samples in less than 3 seconds using a gently adjusted laser to heat the sample close to the skimmer cone similar to FIG. 8.

It should be understood that the laser can be aligned in transmission or reflection geometry relative to the sample to be heated.

Figure 45:
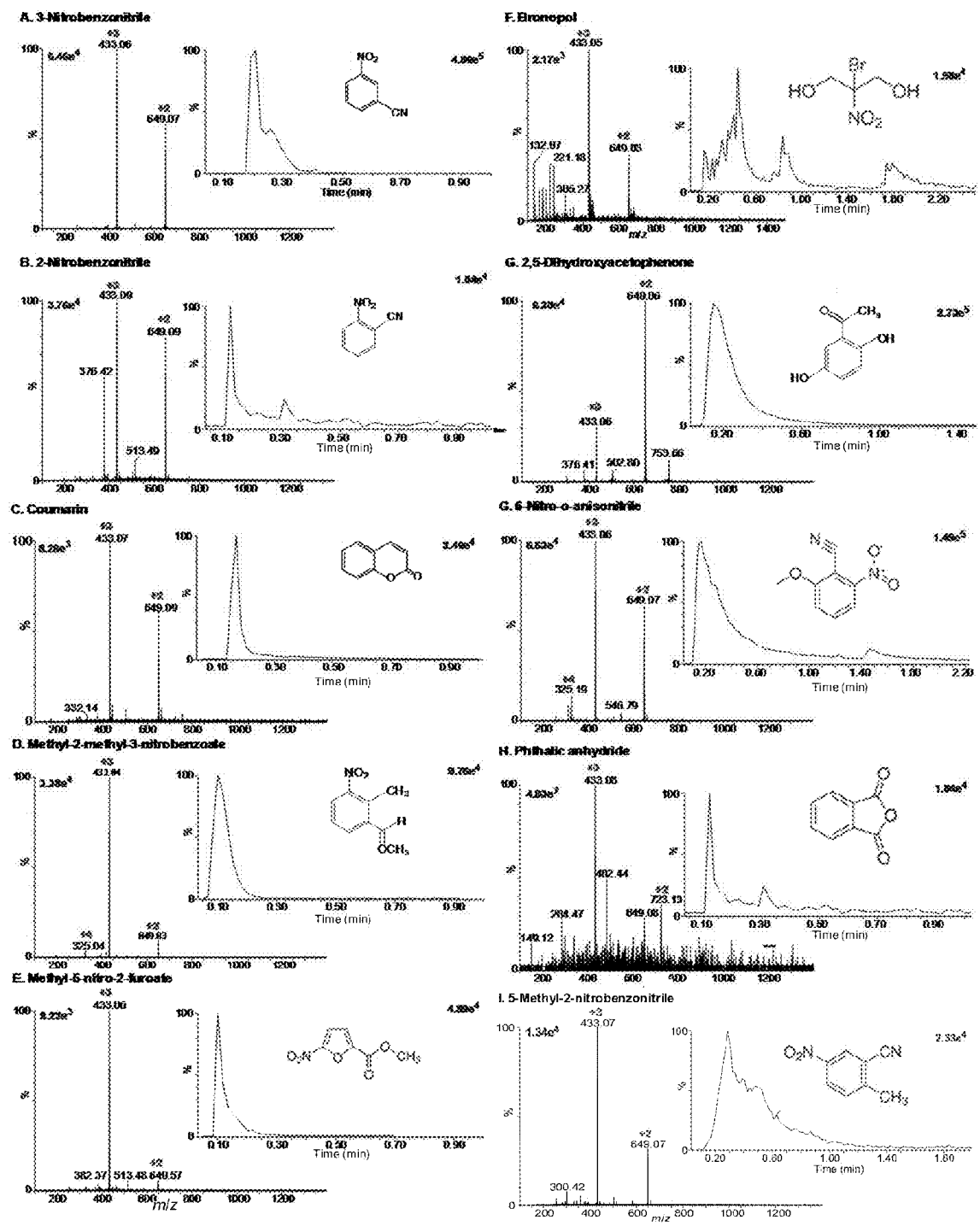
FIG. 45 illustrates nine MAIV matrices using the AP source. The structure and temperature used is indicated in each mass spectrum.

FIG. 45 illustrates nine MAIV matrices using the AP source. The structure and temperature used is indicated in each mass spectrum. The TIC's (right) provide an indication of the duration of the ionization process. A glass substrate was used as is exemplified in FIG. 6.

Figure 46:
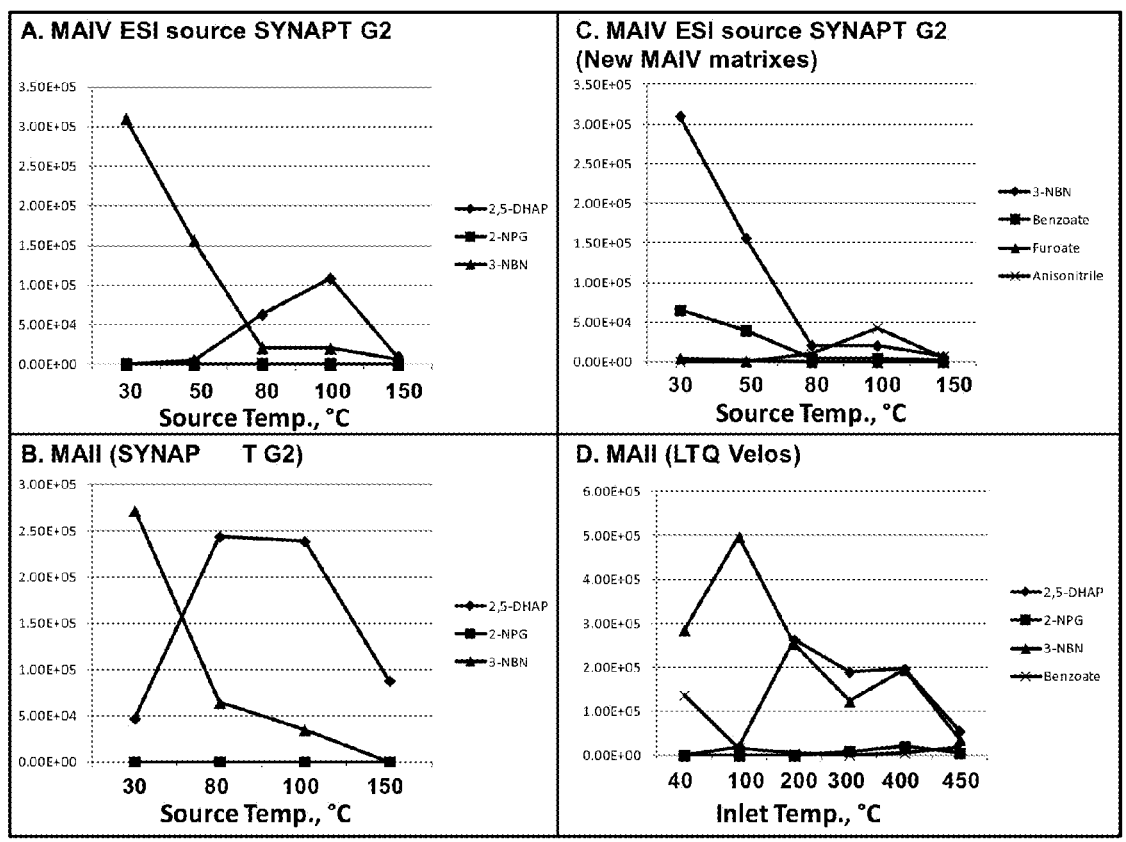
FIG. 46 illustrates a MAIV matrix/temperature study (in the range of 30° C. to 450° C.) using the 3-NBN, 2,5-DHAP, 2-NPG, methyl-2-methyl-3-nitrobenzoate, methyl-5-nitro-2-furoate, and 6-nitro-o-anisonitrile matrixes and the AP source of the SYNAPT G2 (skimmer cone source, maximum temperature that can be applied is 150° C.) and the LTQ Velos (inlet tube, maximum temperature that can be applied is 500° C.).

FIG. 46 illustrates a MAIV matrix/temperature study (in the range of 30° C. to 450° C.) using the 3-NBN, 2,5-DHAP, 2-NPG, methyl-2-methyl-3-nitrobenzoate, methyl-5-nitro-2-furoate, and 6-nitro-o-anisonitrile matrixes and the AP source of the SYNAPT G2 (skimmer cone source, maximum temperature that can be applied is 150° C.) and the LTQ Velos (inlet tube, maximum temperature that can be applied is 500° C.).

Figure 47:
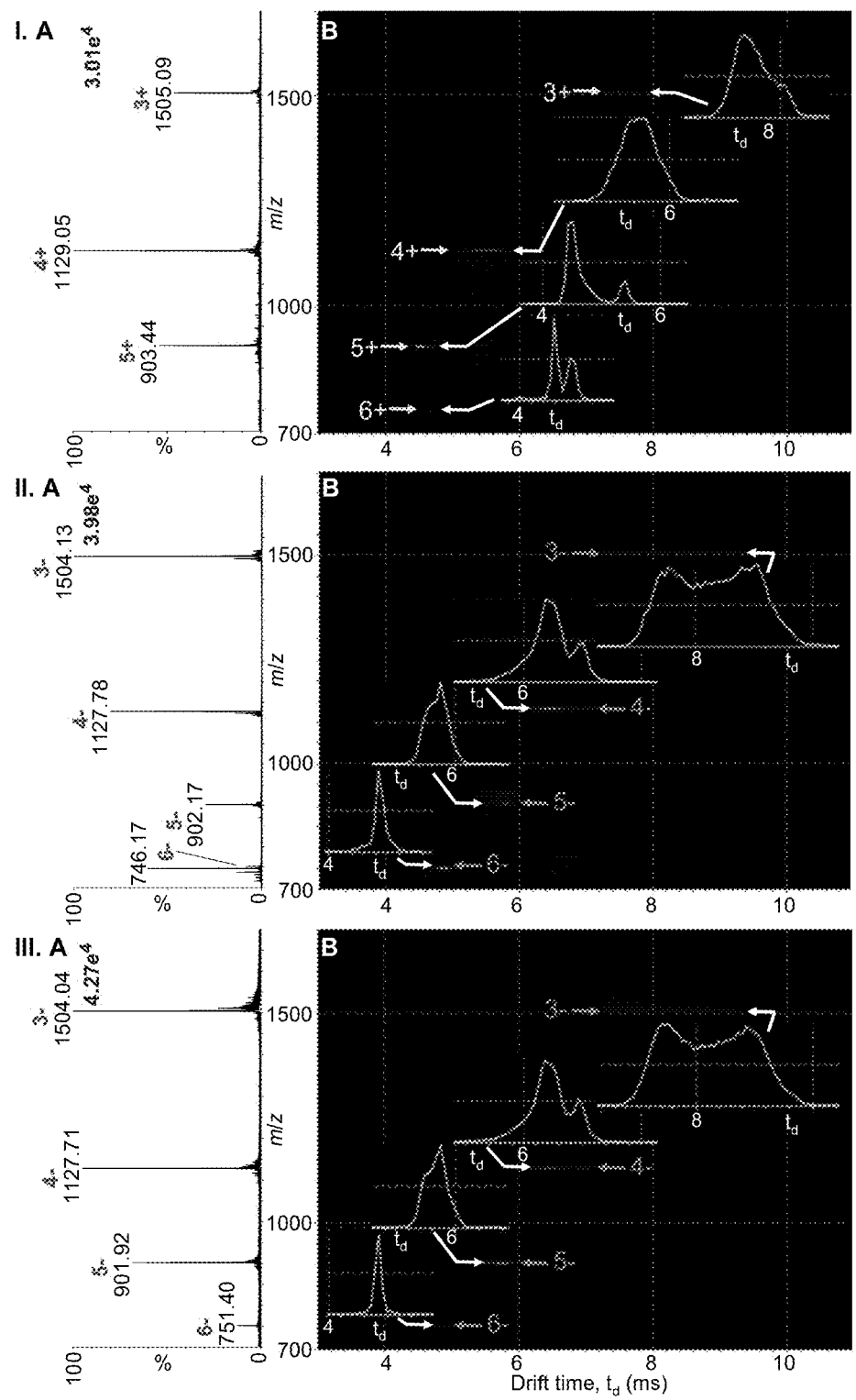
FIG. 47 illustrates MAIV-IMS-MS: (right panel) 2-D plot display of drift time vs. m/z and (left panel) mass spectra of beta-amyloid (1-42) (MW 4511 Da) using MAIV with 3-NBN matrix in (I) positive mode and (II) negative mode on the intermediate pressure vacuum source of SYNAPT G2, and (III) ESI comparison in negative mode.

FIG. 47 illustrates MAIV-IMS-MS: (right panel) 2-D plot display of drift time vs. m/z and (left panel) mass spectra of beta-amyloid (1-42) (MW 4511 Da) using MAIV with 3-NBN matrix in (I) positive mode and (II) negative mode on the intermediate pressure vacuum source of SYNAPT G2, and (III) ESI comparison in negative mode. Insets show extracted drift times useful for cross-section analyses directly from its biological or synthetic (not shown) environments. The advantage of using MAIV matrices in addition of the simplicity, sensitivity, robustness, and no requirement for applied energy or force is that the matrices sublime or evaporate when placed under vacuum conditions commonly used with mass spectrometers and vacuum operated ion mobility spectrometers. Thus, the matrix will not accumulate on the lens elements and contaminate the instrument as is the case with MALDI, LSII, and MAII.

Although the systems and methods have been described in terms of exemplary embodiments, they are limited thereto. Rather, the appended claims should be construed broadly, to include other variants and embodiments of the systems and methods, which may be made by those skilled in the art without departing from the scope and range of equivalents of the systems and methods.

What is claimed is:

1. A method of ionizing an analyte for analysis by ion mobility spectrometry or mass spectrometry, comprising:
   providing a sample comprising an analyte and a matrix;
   producing gas phase positive or negative ions of the analyte without irradiating the sample or analyte with a laser, without exposing the sample or analyte to an electrical potential, and without exposing the sample or analyte to high velocity particles to produce said gas phase positive or negative ions of the analyte; and
   wherein the step of producing gas phase positive or negative ions does not include passing the sample or analyte through a heated ion transfer region and without a heated ion skimmer.

2. The method of claim 1, further comprising the step of heating the sample to a temperature between −80° C. and 150° C.

3. The method of claim 2, wherein the temperature is between 25° C. and 80° C.

4. The method of claim 1, further comprising the step of placing the sample under a sub-atmospheric pressure.

5. The method of claim 4, wherein said sub-atmospheric pressure is between 750 mm Hg and $1 \times 10^{-7}$ mm Hg.

6. The method of claim 1, wherein said gas phase positive or negative ions are singly or multiply charged.

7. The method of claim 1, wherein the step of producing gas phase positive or negative ions of the analyte is a spontaneous process.

8. The method of claim 1, wherein said matrix has a molecular weight between 50 atomic mass units and 600 atomic mass units.

9. The method of claim 8, wherein said matrix has a molecular weight between 100 atomic mass units and 400 atomic mass units.

10. The method of claim 1, wherein said matrix is in a solid phase at room temperature and pressure.

11. The method of claim 1, wherein said matrix is in a liquid phase at room temperature and pressure.

12. The method of claim 1, wherein said matrix sublimes or evaporates under a sub-atmospheric pressure.

13. The method of claim 12, wherein said matrix sublimes or evaporates when placed under a sub-atmospheric pressure at a temperature less than 120° C.

14. The method of claim 13, wherein said matrix sublimes or evaporates when placed under a sub-atmospheric pressure at a temperature less than 70° C.

15. The method of claim 1, wherein the matrix is 3-nitrobenzonitrile, 2-nitrobenzonitrile, 5-methyl-2-nitrobenzonitrile, coumarin, methyl-2-methyl-3-nitrobenzoate, methyl-5-nitro-2-furoate, 2-bromo-2-nitropropane-1,3-diol), 3-nitrobenzaldehyde, 6-nitro-o-anisonitrile, phthalic anhydride, or mixtures thereof.

16. The method of claim 1, wherein said analyte comprises biological tissue, biological material, eatable goods, polymers, paintings, archaeological artifacts, artificial bone, skin, urine, or blood.

17. The method of claim 1, wherein said analyte comprises a synthetic compound.

18. The method of claim 1, wherein the matrix comprises a compound that can absorb laser light to produce heat continuously or discontinuously.

19. The method of claim 1, further comprising the step of placing the sample on a substrate.

20. The method of claim 19, wherein said substrate is comprised of metal, paper, cloth, ribbon, glass, plastic, polymer, sodium dodecyl sulfate gel, agarose gel, paper chromatography plate, silica plate or woven fiber.

21. The method of claim 1, wherein said sample further comprises a solvent.

22. The method of claim 21, wherein said solvent is water, methanol, ethanol, isopropanol, acetonitrile, tetrahydrofuran, chloroform, dimethylformamide, dimethyl sulfoxide, acetone, or mixtures thereof.

23. The method of claim 1, wherein said sample is prepared by mixing or grinding the analyte and matrix together.

24. The method of claim 1, wherein said sample is a solid.

25. The method of claim 24, wherein said solid sample is in a frozen state.

26. The method of claim 1, wherein said sample further comprises an ammonium salt, metal salt, acid, base, or buffer.

27. The method of claim 1, wherein said mass spectrometer or ion mobility spectrometer comprises an inlet and a region near said inlet, wherein said region near said inlet is maintained at a sub-atmospheric pressure.

* * * * *